US009221841B2

(12) United States Patent
Hans et al.

(10) Patent No.: US 9,221,841 B2
(45) Date of Patent: *Dec. 29, 2015

(54) MITOTIC KINESIN INHIBITORS AND METHODS OF USE THEREOF

(71) Applicant: Array BioPharma Inc., Boulder, CO (US)

(72) Inventors: Jeremy Hans, Boulder, CO (US); Eli M. Wallace, Boulder, CO (US); Qian Zhao, Boulder, CO (US); Shelley Allen, Boulder, CO (US); Ellen Laird, Boulder, CO (US); Joseph P. Lyssikatos, Boulder, CO (US); John E. Robinson, Boulder, CO (US); Christopher P. Corrette, Boulder, CO (US); Robert Kirk DeLisle, Boulder, CO (US); Walter C. Voegtli, Boulder, CO (US)

(73) Assignee: Array BioPharma Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/663,286

(22) Filed: Mar. 19, 2015

(65) Prior Publication Data

US 2015/0191490 A1  Jul. 9, 2015

Related U.S. Application Data

(60) Continuation of application No. 14/031,958, filed on Sep. 19, 2013, now abandoned, which is a division of application No. 13/586,355, filed on Aug. 15, 2012, now Pat. No. 8,580,828, and a division of application No. 12/822,066, filed on Jun. 23, 2010, now Pat. No. 8,268,871, and a division of application No. 11/415,455, filed on May 1, 2006, now Pat. No. 7,795,282.

(60) Provisional application No. 60/676,890, filed on May 2, 2005.

(51) Int. Cl.

| C07D 417/04 | (2006.01) |
| C07D 417/14 | (2006.01) |
| C07D 285/12 | (2006.01) |
| C07D 471/04 | (2006.01) |
| C07D 419/04 | (2006.01) |
| C07D 487/04 | (2006.01) |
| C07D 513/04 | (2006.01) |
| C07D 495/04 | (2006.01) |
| C07F 9/6539 | (2006.01) |
| C07D 497/04 | (2006.01) |

(52) U.S. Cl.
CPC ............ *C07D 513/04* (2013.01); *C07D 285/12* (2013.01); *C07D 417/04* (2013.01); *C07D 417/14* (2013.01); *C07D 419/04* (2013.01); *C07D 471/04* (2013.01); *C07D 487/04* (2013.01); *C07D 495/04* (2013.01); *C07D 497/04* (2013.01); *C07F 9/65395* (2013.01)

(58) Field of Classification Search
CPC .. C07D 417/04; C07D 417/14; C07D 285/12; C07D 471/04; C07D 419/04; C07D 487/04; C07D 513/04
See application file for complete search history.

(56) References Cited

U.S. PATENT DOCUMENTS

| 2,702,803 | A  | 2/1955  | Ainsworth |
| 4,782,072 | A  | 11/1988 | Stillings |
| 4,927,822 | A  | 5/1990  | Brown et al. |
| 5,668,159 | A  | 9/1997  | Jin et al. |
| 5,958,957 | A  | 9/1999  | Andersen et al. |
| 5,972,937 | A  | 10/1999 | Gaster et al. |
| 5,972,978 | A  | 10/1999 | Andersen et al. |
| 6,159,938 | A  | 12/2000 | Gyorkos et al. |
| 6,235,762 | B1 | 5/2001  | Takasugi et al. |
| 7,115,642 | B2 | 10/2006 | Singh et al. |
| 7,220,745 | B2 | 5/2007  | Singh et al. |
| 7,326,790 | B2 | 2/2008  | Singh et al. |
| 7,425,636 | B2 | 9/2008  | Murakata et al. |
| 7,449,486 | B2 | 11/2008 | Hans et al. |
| 7,521,447 | B2 | 4/2009  | Munson et al. |
| 7,795,282 | B2 | 9/2010  | Hans et al. |
| 7,956,073 | B2 | 6/2011  | Hans et al. |
| 8,236,825 | B2 | 8/2012  | Hans et al. |
| 8,268,871 | B2 * | 9/2012 | Hans et al. ................... 514/363 |
| 8,324,257 | B2 | 12/2012 | Ahrendt |

(Continued)

FOREIGN PATENT DOCUMENTS

| EP | 0531906 A1 | 3/1993 |
| EP | 1004241 A1 | 5/2000 |

(Continued)

OTHER PUBLICATIONS

Askari et al., *Journal of the Chemical Society, Perkin Transactions 1: Organic and Bio-Organic Chemistry*, (1972-1999)(2), 360-365 (1981).

(Continued)

*Primary Examiner* — Rebecca Anderson

(74) *Attorney, Agent, or Firm* — Viksnins Harris & Padys PLLP; Corey M. Williams

(57) ABSTRACT

This invention relates to inhibitors of mitotic kinesins, particularly KSP, and methods for producing these inhibitors. The invention also provides pharmaceutical compositions comprising the inhibitors of the invention and methods of utilizing the inhibitors and pharmaceutical compositions in the treatment and prevention of various disorders.

19 Claims, No Drawings

(56) References Cited

U.S. PATENT DOCUMENTS

| | | | |
|---|---|---|---|
| 8,580,828 | B2 | 11/2013 | Hans et al. |
| 8,623,895 | B2 | 1/2014 | Hans et al. |
| 2002/0002193 | A1 | 1/2002 | Yu et al. |
| 2003/0229054 | A1 | 12/2003 | Belliotti et al. |
| 2004/0142985 | A1 | 7/2004 | Singh et al. |
| 2004/0167188 | A1 | 8/2004 | Xin et al. |
| 2004/0248950 | A1 | 12/2004 | Ishizuka et al. |
| 2004/0254227 | A1 | 12/2004 | Singh et al. |
| 2004/0266840 | A1 | 12/2004 | Singh et al. |
| 2005/0004186 | A1 | 1/2005 | Barrett et al. |
| 2005/0009877 | A1 | 1/2005 | Lu |
| 2005/0070538 | A1 | 3/2005 | Cheng et al. |
| 2005/0075375 | A1 | 4/2005 | Vourloumis et al. |
| 2005/0119484 | A1 | 6/2005 | Breslin et al. |
| 2007/0112044 | A1 | 5/2007 | Murakata et al. |
| 2007/0155804 | A1 | 7/2007 | Murakata et al. |
| 2007/0276017 | A1 | 11/2007 | Murakata et al. |
| 2008/0153887 | A1 | 6/2008 | Cox et al. |
| 2012/0270803 | A1 | 10/2012 | Hans et al. |
| 2014/0018399 | A1 | 1/2014 | Hans et al. |
| 2014/0094603 | A1 | 4/2014 | Hans et al. |

FOREIGN PATENT DOCUMENTS

| | | |
|---|---|---|
| EP | 1671957 A1 | 6/2006 |
| JP | 2005-232016 | 9/2005 |
| WO | WO 93/22311 A1 | 11/1993 |
| WO | WO 98/38177 A1 | 9/1998 |
| WO | WO 01/56994 A1 | 8/2001 |
| WO | WO 03/051854 A1 | 6/2003 |
| WO | WO 03/079973 A2 | 10/2003 |
| WO | WO 2004/092147 A1 | 10/2004 |
| WO | WO 2004/111023 A1 | 12/2004 |
| WO | WO 2004/111024 A1 | 12/2004 |
| WO | WO 2005/017190 A2 | 2/2005 |
| WO | WO 2005/035512 A1 | 4/2005 |
| WO | WO 2005/092304 A2 | 10/2005 |
| WO | WO 2006/031348 A2 | 3/2006 |
| WO | WO 2006/044825 A2 | 4/2006 |
| WO | WO 2008/042982 A2 | 4/2008 |

OTHER PUBLICATIONS

Bolshaya Sovetskaya Entsiklopediya [The Big Soviet Enclyclopedia], M., vol. 25, p. 891 (1976).

Bryn et al., "Chapter 11: Hydrates and Solvates" *Solid-State Chemistry of Drugs, Second Edition*, pp. 233-247, (1999).

Golub et al., "Molecular Classification Prediction by Gene Expression of Cancer: Class Discovery and Class Monitoring", *Science, vol. 286*, 531-537, (1999).

Lala et al., "Role of Nitric Oxide in Tumor Progression: Lessons from Experimental Tumors" *Cancer and Metastasis Reviews*, 17(1), pp. 91-106, (1998).

Patent Cooperation Treaty International Search Report and Written Opinion of the International Searching Authority, PCT/US06/16526, 10 pages, Sep. 21, 2006.

Moss, S. F. et al., "Thiadiazoles and Thiadiazolines. Part 3.[1] Synthesis of Triazol-3-yl-$\Delta^2$-1,3,4-thiadiazolines and a New Synthesis of Unsymmetrical 2, 5-Di-substituted 1,3,4-Thiadiazoles", *J. Chem. Soc. Perkin Trans, I*, pp. 1987-1991, (1982).

Moss, S. F. et al., "Thiadiazoles and Thiadiazolines. Part 4.[1] Acetylation, Hyrdrolysis, and Cyclocondensations of $\Delta^2$-1,3,4-Thiadiazolines-α-carboxamides", *J. Chem. Soc. Perkin Trans, I*, pp. 1993-1998, (1982).

N.A. Tyukavkina, Yu. I. Baukov, Bioorganicheskaya khimiya [Bioorganic Chemistry], M., Meditsina, 54 (1991).

S.L. Polyakova (Patent Examiner), Office Action and translation thereof from Russian Application No. 2007144612/04(048882), 11 pages, received Feb. 11, 2010.

Szczepankiewicz et al., "New Antimitotic Agents with Activity in Multi-Drug Resistant Cell Lines and in Vivo Efficacy in Murine Tumor Models", *Journal of Medicinal Chemistry*, 44(25), 4416-4430 (2001).

Examination Report Corresponding to Related Taiwanese Patent Application No. 094136480 received Jan. 5, 2012.

Examination Report Corresponding to Related Taiwanese Patent Application No. 095115570 received Jan. 5, 2012.

Extended European Search Report Corresponding to Related European Application No. 05819172.7 dated Sep. 18, 2009.

First Office Action Corresponding to Related Chinese Patent Application No. 200580043628.9 dated Jun. 5, 2009.

Office Action Corresponding to Related Chinese Patent Application No. 200680024228.8, dated Mar. 1, 2010.

Office Action Corresponding to Related Chinese Patent Application No. 200680024228.8, dated Sep. 9, 2010.

International Search Report Corresponding to Related PCT Application No. PCT/US2005/37305 dated Jul. 14, 2006.

International Search Report for Related PCT Application U.S. Appl. No. PCT/US2007/08246 dated Apr. 9, 2008.

Notice of Reasons for Rejection Corresponding to Related Japanese Patent Application No. 2007-537010 dated Aug. 5, 2011.

Office Action Corresponding to Related Japanese Patent Application No. 2008-510090, dated Nov. 18, 2011.

Office Action Corresponding to Related Canadian Patent Application No. 2,606,708, dated Dec. 10, 2012.

Office Action Corresponding to Related Columbian Patent Application No. 07-126.692, received Sep. 22, 2011.

Office Action Corresponding to Related Indian Patent Application No. 4629/KOLNP/2007, dated Mar. 13, 2013.

Written Opinion Corresponding to Related Singapore Patent Application No. 200717335-4, received Sep. 15, 2009.

Office Action Corresponding to Related Korean Patent Application No. 10-2007-7027972, dated Jan. 29, 2013.

Office Action Corresponding to Related Ukrainian Patent Application No. a 2007 13355, received Feb. 3, 2011.

* cited by examiner

MITOTIC KINESIN INHIBITORS AND METHODS OF USE THEREOF

CROSS-REFERENCE TO RELATED APPLICATION

This application is a Continuation application of U.S. Ser. No. 14/031,958, filed Sep. 19, 2013, which is a Divisional application of U.S. Ser. No. 13/586,355, filed Aug. 15, 2012, now U.S. Pat. No. 8,580,828, which is a Divisional application of U.S. Ser. No. 12/822,066, filed Jun. 23, 2010, now U.S. Pat. No. 8,268,871, which is a Divisional application of U.S. Ser. No. 11/415,455, filed May 1, 2006, now U.S. Pat. No. 7,795,282, and claims priority to U.S. Provisional Application Ser. No. 60/676,890, filed May 2, 2005, which are incorporated herein by reference in their entirety.

BACKGROUND OF THE INVENTION

1. Field of the Invention

This invention relates to novel inhibitors of mitotic kinesins, in particular the mitotic kinesin KSP, and pharmaceutical compositions containing the inhibitors. The compounds of this invention are useful for the treatment of cellular proliferative diseases, for example cancer, hyperplasias, restenosis, cardiac hypertrophy, immune disorders, fungal infections and inflammation. This invention also provides methods for preparing these inhibitors.

2. Description of the State of the Art

Among the therapeutic agents used to treat cancer are the taxanes and vinca alkaloids, which act on microtubules. Microtubules are the primary structural elements of the mitotic spindle, which is responsible for distribution of replicate copies of the genome to each of the two daughter cells that result from cell division. It is presumed that disruption of the mitotic spindle by these drugs results in inhibition of cancer cell division and induction of cancer cell death. However, microtubules form other types of cellular structures, including tracks for intracellular transport in nerve processes. Because drugs such as taxanes and vinca alkaloids do not specifically target mitotic spindles, they have side effects that limit their usefulness.

Improvements in the specificity of agents used to treat cancer is of considerable interest, in part because of the improved therapeutic benefits which would be realized if the side effects associated with administration of these agents could be reduced.

Traditionally, dramatic improvements in the treatment of cancer have been associated with identification of therapeutic agents acting through novel mechanisms. Examples include not only the taxanes, but also the camptothecin class of topoisomerase I inhibitors. From both of these perspectives, mitotic kinesins are attractive targets for new anti-cancer agents.

Mitotic kinesins are enzymes essential for assembly and function of the mitotic spindle, but are not generally part of other microtubule structures such as nerve processes. Mitotic kinesins play essential roles during all phases of mitosis. These enzymes are "molecular motors" that transform energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death.

Among the identified mitotic kinesins is kinesin spindle protein (KSP). KSP belongs to an evolutionarily conserved kinesin subfamily of plus end-directed microtubule motors that assemble into bipolar homotetramers consisting of antiparallel homodimers. During mitosis, KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other non-human organisms bundle antiparallel microtubules and slide them relative to one another, thus forcing the spindle poles apart. KSP may also mediate in anaphase B spindle elongation and focusing of microtubules at the spindle pole.

Human KSP or HsEg5 has been described (Blangy, et al., *Cell*, 83:1159-69 (1995); Whitehead, et al., *Arthritis Rheum.*, 39:1635-42 (1996); Galtio, et al., *J. Cell Biol.*, 135:339-414 (1996); Blangy, et al., *J. Bio. Chem.*, 272:19418-24 (1997); Blangy, et al., *Cell Motil Cytoskeleton*, 40:174-82 (1998); Whitehead and Rattner, *J. Cell Sci.*, 111:2551-61 (1998); Kaiser, et al., *JBC* 274:18925-31 (1999); GenBank accession numbers: X85137, NM004523 and U37426), and a fragment of the KP gene (TRIPS) has been described (Lee, et al., *Mol. Endocrinol.*, 9:243-54 (1995); GenBank accession number L40372). *Xenopus* KSP homologs (Eg5), as well as *Drosophilia* K-LP61 F/KRP 130 have been reported.

Small molecule inhibitors of KSP have recently been described in WO 03/079,973 and WO 2005/035512.

Mitotic kinesins are therefore attractive targets for the discovery and development of novel mitotic chemotherapeutics.

SUMMARY OF THE INVENTION

This invention provides novel compounds that inhibit mitotic kinesins, in particular the mitotic kinesin KSP. The compounds of this invention have utility as therapeutic agents for diseases that can be treated by the inhibition of the assembly and function of microtubule structures, including the mitotic spindle.

In general, the invention relates to kinesin inhibitors of the general Formula I:

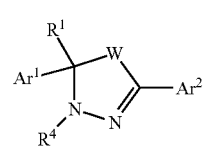

I and metabolites, solvates, tautomers, and pharmaceutically acceptable salts and prodrugs thereof, wherein W, $Ar^1$, $Ar^2$, $R^1$ and $R^4$ are as defined below.

In a further aspect the present invention provides methods of modulating mitotic spindle formation, which comprises administering to a warm-blooded animal an effective amount of a compound of Formula I, or a solvate, pharmaceutically acceptable salt or pharmaceutically acceptable prodrug thereof.

In a further aspect the present invention provides a method of treating abnormal cell growth conditions in a human or animal, which comprises administering to a warm-blooded animal an effective amount of a compound of Formula I, or a solvate, pharmaceutically acceptable salt or pharmaceutically acceptable prodrug thereof.

In a further aspect the present invention provides a method of inhibiting abnormal cell growth, which comprises administering to said abnormal cells an effective amount of a compound of Formula I, or a solvate, pharmaceutically acceptable salt or pharmaceutically acceptable prodrug thereof.

In a further aspect the present invention provides a method of providing a mitotic kinesin inhibitory effect in a human or animal, comprising administering to said human or animal an effective amount of a compound of Formula I, or a solvate, pharmaceutically acceptable salt or pharmaceutically acceptable prodrug thereof.

In a further aspect the present invention provides methods of treating or preventing a microtubule-mediated condition in a human or animal, comprising administering to a human or animal in need thereof a compound of Formula I or a solvate, pharmaceutically acceptable salt or pharmaceutically acceptable prodrug thereof, in an amount effective to treat or prevent said microtubule-mediated condition. Microtubule-mediated conditions that can be treated or prevented according to the methods of this invention include, but are not limited to, cellular proliferative diseases, for example cancer, hyperplasias, restenosis, cardiac hypertrophy, immune disorders, infectious disease, fungal or other eukaryote infections, and inflammatory disease.

The compounds of the present invention may be used advantageously in combination with other known therapeutic agents.

The invention also relates to pharmaceutical compositions comprising a compound of Formula I or a solvate, pharmaceutically acceptable prodrug or pharmaceutically acceptable salt thereof, alone or in combination with a second therapeutic agent.

This invention also provides compounds of Formula I for use in therapy.

An additional aspect of the invention is the use of a compound of Formula I for the preparation of a medicament for use as a kinesin inhibitor.

This invention further provides kits comprising compounds of Formula I.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF THE INVENTION

The compounds of Formula I are useful for inhibiting mitotic kinesins and microtubule-mediated events such as mitotic spindle production. Such compounds have utility for treating or inhibiting a microtubule-mediated condition in a human or animal.

In general, the invention relates to compounds of the general Formula I:

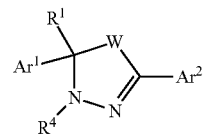

and metabolites, solvates, tautomers, salts and pharmaceutically acceptable salts and prodrugs thereof, wherein:

W is $S(O)_m$;

m is 0, 1 or 2;

$R^1$ is H, alkyl, cycloalkyl, heteroalkyl, alkenyl or alkynyl, wherein said alkyl, cycloalkyl, heteroalkyl, alkenyl and alkynyl are optionally substituted with one or more groups independently selected from oxo, halogen, cyano, nitro, azido, —$OR^{10}$, —$NR^{10}R^{11}$, —$NR^{10}SO_2R^{13}$, —$C(=O)R^{10}$, —$OC(=O)R^{10}$, —$C(=O)OR^{10}$, —$C(=O)NR^{10}R^{11}$, —$NR^{10}C(O)OR^{13}$, —$NR^{10}C(=O)(CH_2)_{0-2}R^{11}$, —$SR^{10}$, —$S(O)R^{13}$, —$SO_2R^{13}$, —$SO_2NHC(=O)R^{10}$, —$NR^{10}C(O)NR^{11}R^{12}$, alkyl, cycloalkyl, alkenyl, alkynyl, aryl, arylalkyl, heterocyclyl, heterocyclylalkyl, —$OP(=O)(OR^{10})_2$, an amino acid residue, a dipeptide, a tripeptide, or —$NR^{10}CR^{22}R^{23}NR^{11}R^{12}$, with the proviso that said alkyl does not terminate with a —$C(=O)OR^{10}$ group, or $R^1$ is Z—$NR^{17}$—$C(=NR^{18})R^{19}$, Z—$NR^{17}$—$C(=NR^{18})NR^{20}R^{21}$, Z—$C(=NR^{18})NR^{20}R^{21}$, Z—O—$NR^{17}C(=NR^{18})NR^{20}R^{21}$, Z—O—$NR^{17}$—$C(=NR^{18})R^{20}$, Z—$NR^{22}$—$NR^{23}$—$C(=NR^{18})R^{19}$, or Z—$NR^{22}NR^{23}$—$C(=NR^{18})NR^{20}R^{21}$, wherein Z is alkylene optionally substituted with one or more halogen;

$Ar^1$ and $Ar^2$ are independently phenyl or a 5 or 6 membered heteroaryl ring having 1 to 3 heteroatoms independently selected from N, O and S, wherein said heteroaryl is a carbon radical and said phenyl and heteroaryl are optionally substituted with one or more groups independently selected from halogen, cyano, nitro, trifluoromethyl, difluoromethoxy, trifluoromethoxy, azido, —$OR^{10}$, —$NR^{10}R^{11}$, —$NR^{10}SO_2R^{13}$, —$SO_2NR^{10}R^{11}$, —$C(=O)R^{10}$, —$C(=O)OR^{10}$, —$OC(=O)R^{10}$, —$NR^{10}C(=O)OR^{13}$, —$NR^{10}C(=O)R^{11}$, —$C(=O)NR^{10}R^{11}$, —$SR^{10}$, —$S(O)R^{13}$, $SO_2R^{13}$, —$SO_2NHC(=O)R^{10}$, —$NR^{10}C(=O)NR^{11}R^{12}$, —$NR^{10}C(NCN)NR^{11}R^{12}$, —$NR^{10}C(H)NR^{11}R^{12}$, —$NR^{10}C(R^{13})NR^{11}R^{12}$, —$OP(=O)(OR^{10})_2$, alkyl, cycloalkyl, alkenyl, alkynyl, aryl, heteroaryl, arylalkyl, heteroarylalkyl, heterocyclyl and heterocyclylalkyl;

$R^4$ is a partially unsaturated or fully unsaturated 5 membered heterocyclic ring comprising 1-4 heteroatoms independently selected from N, O or S, or $R^4$ is a partially unsaturated or fully unsaturated 6 membered heterocyclic ring comprising 1-4 heteroatoms independently selected from N, O or S, or $R^4$ is a partially unsaturated or fully unsaturated 7-12 membered bicyclic heterocyclic ring comprising two or more heteroatoms independently selected from N, O or S, wherein $R^4$ is bonded to the ring nitrogen of Formula I through an unsaturated carbon bond and $R^4$ is optionally substituted with one or more groups independently selected from oxo (provided it is not on a nitrogen, oxygen or an unsaturated carbon), halogen, cyano, nitro, trifluoromethyl, difluoromethyl, fluoromethyl, difluoromethoxy, trifluoromethoxy, azido, —$NR^{10}R^{11}$, —$NR^{10}SO_2R^{13}$, —$SO_2NR^{10}R^{11}$, —$C(=O)R^{10}$, —$C(O)OR^{10}$, —$OC(=O)R^{10}$, —$NR^{10}C(=O)OR^{13}$, —$NR^{10}C(=O)R^{11}$, —$C(=O)NR^{10}R^{11}$, —$SR^{10}$, —$S(O)R^{13}$, —$SO_2R^{13}$, $SO_2NHC(=O)R^{10}$, —$NR^{10}C(=O)NR^{11}(OR^{12})$, —$NR^{10}C(=O)NR^{11}R^{12}$, —NR$^{10}$C(NCN)NR$^{11}$R$^{12}$, —NR$^{10}$C(H)NR$^{11}$R$^{12}$, —NR$^{10}$C(R$^{13}$)NR$^{11}$R$^{12}$, —OR$^{10}$, alkyl, cycloalkyl, alkenyl, alkynyl, heteroalkyl, aryl, heteroaryl, arylalkyl, heteroarylalkyl, heterocyclyl, heterocyclylalkyl, —OP(=O)(OR$^{10}$)$_2$, an amino acid residue, a dipeptide and a tripeptide, wherein said alkyl, cycloalkyl, alkenyl, alkynyl, aryl, heteroaryl, arylalkyl, heteroarylalkyl, heterocyclyl and heterocyclylalkyl are optionally substituted with one or more groups independently selected from oxo (with the proviso that it is not on said aryl or heteroaryl portions), halogen, cyano, nitro, hydroxy, —OR$^{10}$, NR$^{10}$R$^{11}$, trifluoromethyl, difluoromethoxy, trifluoromethoxy, azido, —NR$^{10}$SO$_2$R$^{13}$, —SO$_2$NR$^{10}$R$^{11}$, —C(=O)R$^{10}$, —C(=O)OR$^{10}$, —OC(=O)R$^{10}$, —NR$^{10}$C(=O)OR$^{11}$, —NR$^{10}$C(=O)R$^{11}$, —C(=O)NR$^{10}$R$^{11}$, —SR$^{10}$, —S(O)R$^{13}$, —SO$_2$R$^{13}$, SO$_2$NHC(=O)R$^{10}$, —NR$^{10}$C(=O)NR$^{11}$R$^{12}$, —NR$^{10}$C(NCN)NR$^{11}$R$^{12}$, alkyl, cycloalkyl, aryl, heteroaryl, arylalkyl, heteroarylalkyl, heterocyclyl, and heterocyclylalkyl;

R$^{10}$, R$^{11}$ and R$^{12}$ independently are selected from hydrogen, alkyl, trifluoromethyl, alkenyl, alkynyl, cycloalkyl, aryl, heteroaryl, heterocyclyl and arylalkyl, wherein said alkyl, alkenyl, alkynyl, cycloalkyl, aryl, heteroaryl, heterocyclyl and arylalkyl are optionally substituted with one or more groups independently selected from oxo (with the proviso that it is not on said aryl or heteroaryl portions), halogen, cyano, nitro, OR$^{14}$, —NR$^{14}$R$^{15}$, trifluoromethyl, difluoromethoxy, trifluoromethoxy, azido, alkyl, cycloalkyl, aryl, heteroaryl, arylalkyl, heteroarylalkyl, heterocyclyl, and heterocyclylalkyl;

R$^{13}$ is alkyl, alkenyl, cycloalkyl, aryl, heteroaryl, heterocyclyl or arylalkyl, wherein said alkyl, alkenyl, cycloalkyl, aryl, heteroaryl, heterocyclyl and arylalkyl are optionally substituted with one to three groups independently selected from oxo (with the proviso that it is not on said aryl or heteroaryl portions), halogen, cyano, nitro, OR$^{14}$, —NR$^{14}$R$^{15}$, trifluoromethyl, difluoromethoxy, trifluoromethoxy, azido, alkyl, cycloalkyl, aryl, heteroaryl, arylalkyl, heteroarylalkyl, heterocyclyl, and heterocyclylalkyl, or any two of R$^{10}$, R$^{11}$, R$^{12}$ and R$^{13}$ together with the atoms to which they are attached form a 4 to 10 membered heteroaryl or heterocyclic ring, wherein said heteroaryl and heterocyclic rings are optionally substituted with one to three groups independently selected from oxo (with the proviso that it is not on said heteroaryl ring), halogen, cyano, nitro, OR$^{14}$, —NR$^{14}$R$^{15}$, trifluoromethyl, difluoromethoxy, trifluoromethoxy, azido, alkyl, cycloalkyl, aryl, heteroaryl, arylalkyl, heteroarylalkyl, heterocyclyl, and heterocyclylalkyl;

R$^{14}$ and R$^{15}$ are independently selected from hydrogen, alkyl, alkenyl, lower alkynyl, cycloalkyl, aryl, heteroaryl, heterocyclyl and arylalkyl, or R$^{14}$ and R$^{15}$ together with the atoms to which they are attached form a saturated, partially unsaturated or fully unsaturated 5-6 membered heterocyclyl;

R$^{17}$, R$^{22}$ and R$^{23}$ are independently H or alkyl;

R$^{18}$ is H, OH, O-alkyl, CN, C(=O)NH$_2$, C(=O)NH(alkyl), C(=O)N(alkyl)$_2$, C(=O)alkyl, or alkyl optionally substituted with one or more groups independently selected from halogen, CN, OH, O-alkyl, NH$_2$, NH-alkyl, N(alkyl)$_2$ and aryl;

R$^{19}$ is H or alkyl optionally substituted with one or more groups independently selected from halogen, NO$_2$, halogen, CN, OH, O-alkyl, NH$_2$, NH-alkyl, N(alkyl)$_2$ and aryl; and R$^{20}$ and R$^{21}$ are independently H, C(=O)alkyl, or alkyl optionally substituted with one or more groups independently selected from halogen, CN, OH, O-alkyl, NH$_2$, NH-alkyl, N(alkyl)$_2$ and aryl, or R$^{20}$ and R$^{21}$ together with the atoms to which they are attached form a 5-6 membered unsaturated or partially unsaturated heterocyclic ring;

or R$^{18}$ and R$^{20}$ together with the atoms to which they are attached form a 5-6 membered partially unsaturated or fully unsaturated heterocyclic ring;

or R$^{17}$ and R$^{20}$ together with the atoms to which they are attached form a 5-6 membered unsaturated or partially unsaturated heterocyclic ring.

In another embodiment there is provided a compound of Formula I

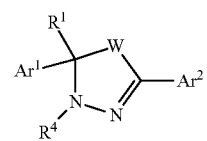

and metabolites, solvates, tautomers, and pharmaceutically acceptable salts and prodrugs thereof, wherein:

W is S(O)$_m$;

m is 0, 1 or 2;

R$^1$ is H, alkyl, cycloalkyl, heteroalkyl, alkenyl or alkynyl, wherein said alkyl, cycloalkyl, heteroalkyl, alkenyl and alkynyl are optionally substituted with one or more groups independently selected from oxo, halogen, cyano, nitro, trifluoromethyl, difluoromethoxy, trifluoromethoxy, azido, —OR$^{10}$, —NR$^{10}$R$^{11}$, NR$^{10}$SO$_2$R$^{13}$, —C(O)R$^{10}$, —OC(=O)R$^{10}$, —C(=O)OR$^{10}$, —C(=O)NR$^{10}$R$^{11}$, —NR$^{10}$C(O)OR$^{13}$, —NR$^{10}$C(O)R$^{11}$, —SR$^{10}$, —S(O)R$^{13}$, —SO$_2$R$^{13}$, —SO$_2$NHC(=O)R$^{10}$, —NR$^{10}$C(=O)NR$^{11}$R$^{12}$, —NR$^{10}$C(NCN)NR$^{11}$R$^{12}$, alkyl, cycloalkyl, alkenyl, alkynyl, aryl, arylalkyl, heterocyclyl, heterocyclylalkyl, —OP(=O)(OR$^{10}$)$_2$, an amino acid residue, a dipeptide and a tripeptide, with the proviso that said alkyl does not terminate with a —C(=O)OR$^{10}$ group;

Ar$^1$ and Ar$^2$ are independently phenyl or a 5 or 6 membered heteroaryl ring having 1 to 3 heteroatoms independently selected from N, O or S, wherein said heteroaryl is a carbon radical and wherein said phenyl and heteroaryl are optionally substituted with one or more groups independently selected from halogen, cyano, nitro, trifluoromethyl, difluoromethoxy, trifluoromethoxy, azido, —OR$^{10}$, —NR$^{10}$R$^{11}$, —NR$^{10}$SO$_2$R$^{13}$, SO$_2$NR$^{10}$R$^{11}$, —C(=O)R$^{10}$, —C(O)OR$^{10}$, —OC(=O)R$^{10}$, —NR$^{10}$C(=O)OR$^{13}$, —NR$^{10}$C(=O)R$^{11}$, —C(=O)NR$^{10}$R$^{11}$, —SR$^{10}$, —S(O)R$^{13}$, —SO$_2$R$^{13}$, —SO$_2$NHC(=O)R$^{10}$, —NR$^{10}$C(=O)NR$^{11}$R$^{12}$, —NR$^{10}$C(NCN)NR$^{11}$R$^{12}$, alkyl, cycloalkyl, alkenyl, alkynyl, aryl, heteroaryl, arylalkyl, heteroarylalkyl, heterocyclyl and heterocyclylalkyl;

R$^4$ is

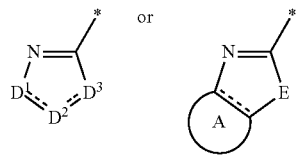

wherein a dashed line represents an optional double bond;

D$^1$ is N, NR$^6$, CR$^5$, CR$^5$R$^{5a}$, or C(=O);

D$^2$ is CR$^5$, CR$^5$R$^{5a}$, N or NR$^6$;

D$^3$ is S, O, N, NR$^6$ or CR$^5$R$^{5a}$;

E is O, S or NR$^6$;

A is a saturated, partially unsaturated, or fully unsaturated 5-8 carbocyclic ring or heterocyclic ring having 1 to 3 heteroatoms independently selected from N, O or S, wherein said carbocyclic and heterocyclic rings are optionally substituted with one or more groups independently selected from halogen, cyano, nitro, trifluoromethyl, difluoromethoxy, trifluoromethoxy, azido, oxo, —OR$^{10}$, —NR$^{10}$R$^{11}$, —NR$^{10}$SO$_2$R$^{13}$, SO$_2$NR$^{10}$R$^{11}$, —C(=O)R$^{10}$, —C(=O)OR$^{10}$, —OC(=O)R$^{10}$, —NR$^{10}$C(=O)OR$^{13}$, —NR$^{10}$C(=O)R$^{11}$, —C(=O)NR$^{10}$R$^{11}$, —SR$^{10}$, —S(O)R$^{13}$, —SO$_2$R$^{13}$, —SO$_2$NHC(=O)R$^{10}$—NR$^{10}$C(=O)NR$^{11}$R$^{12}$, —NR$^{10}$C(NCN)NR$^{11}$R$^{12}$, alkyl, cycloalkyl, alkenyl, alkynyl, aryl, heteroaryl, arylalkyl, heteroarylalkyl, heterocyclyl and heterocyclylalkyl, wherein said alkyl, cycloalkyl, alkenyl, alkynyl, aryl, heteroaryl, arylalkyl, heteroarylalkyl, heterocyclyl and heterocyclylalkyl are optionally substituted with one or more groups independently selected from oxo (with the proviso that it is not on said aryl or heteroaryl portions), halogen, cyano, nitro, hydroxy, —OR$^{10}$, NR$^{10}$R$^{11}$, trifluoromethyl, difluoromethoxy, trifluoromethoxy, azido, —NR$^{10}$SO$_2$R$^{13}$, —SO$_2$NR$^{10}$R$^{11}$, —C(=O)R$^{10}$, —C(=O)OR$^{10}$, —OC(=O)R$^{10}$, —NR$^{10}$C(=O)OR$^{11}$, —NR$^{10}$C(=O)R$^{11}$, —C(=O)NR$^{10}$R$^{11}$, —SR$^{10}$, —S(O)R$^{13}$, —SO$_2$R$^{13}$, SO$_2$NHC(=O)R$^{10}$, —NR$^{10}$C(=O)NR$^{11}$R$^{12}$, —NR$^{10}$C(NCN)NR$^{11}$R$^{12}$, alkyl, cycloalkyl, aryl, heteroaryl, arylalkyl, heteroarylalkyl, heterocyclyl and heterocyclylalkyl;

each R$^5$ and R$^{5a}$ is independently selected from H, halogen, cyano, nitro, trifluoromethyl, difluoromethoxy, trifluoromethoxy, azido, —NR$^{10}$R$^{11}$, —NR$^{10}$SO$_2$R$^{13}$, —SO$_2$NR$^{10}$R$^{11}$, —C(=O)R$^{10}$, —C(=O)OR$^{10}$, —OC(=O)R$^{10}$, —NR$^{10}$C(=O)OR$^{13}$, —NR$^{10}$C(=O)R$^{11}$, —C(=O)NR$^{10}$R$^{11}$, —SR$^{10}$, —S(O)R$^{13}$, —SO$_2$R$^{13}$, —SO$_2$NHC(=O)R$^{10}$, —NR$^{10}$C(=O)NR$^{11}$R$^{12}$, —NR$^{10}$C(NCN)NR$^{11}$R$^{12}$, —OR$^{10}$, alkyl, cycloalkyl, alkenyl, alkynyl, heteroalkyl, aryl, heteroaryl, arylalkyl, heteroarylalkyl, heterocyclyl and heterocyclylalkyl, wherein said alkyl, cycloalkyl, alkenyl, alkynyl, aryl, heteroaryl, arylalkyl, heteroarylalkyl, heterocyclyl and heterocyclylalkyl are optionally substituted with one or more groups independently selected from oxo (with the proviso that it is not on said aryl or heteroaryl portions), halogen, cyano, nitro, hydroxy, —OR$^{10}$, NR$^{10}$R$^{11}$, trifluoromethyl, difluoromethoxy, trifluoromethoxy, azido, —NR$^{10}$SO$_2$R$^{13}$, —SO$_2$NR$^{10}$R$^{11}$, —C(=O)R$^{10}$, —C(=O)OR$^{10}$, —OC(=O)R$^{10}$, —NR$^{10}$C(=O)OR$^{11}$, —NR$^{10}$C(=O)R$^{11}$, —C(=O)NR$^{10}$R$^{11}$, —SR$^{11}$, —S(O)R$^{13}$, —SO$_2$R$^{13}$, SO$_2$NHC(=O)R$^{10}$, —NR$^{10}$C(=O)NR$^{11}$R$^{12}$, —NR$^{10}$C(NCN)NR$^{11}$R$^{12}$, alkyl, cycloalkyl, aryl, heteroaryl, arylalkyl, heteroarylalkyl, heterocyclyl and heterocyclylalkyl;

R$^6$ is H, alkyl, cycloalkyl, alkenyl, alkynyl, aryl, heteroaryl or heterocyclyl, wherein said alkyl, cycloalkyl, alkenyl, alkynyl, aryl, heteroaryl and heterocyclyl are optionally substituted with one or more groups independently selected from oxo, halogen, cyano, nitro, hydroxy, —OR$^{10}$, NR$^{10}$R$^{11}$, trifluoromethyl, difluoromethoxy, trifluoromethoxy, azido, —NR$^{10}$SO$_2$R$^{13}$, —SO$_2$NR$^{10}$R$^{11}$, —C(=O)R$^{10}$, —C(=O)OR$^{11}$, —OC(=O)R$^{11}$, —NR$^{10}$C(=O)OR$^{11}$, —NR$^{10}$C(=O)R$^{11}$, —C(=O)NR$^{10}$R$^{11}$, —SR$^{10}$, —S(O)R$^{13}$, —SO$_2$R$^{13}$, —SO$_2$NHC(=O)R$^{10}$, —NR$^{10}$C(=O)NR$^{11}$R$^{12}$, —NR$^{10}$C(NCN)NR$^{11}$R$^{12}$, alkyl, cycloalkyl, aryl, heteroaryl, arylalkyl, heteroarylalkyl, heterocyclyl and heterocyclylalkyl;

R$^{10}$, R$^{11}$ and R$^{12}$ independently are selected from hydrogen, alkyl, trifluoromethyl, alkenyl, alkynyl, cycloalkyl, aryl, heteroaryl, heterocyclyl and arylalkyl, wherein said alkyl, alkenyl, alkynyl, cycloalkyl, aryl, heteroaryl, heterocyclyl and arylalkyl are optionally substituted with one or more groups independently selected from oxo (with the proviso that it is not on said aryl portions), halogen, cyano, nitro, OR$^{14}$, —NR$^{14}$R$^{15}$, trifluoromethyl, difluoromethoxy, trifluoromethoxy, azido, alkyl, cycloalkyl, aryl, heteroaryl, arylalkyl, heteroarylalkyl, heterocyclyl and heterocyclylalkyl;

R$^{13}$ is alkyl, alkenyl, cycloalkyl, aryl or arylalkyl, wherein said alkyl, alkenyl, cycloalkyl, aryl, heteroaryl, heterocyclyl and arylalkyl are optionally substituted with one to three groups independently selected from oxo (with the proviso that it is not on said aryl portions), halogen, cyano, nitro, OR$^{14}$, NR$^{14}$R$^{15}$, trifluoromethyl, difluoromethoxy, trifluoromethoxy, azido, alkyl, cycloalkyl, aryl, heteroaryl, arylalkyl, heteroarylalkyl, heterocyclyl and heterocyclylalkyl;

or any two of R$^{10}$, R$^{11}$, R$^{12}$ and R$^{13}$ together with the atoms to which they are attached form a 4 to 10 membered heteroaryl or heterocyclic ring, wherein said heteroaryl and heterocyclic rings are optionally substituted with one to three groups independently selected from oxo (with the proviso that it is not on said heteroaryl ring), halogen, cyano, nitro, OR$^{14}$, NR$^{14}$R$^{15}$, trifluoromethyl, difluoromethoxy, trifluoromethoxy, azido, alkyl, cycloalkyl, aryl, heteroaryl, arylalkyl, heteroarylalkyl, heterocyclyl and heterocyclylalkyl; and R$^{14}$ and R$^{15}$ are independently selected from hydrogen, alkyl, alkenyl, lower alkynyl, cycloalkyl, aryl, heteroaryl, heterocyclyl and arylalkyl.

In certain embodiments of Formula I, W is S.

According to another embodiment, R$^1$ is alkyl or heteroalkyl, wherein said alkyl and heteroalkyl are optionally substituted with one or more groups independently selected from —OR$^{10}$, —NR$^{10}$R$^{11}$, —OP(=O)(OR$^{10}$)$_2$, an amino acid residue, a dipeptide and a tripeptide. In another embodiment, there is provided a compound of Formula I, wherein R$^1$ is alkyl optionally substituted with NR$^{10}$C(=O)(CH$_2$)$_{0-2}$R$^{11}$, NR$^{10}$SO$_2$R$^{13}$, heterocyclyl, or R$^1$ is a heterocyclyl.

Exemplary embodiments include compounds of Formula I wherein R$^1$ is (CH$_2$)$_2$—OH, (CH$_2$)$_3$—OH, (CH$_2$)—NH$_2$, (CH$_2$)$_2$—NH$_2$, (CH$_2$)$_3$—NH$_2$, (CH$_2$)$_3$—NHCH(CH$_3$)$_2$, (CH$_2$)$_2$—NHMe, (CH$_2$)$_2$—NMe$_2$, (CH$_2$)$_3$—NMe$_2$, (CH$_2$)$_3$—NHMe, (CH$_2$)$_3$NHC(=O)Me, (CH$_2$)$_3$NHC(=O)CH(CH$_3$)$_2$, (CH$_2$)$_3$NHC(=O)CH$_2$CH$_2$NMe$_2$, (CH$_2$)$_3$NHSO$_2$Me, (CH$_2$)$_3$-(pyrrolidin-1-yl), (CH$_2$)$_3$-(piperidin-1-yl), (CH$_2$)$_3$-(4-methylpiperidin-1-yl), (CH$_2$)$_3$-(morpholin-4-yl), (CH$_2$)$_2$-(pyrrolidin-2-yl), (CH$_2$)$_3$NH(C=O)CH(Me)NH(C=O)CH(Me)NH$_2$, (CH$_2$)$_3$—OPO$_3$H$_2$, CH$_2$—O—CH$_2$OMe or piperidin-4-yl.

In particular embodiments, there is provided a compound of Formula I wherein R$^1$ is —(CH$_2$)$_3$NH$_2$.

In certain embodiments, R$^1$ is Z—NR$^{17}$—C(=NR$^{18}$)R$^{19}$, Z—NR$^{17}$—C(=NR$^{18}$)NR$^{20}$R$^{21}$, Z—C(=NR$^{18}$)NR$^{20}$R$^{21}$, Z—O—NR$^{17}$C(=NR$^1$)NR)NR$^{20}$R$^{21}$, Z—O—NR$^{17}$—C(=NR)R$^{20}$, Z—NR$^{22}$—NR$^{23}$—C(=NR$^{18}$)R$^{19}$, or Z—NR$^{22}$—NR$^{23}$—C(=NR$^{18}$)NR$^{20}$R$^{21}$.

In certain embodiments, there is provided a compound of Formula I wherein Ar$^1$ is phenyl optionally substituted with one or more groups independently selected from halogen, alkyl, —OR$^{10}$ or —NR$^{10}$R$^{11}$; or Ar$^1$ is a heteroaryl selected from thiophenyl or pyridyl, wherein said pyridyl is optionally substituted independently with one or more halogens.

Exemplary embodiments of such Ar$^1$ groups include phenyl, 2,4-difluorophenyl, 2-fluorophenyl, 3-fluorophenyl, 2-chlorophenyl, 3-chlorophenyl, 2,5-dichlorophenyl, 2,3-dichlorophenyl, 3,4-dichlorophenyl, 3,5-dichlorophenyl, 2-chloro-5-fluorophenyl, 2-fluoro-5-chlorophenyl, 2-chloro-5-methylphenyl, 2-trifluoromethyl-5-fluorophenyl, 2-fluoro-5-methoxyphenyl, thiophen-2-yl, thiophen-3-yl, 5-chlorothiophen-2-yl, 2-pyridyl, 3-pyridyl, 4-chloropyridin-3-yl, 3-chloropyridin-2-yl, 4-fluoropyridin-3-yl, or 3,6-difluoropyridin-2-yl.

In particular embodiments, $Ar^1$ is 2,4-difluorophenyl.

According to yet another embodiment, $Ar^2$ is an optionally substituted phenyl group. In certain embodiments, $Ar^2$ is substituted with one or more halogen groups. In a particular embodiment, $Ar^2$ is 2,4-difluorophenyl, 2,5-difluorophenyl, or 3-fluorophenyl. In other embodiments, $Ar^2$ is phenyl, 2-chlorophenyl, 4-chlorophenyl, 4-fluorophenyl, 4-bromophenyl or 3,4-dichlorophenyl.

In other embodiments, there is provided a compound of Formula I wherein $Ar^2$ is phenyl optionally substituted with one or more groups independently selected from $OR^{10}$, $NR^{10}R^{11}$, CN, $NO_2$, $-OP(=O)(OR^{10})_2$, $C(=O)OR^{10}$, or $Ar^2$ is a heteroaryl selected from pyridyl, thiophenyl optionally substituted with alkyl, imidazolyl, and pyrazolyl optionally substituted with $NR^{10}R^{11}$. For example, in certain embodiments, $Ar^2$ is 2-methylphenyl, 3-methylphenyl, 4-methylphenyl, 3,4-dimethylphenyl, 3,5-dimethylphenyl, 2-ethylphenyl, 3-ethylphenyl, 4-t-butylphenyl, 3-nitrophenyl, 3-hydroxyphenyl, 3-$(OPO_3H_2)$-phenyl, 3-aminophenyl, 3-carboxyphenyl, 3-cyanophenyl, 2-pyridyl, 3-pyridyl, 5-methylthiophen-2-yl, 2-methylthiazol-4-yl, 2-(1H-imidazol-2-yl), 2-(1H-imidazol-4-yl) or 3-amino-1H-pyrazol-5-yl.

In particular embodiments, $Ar^2$ is phenyl.

In certain embodiments, there is provided a compound of Formula I, wherein $R^4$ is selected from:

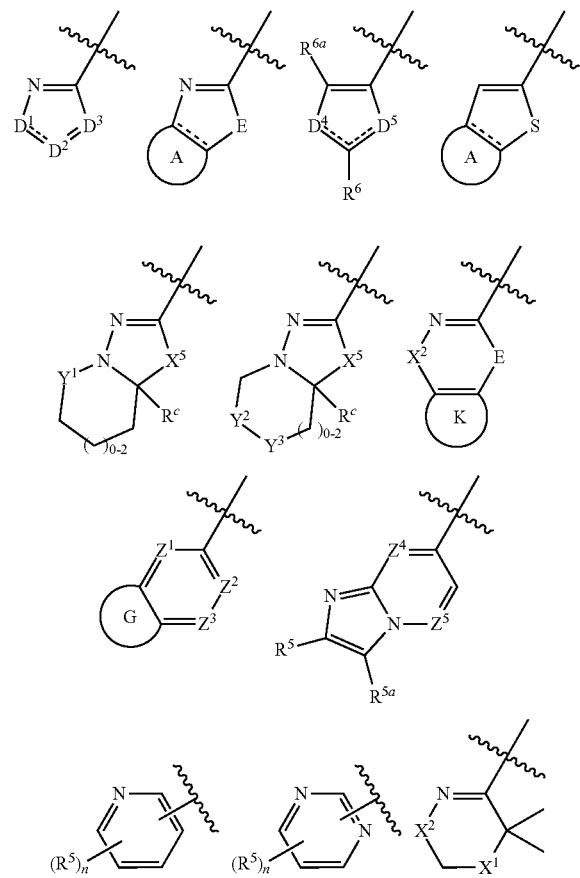

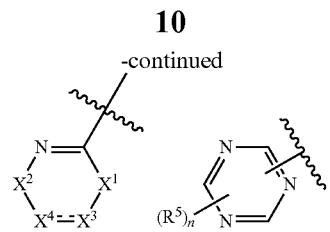

wherein:
a dashed line represents an optional double bond;
$D^1$ is N, $NR^6$, O, $CR^5$, $CR^5R^{5a}$, or $C(=O)$;
$D^2$ is $CR^5$, $CR^5R^{5a}$, N, $NR^6$, O, S or $C(=O)$, wherein only one of $D^1$ and $D^2$ is $C(=O)$;
$D^3$ is S, O, N, $NR^6$, $CR^5$ or $CR^5R^{5a}$;
$D^4$ and $D^5$ are independently N, $NR^6$, S or O;
E is O, S or $NR^6$;
$Y^1$ and $Y^2$ are $CH_2$, C=O or $SO_2$ wherein:
$Y^3$ is $CH_2$ or $NR^6$;
$X^1$ is O or S;
$X^2$ is C=O or $SO_2$;
$X^3$ and $X^4$ are independently $CH_2$ or $CMe_2$ when the bond represented by ---- is absent or $X^3$ and $X^4$ are independently CH or CMe when the bond represented by ---- is present;
$X^5$ is S, O, $NR^6$, SO, $SO_2$, or $CR^5CR^{5a}$
$Z^1$, $Z^2$, and $Z^3$ are independently N or $CR^5$, wherein 1 or 2 of $Z^1$, $Z^2$ and $Z^3$ is N;
one of $Z^4$ and $Z^5$ is N and the other is $CR^5$;
A is a saturated, partially unsaturated, or fully unsaturated 5-8 carbocyclic ring or heterocyclic ring having 1 to 3 ring heteroatoms independently selected from N, O, S, or $SO_2$, wherein said carbocyclic and heterocyclic rings are optionally substituted independently with one or more $R^7$ groups;
G is a saturated, or partially unsaturated, or fully unsaturated 5 membered heterocyclic ring having 1-3 ring heteroatoms independently selected from N S, O, SO and $SO_2$, wherein G is optionally substituted independently with one or more $R^7$ groups;
K is a benzene ring or a saturated or partially unsaturated 5-6 membered heterocyclic ring having 1-3 ring heteroatoms independently selected from N S, O, SO and $SO_2$, wherein K is optionally substituted with one or more $R^7$ groups;
each $R^5$ and $R^{5a}$ is independently selected from H, halogen, cyano, nitro, trifluoromethyl, difluoromethoxy, trifluoromethoxy, azido, $-NR^{10}R^{11}$, $-NR^{10}SO_2R^{13}$, $-SO_2NR^{10}R^{11}$, $-C(=O)R^{10}$, $-C(O)OR^{10}$, $-OC(=O)R^{10}$, $-NR^{10}C(=O)OR^{13}$, $-NR^{10}C(=O)R^{11}$, $-C(=O)NR^{10}R^{11}$, $-SR^{10}$, $-S(O)R^{13}$, $-SO_2R^{13}$, $SO_2NHC(=O)R^{10}$, $-NR^{10}C(=O)NR^{11}(OR^{12})$, $-NR^{10}C(=O)NR^{11}R^{12}$, $-NR^{10}C(NCN)NR^{11}R^{12}$, $-OR^{10}$, alkyl, cycloalkyl, alkenyl, alkynyl, heteroalkyl, aryl, heteroaryl, arylalkyl, heteroarylalkyl, heterocyclyl and heterocyclylalkyl, wherein said alkyl, cycloalkyl, alkenyl, alkynyl, aryl, heteroaryl, arylalkyl, heteroarylalkyl, heterocyclyl and heterocyclylalkyl are optionally substituted with one or more groups independently selected from oxo (with the proviso that it is not on said aryl or heteroaryl portions), halogen, cyano, nitro, hydroxy, $-OR^{10}$, $NR^{10}R^{11}$, trifluoromethyl, difluoromethoxy, trifluoromethoxy, azido, $-NR^{10}SO_2R^{13}$, $-SO_2NR^{10}R^{11}$, $-C(=O)R^{10}$, $-C(=O)OR^{10}$, $-OC(=O)R^1$, $-NR^{10}C(=O)OR^{11}$, $-NR^{10}C(=O)R^{11}$, $-C(=O)NR^{10}R^{11}$, $-SR^{10}$, $-S(O)R^{13}$, $-SO_2R^{13}$, $-SO_2NHC(=O)R^{10}$, $-NR^{10}C(=O)NR^{11}R^{12}$, $-NR^{10}C(NCN)NR^{11}R^{12}$, alkyl, cycloalkyl, aryl, heteroaryl, arylalkyl, heteroarylalkyl, heterocyclyl, and heterocyclylalkyl;
$R^6$ is H, alkyl, cycloalkyl, alkenyl, alkynyl, aryl, heteroaryl or heterocyclyl, wherein said alkyl, cycloalkyl, alkenyl, alkynyl, aryl, heteroaryl and heterocyclyl are optionally substituted with one or more groups independently selected from oxo, halogen, cyano, nitro, hydroxy, —OR$^{10}$, NR$^{10}$R$^{11}$, trifluoromethyl, difluoromethoxy, trifluoromethoxy, azido, —NR$^{10}$SO$_2$R$^{13}$, —SO$_2$NR$^{10}$R$^{11}$, —C(=O)R$^{10}$, —C(=O)OR$^{10}$, —OC(=O)R$^{10}$, —NR$^{10}$C(=O)OR$^{11}$, —NR$^{10}$C(=O)R$^{11}$, —C(=O)NR$^{10}$R$^{11}$, —SR$^{10}$, —S(O)R$^{13}$, —SO$_2$R$^{13}$, SO$_2$NHC(=O)R$^{10}$, —NR$^{10}$C(=O)NR$^{11}$R$^{12}$, —NR$^{10}$C(NCN)NR$^{11}$R$^{12}$, alkyl, cycloalkyl, aryl, heteroaryl, arylalkyl, heteroarylalkyl, heterocyclyl, and heterocyclylalkyl;

R$^{6a}$ is independently H or alkyl;

R$^7$ is halogen, cyano, nitro, trifluoromethyl, difluoromethoxy, trifluoromethoxy, azido, oxo (provided it is not on a nitrogen, oxygen or unsaturated carbon), —OR$^{10}$, —NR$^{10}$R$^{11}$, —NR$^{10}$SO$_2$R$^{13}$SO$_2$NR$^{10}$R$^{11}$, —C(=O)R$^{10}$, —C(=O)OR$^{10}$, —OC(=O)R$^{11}$, —NR$^{10}$C(=O)OR$^{13}$, —NR$^{10}$C(=O)R$^{11}$, —C(=O)NR$^{10}$R$^{11}$, —C(=O)NR$^{10}$R$^{11}$, —SR$^{10}$, —S(O)R$^{13}$, —SO$_2$R$^{13}$, —SO$_2$NHC(=O)R$^{10}$—NR$^{10}$C(=O)NR$^{11}$R$^{12}$, C(=NH)NH(CN), —NR$^{10}$C(NCN)NR$^{11}$R$^{12}$, alkyl, cycloalkyl, alkenyl, alkynyl, aryl, heteroaryl, arylalkyl, heteroarylalkyl, heterocyclyl and heterocyclylalkyl, wherein said alkyl, cycloalkyl, alkenyl, alkynyl, aryl, heteroaryl, arylalkyl, heteroarylalkyl, heterocyclyl and heterocyclylalkyl are optionally substituted with one or more groups independently selected from oxo (with the proviso that it is not on said aryl or heteroaryl portions), halogen, cyano, nitro, hydroxy, —OR$^{10}$, NR$^{10}$R$^{11}$, trifluoromethyl, difluoromethoxy, trifluoromethoxy, azido, —NR$^{10}$SO$_2$R$^{13}$, —SO$_2$NR$^{10}$R$^{11}$, —C(=O)R$^{10}$, —C(=O)OR$^{10}$, —OC(=O)R$^{10}$, —NR$^{10}$C(=O)OR$^{11}$, —NR$^{10}$C(=O)R$^{11}$, —C(=O)NR$^{10}$R$^{11}$, —SR$^{10}$, —S(O)R$^{13}$, —SO$_2$R$^{13}$, SO$_2$NHC(=O)R$^{11}$, —NR$^{10}$C(=O)NR$^{11}$R$^{12}$, NR$^{10}$C(=O)NR$^{10}$R$^{12}$, —NR$^{10}$C(NCN)NR$^{11}$R$^{12}$, OPO$_3$H, alkyl, cycloalkyl, aryl, heteroaryl, arylalkyl, heteroarylalkyl, heterocyclyl and heterocyclylalkyl;

R$^c$ is H or Me; and n is 0, 1 or 2.

Exemplary embodiments of R$^4$ include, but are not limited to, 2-thiazolyl, fused thiazolyl ring systems, 2-oxazolyl, fused oxazolyl ring systems, 2-imidazolyl, oxadiazolyl, thiadiazolyl, 4,5(H)-thiazolyl, 4-triazolyl, 4,5(H)-oxazolyl, fused 4,5(H)-thiazolyl ring systems, dihydropyrrol-2-on-yl, and substituted forms thereof, and shown as:

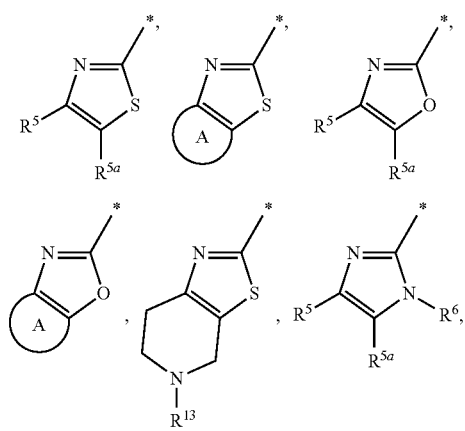

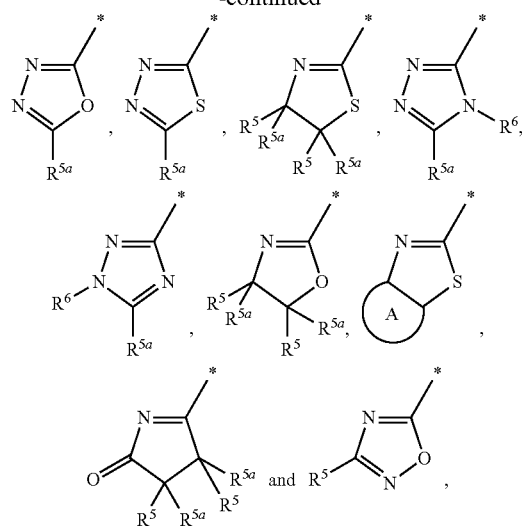

wherein the asterisk indicates the point of attachment, "A" is as defined above, and each R$^5$ and R$^{5a}$ is independent of every other R$^5$ and R$^{5a}$.

More specific embodiments of R$^4$ include

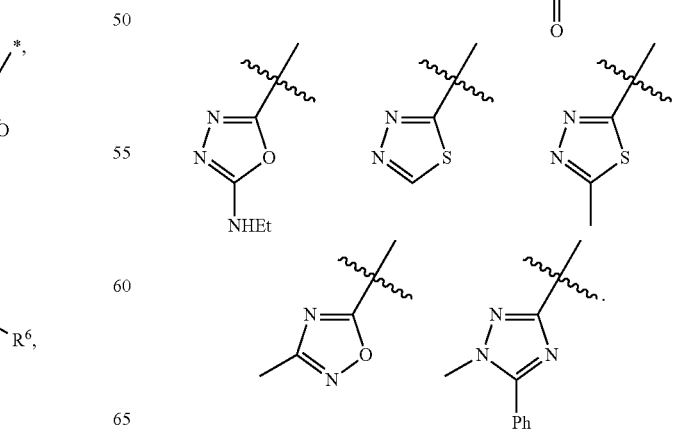

Further exemplary embodiments include compounds of Formula I wherein R⁴ is selected from

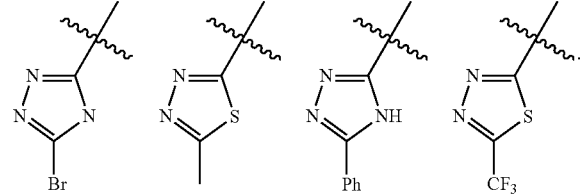

In certain embodiments, there is provided a compound of Formula I wherein R⁴ is selected from the structures

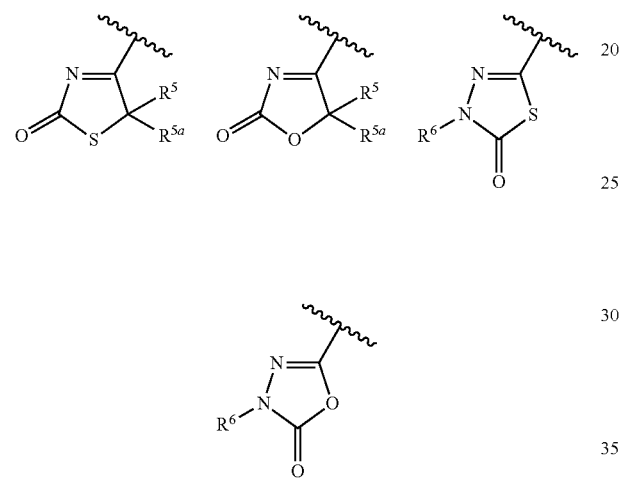

wherein $R^5$, $R^{5a}$ and $R^6$ are as defined for Formula I. In certain embodiments, $R^5$ and $R^{5a}$ are independently H, halogen, alkyl, aryl, or $NR^{10}R^{11}$, wherein said alkyl and aryl are optionally substituted with one or more groups independently selected from halogen and —C(=O)OR¹⁰.

In certain embodiments, there is provided a compound of Formula I wherein R⁴ is

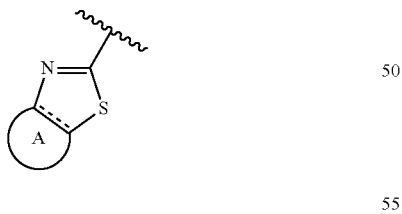

and A is a saturated or partially unsaturated heterocyclic ring having a ring nitrogen, wherein 1-2 carbon atoms of said heterocyclic ring are optionally substituted with a group independently selected from halogen or alkyl optionally substituted with one or more halogen, and the nitrogen of said heterocyclic ring is optionally substituted with C(=O)NR¹⁰R¹¹, C(=O)N(R¹⁰)OR¹¹, C(=NH)CH—CN, or alkyl optionally substituted with one or more groups independently selected from OR¹⁰, OPO₃H₂, NR¹⁰R¹¹ and heterocyclyl.

Exemplary embodiments include compounds of Formula I wherein R⁴ is selected from the structures:

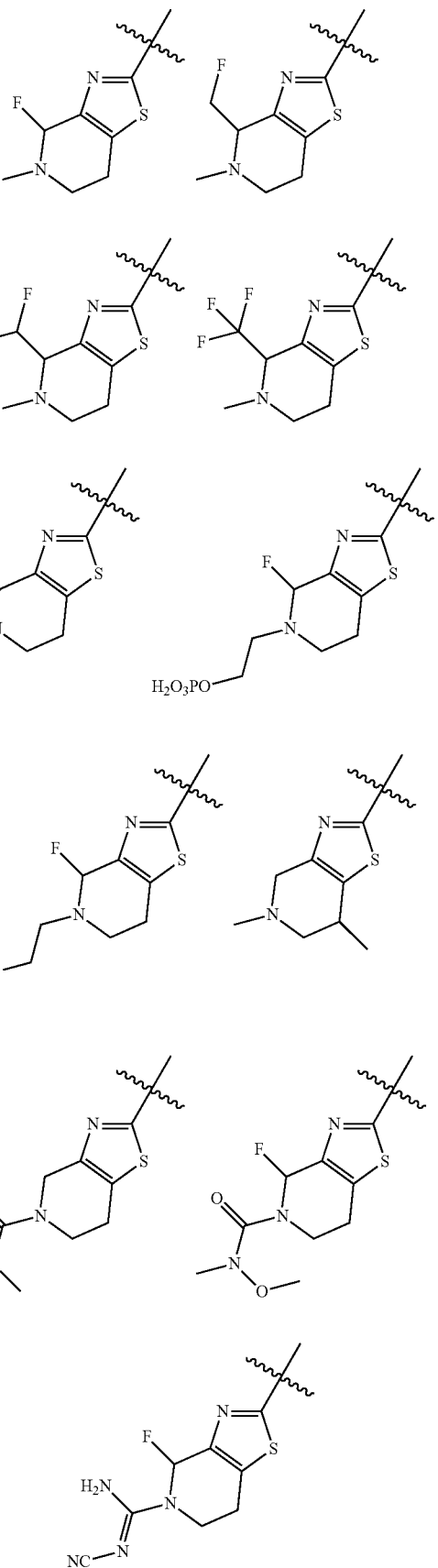

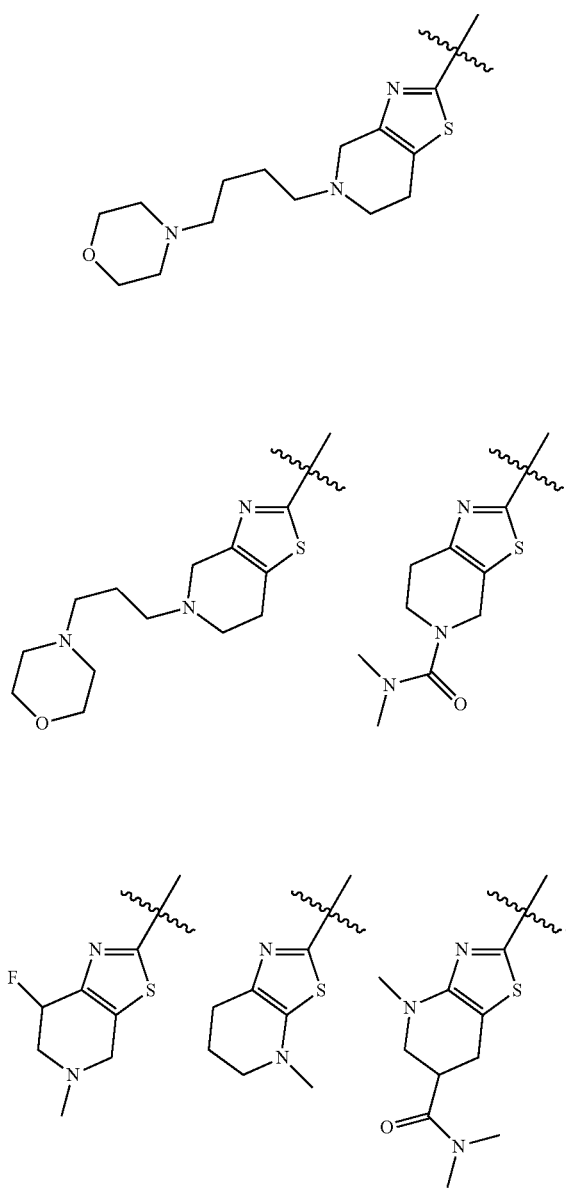
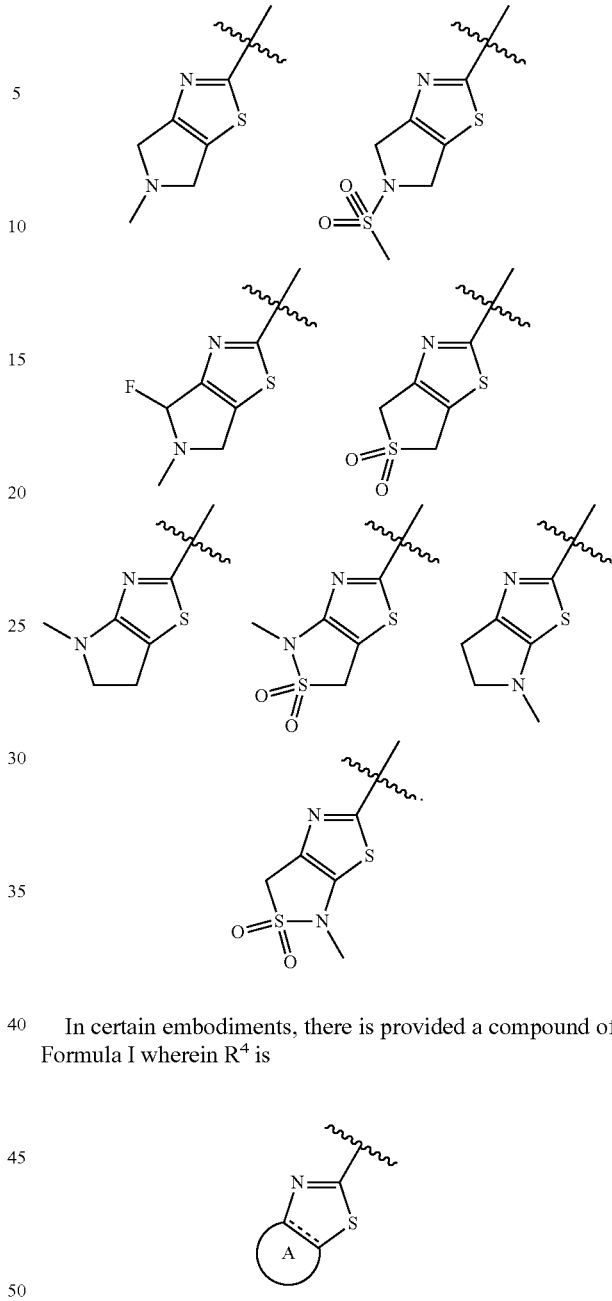

In certain embodiments, there is provided a compound of Formula I wherein R⁴ is

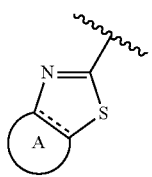

and A is a saturated or partially unsaturated 5 membered heterocyclic ring, wherein said heterocyclic ring is optionally substituted with one or more groups independently selected from halogen, alkyl, SO₂Me, and oxo.

Exemplary embodiments include compounds of Formula I wherein R⁴ is selected from the structures:

In certain embodiments, there is provided a compound of Formula I wherein R⁴ is and A is a benzene ring, wherein the benzene ring is optionally substituted with one or more groups independently selected from halogen, CN, NO₂, C(=O)NR¹⁰R¹¹, NR¹⁰C(=O)NR¹¹R¹², heteroaryl optionally substituted with alkyl, and alkyl optionally substituted with OR¹⁰, NR¹⁰R¹¹ or NR¹⁰C(=O)N(R¹¹)OR¹².

Examples of halogen substituents include F and Cl. Examples of C(=O)NR¹⁰R¹¹ substituents include C(=O)NH₂, C(=O)NHCH₃, and C(=O)N(CH₃)₂. Examples of NR¹⁰C(=O)NR¹¹R¹² substituents include NHC(=O)NH₂, NHC(=O)NHCH₃, and NHC(=O)N(CH₃)₂. Examples of heteroaryl substituents optionally substituted with alkyl include 1,2,4-triazol-1-yl and 3-methyl-1,2,4-triazol-1-yl. Examples of alkyl substituents optionally substituted with OR¹⁰, NR¹⁰R¹¹ or NR¹⁰C(=O)N(R¹¹)OR¹² include CH₂OH, CH₂CH₂OH, CH₂CH₃, CH₂CH₂OCH₃, CH$_2$OCH$_2$CH$_3$, CH$_2$CH$_2$OCH$_2$CH$_3$, CH$_2$NH$_2$, CH$_2$NHCH$_3$, CH$_2$N(CH$_3$)$_2$, CH$_2$CH$_2$NH$_2$, CH$_2$CH$_2$NHCH$_3$, CH$_2$CH$_2$N(CH$_3$), CH$_2$NHC(=O)NHOH, and CH$_2$NHC(=O)NHOCH$_3$.

Exemplary embodiments include compounds of Formula I wherein R$^4$ is selected from the structures:

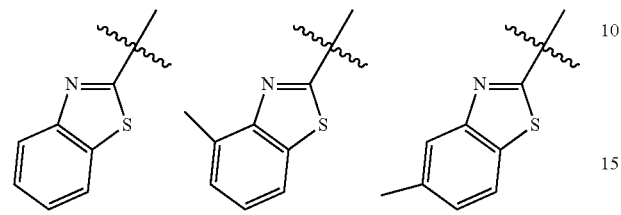

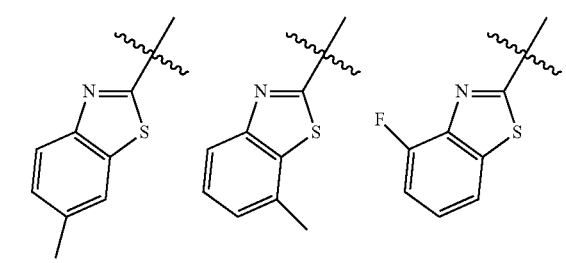

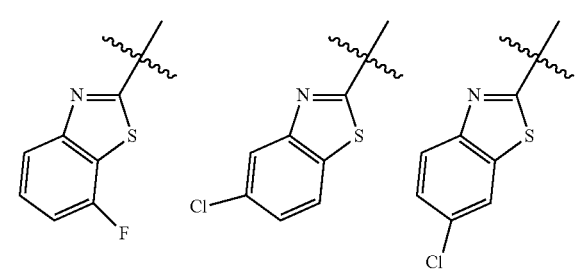

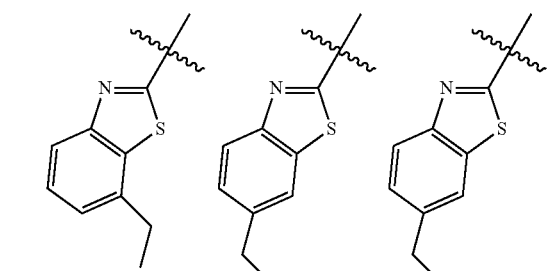

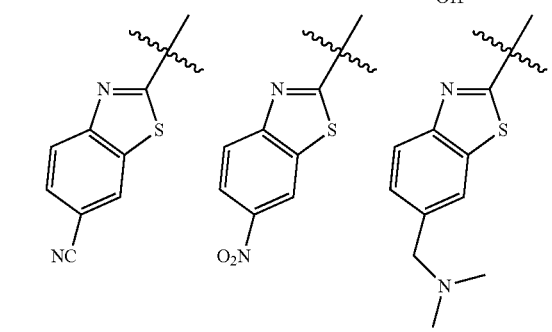

-continued

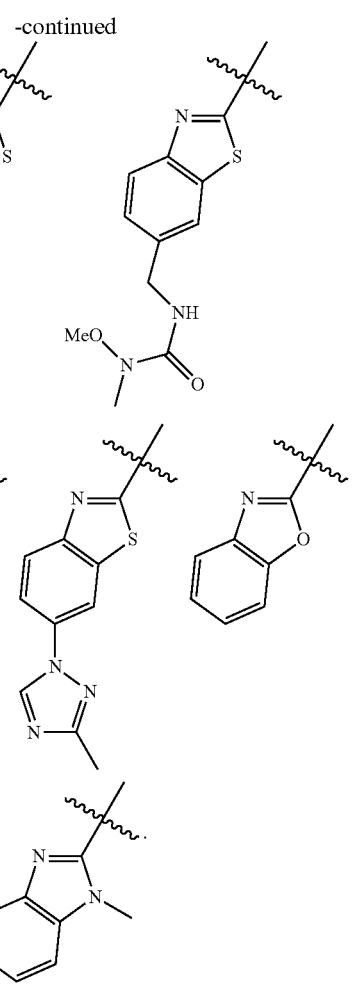

In certain embodiments, there is provided a compound of Formula I wherein R$^4$ is selected from the structures:

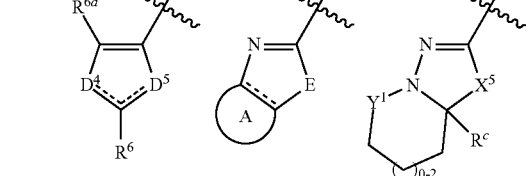

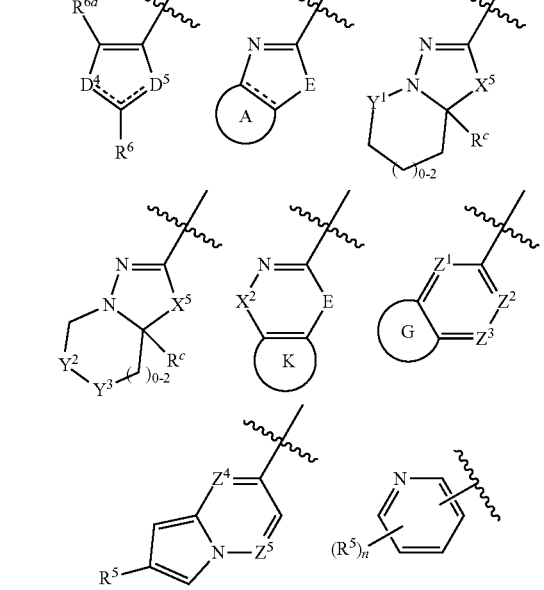

-continued

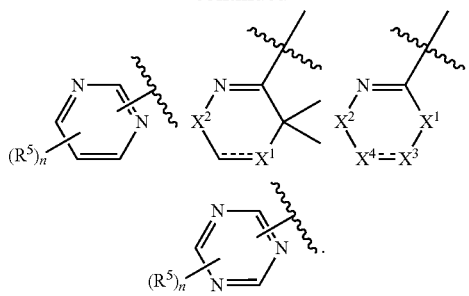

For example, in certain embodiments there is provided a compound of Formula I wherein $R^4$ is

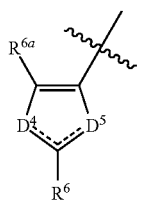

wherein $R^6$ and $R^{6a}$ are independently selected from H and alkyl. In certain embodiments, said alkyl is selected from methyl, ethyl, propyl, isopropyl, butyl, and the like.

Exemplary embodiments include compounds of Formula I wherein $R^4$ is selected from the structures:

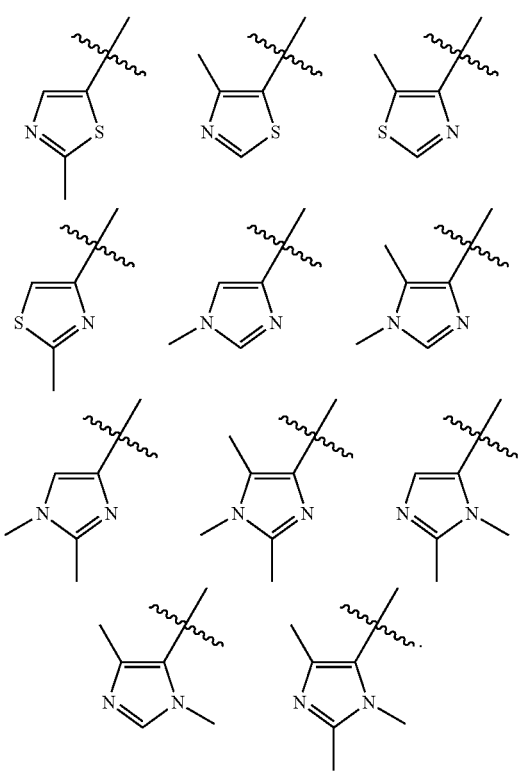

In certain embodiments there is provided a compound of Formula I wherein $R^4$ is

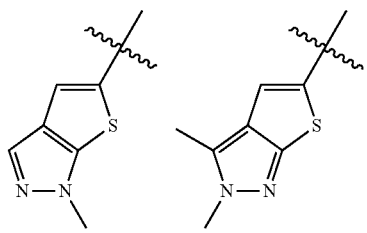

wherein A is a partially unsaturated or fully unsaturated 5-membered heterocyclic ring, wherein said heterocyclic ring is optionally substituted independently with one or more alkyl groups, such as, but not limited to, methyl, ethyl, propyl, isopropyl, butyl, and the like.

Exemplary embodiments include compounds of Formula I wherein $R^4$ is selected from the structures:

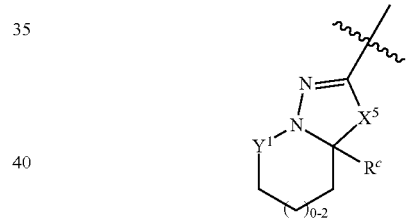

In certain embodiments there is provided a compound of Formula I wherein

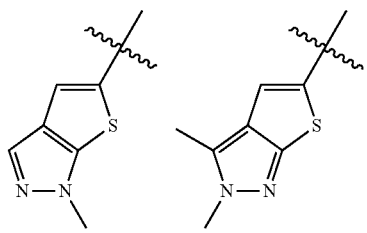

Exemplary embodiments include compounds of Formula I wherein $R^4$ is selected from the structures:

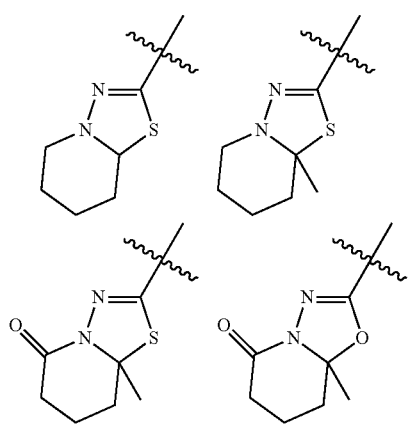

In certain embodiments there is provided a compound of Formula I wherein $R^4$ is

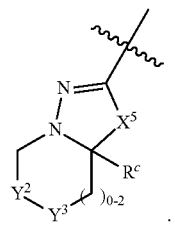

Exemplary embodiments include compounds of Formula I wherein $R^4$ is selected from the structures:

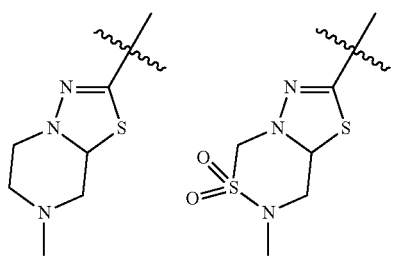

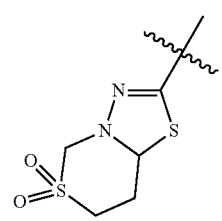

In certain embodiments there is provided a compound of Formula I wherein $R^4$ is

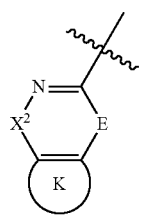

wherein K is optionally substituted independently with one or more alkyl groups, such as, but not limited to, methyl, ethyl, propyl, isopropyl, butyl, and the like.

Exemplary embodiments include compounds of Formula I wherein $R^4$ is selected from the structures:

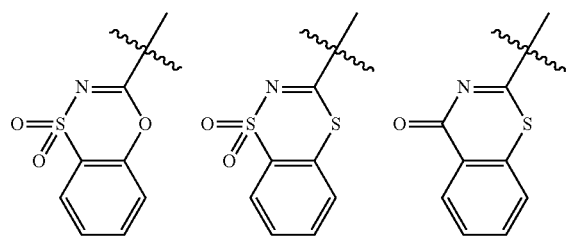

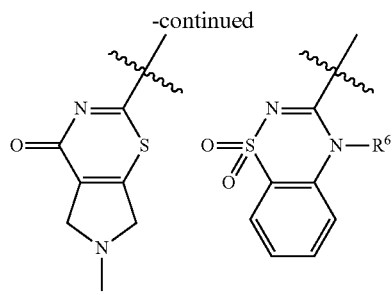

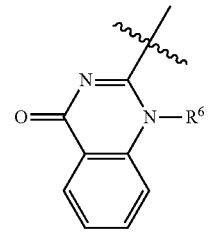

wherein $R^6$ is alkyl. Examples of alkyl groups include, but are not limited to, methyl, ethyl, propyl, isopropyl, butyl, and the like.

In certain embodiments there is provided a compound of Formula I wherein $R^4$ is

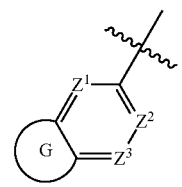

wherein G is optionally substituted independently with one or more alkyl groups, such as, but not limited to, methyl, ethyl, propyl, isopropyl, butyl, and the like.

Exemplary embodiments include compounds of Formula I wherein $R^4$ is selected from the structures:

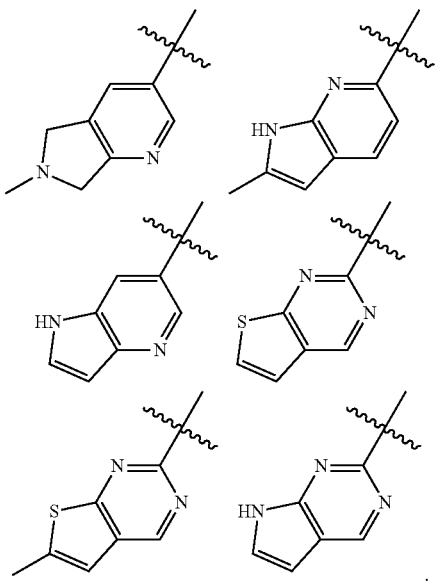

In certain embodiments there is provided a compound of Formula I wherein R⁴ is

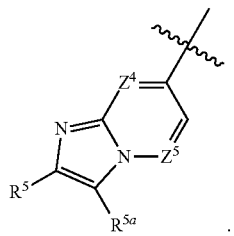

Exemplary embodiments include compounds of Formula I wherein R⁴ is selected from the structures:

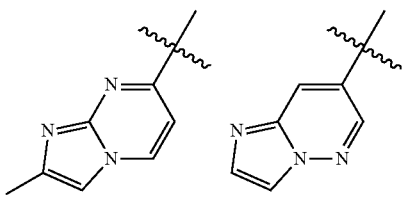

In certain embodiments there is provided a compound of Formula I wherein R⁴ is

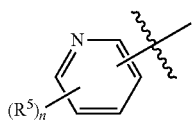

wherein n is 0 or 1, and each $R^5$ is independently $NO_2$, $C(=O)NR^{10}R^{11}$, $NR^{10}C(=O)N(R^{11})OR^{12}$, halogen, CN, or alkyl optionally substituted with one or more groups independently selected from halogen, $OR^{10}$ and $NR^{10}R^{11}$. Examples of $C(=O)NR^{10}R^{11}$ substituents include $C(=O)NH_2$, $C(=O)NHCH_3$, and $C(=O)N(CH_3)_2$. Examples of halogen substituents include F and Cl. Examples of alkyl substituents optionally substituted with halogen, $OR^{10}$, or $NR^{10}R^{11}$ include $CH_2F$, $CHF_2$, $CF_3$, $CH_2CH_2F$, $CH_2CHF_2$, $CH_2CF_3$, $CH_2Cl$, $CH_2Br$, $CH_2OH$, $CH_2CH_2OH$, $CH_2OCH_3$, $CH_2CH_2OCH_3$, $CH_2OCH_2CH_3$, $CH_2CH_2OCH_2CH_3$, $CH_2NH_2$, $CH_2NHCH_3$, $CH_2N(CH_3)_2$, $CH_2CH_2NH_2$, $CH_2CH_2NHCH_3$, and $CH_2CH_2N(CH_3)$ Exemplary embodiments include compounds of Formula I wherein R⁴ is selected from the structures:

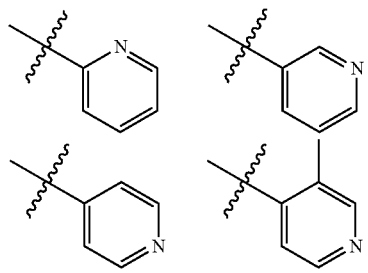

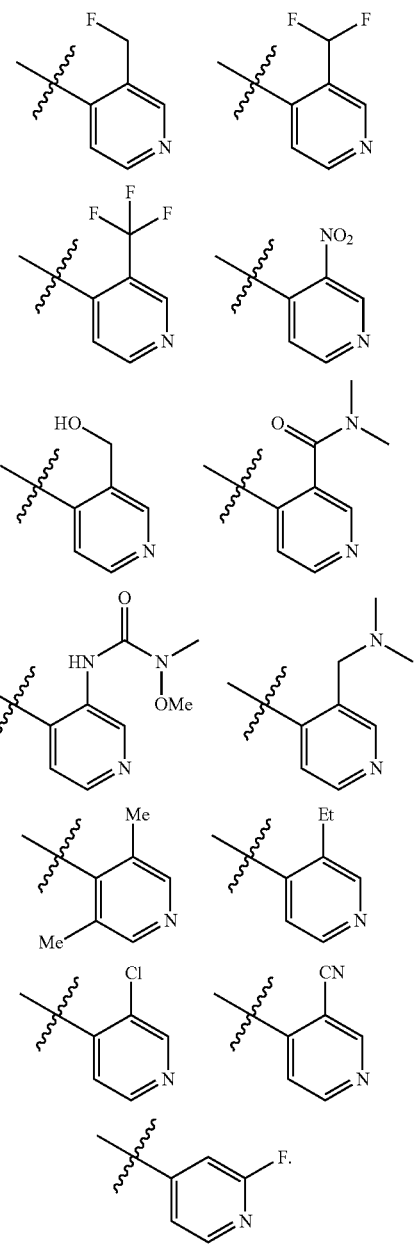

In certain embodiments there is provided a compound of Formula I wherein R⁴ is selected from

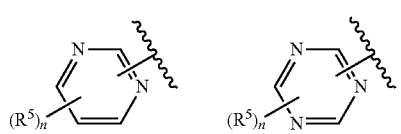

wherein n is 0 or 1, and each $R^5$ is independently $NO_2$, $C(=O)NR^{10}R^{11}$, $NR^{10}C(=O)N(R^{11})OR^{12}$, halogen, CN, or alkyl optionally substituted with one or more groups independently selected from halogen, $OR^{10}$ and $NR^{10}R^{11}$.

Exemplary embodiments include compounds of Formula I wherein R⁴ is selected from the structures:

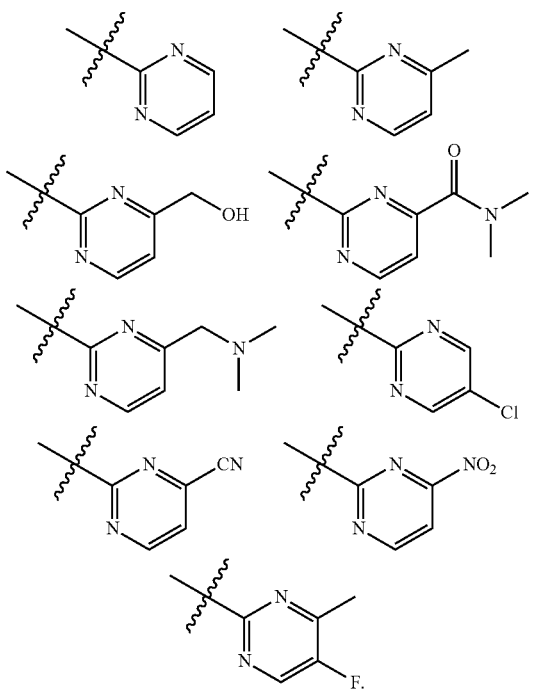

In certain embodiments there is provided a compound of Formula I wherein $R^4$ is

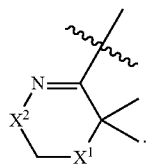

Exemplary embodiments include compounds of Formula I wherein $R^4$ is selected from the structures:

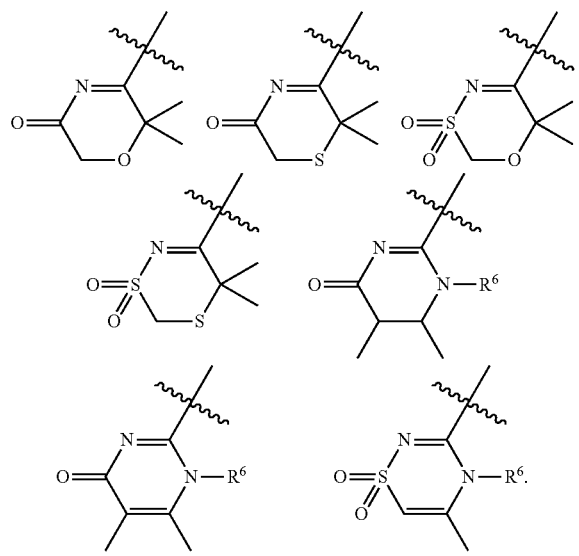

In certain embodiments there is provided a compound of Formula I wherein $R^4$ is

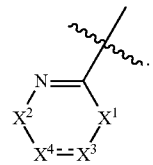

Exemplary embodiments include compounds of Formula I wherein $R^4$ is selected from the structures:

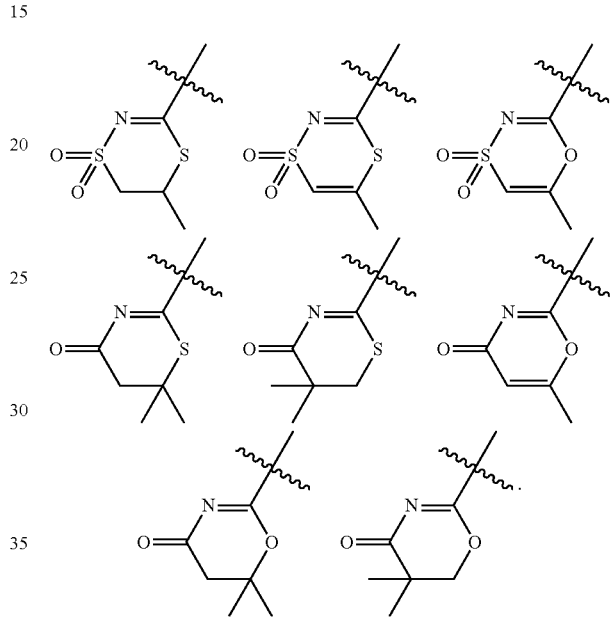

Certain compounds of Formula I can exist as two or more tautomeric forms. A "tautomer" is one of two or more structural isomers that exist in equilibrium and are readily converted from one isomeric form to another, such as structures formed by the movement of a hydrogen from one site to another within the same molecule. Other tautomeric forms of the compounds may interchange, for example, via enolization/de-enolization and the like. Accordingly, the present invention includes the preparation of all tautomeric forms of compounds of Formula I.

The term "alkyl" as used herein refers to a saturated linear or branched-chain monovalent hydrocarbon radical having one to ten carbon atoms, wherein the alkyl radical may be optionally substituted independently with one or more substituents described herein. Examples of alkyl groups include, but are not limited to, methyl, ethyl, n-propyl, isopropyl, butyl, isobutyl, sec-butyl, tert-butyl, pentyl, isopentyl, neopentyl, tert-pentyl, hexyl, 2-hexyl, 3-hexyl, 3-methylpentyl, heptyl, octyl and the like.

Additional examples of alkyl groups include, but are not limited to, 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl(n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 2-methyl-2-pentyl (—C(CH$_3$)$_2$CH$_2$CH$_2$CH$_3$), 3-methyl-2-pentyl (—CH $(CH_3)CH(CH_3)CH_2CH_3)$, 4-methyl-2-pentyl (—CH(CH_3)CH_2CH(CH_3)_2), 3-methyl-3-pentyl (—C(CH_3)(CH_2CH_3)_2), 2-methyl-3-pentyl (—CH(CH_2CH_3)CH(CH_3)_2), 2,3-dimethyl-2-butyl (—C(CH_3)_2CH(CH_3)_2), 3,3-dimethyl-2-butyl (—CH(CH_3)C(CH_3)_3), and the like.

As used herein, an alkyl optionally substituted with one or more halogen groups includes, but is not limited to, $CH_2F$, $CHF_2$, $CF_3$, $CH_2CH_2F$, $CH_2CHF_2$, $CH_2CF_3$, $CH_2CL$, $CH_2Br$, and the like.

As used herein, an alkyl optionally substituted with one or more —C(=O)OR$^{10}$ includes, but is not limited to, $CH_2CO_2CH_3$, $CH_2CO_2CH_2CH_3$, $CH_2CH_2CO_2CH_3$, $CH_2CH_2CO_2CH_2CH_3$, and the like.

As used herein, an alkyl optionally substituted with one or more OR$^{10}$ includes $CH_2OH$, $CH_2CH_2OH$, $CH_2CH_2CH_2OH$, $CH_2CH_2CH(OH)CH_3$, $CH_2C(OH)(CH_3)_2$, $CH_2$—O—$CH_2OMe$, and the like.

As used herein, an alkyl optionally substituted with one or more $OPO_3H_2$ includes $CH_2OPO_3H_2$, $CH_2CH_2OPO_3H_2$, $CH_2CH_2CH_2OPO_3H_2$, and the like.

As used herein, an alkyl optionally substituted with one or more NR$^{10}$R$^{11}$ includes $CH_2NH_2$, $CH_2CH_2NH_2$, $CH_2CH_2CH_2NH_2$, $CH_2NHMe$, $CH_2CH_2NHMe$, $CH_2CH_2CH_2NHMe$, $CH_2NMe_2$, $CH_2CH_2NMe_2$, $CH_2CH_2CH_2NMe_2$, and the like.

As used herein, an alkyl optionally substituted with an amino acid residue includes an alkyl group such as $CH_2$, $CH_2CH_2$, or $CH_2CH_2CH_2$ substituted with any of the natural amino acids, wherein the amino acid is of the D or L configuration. Examples include, but are not limited to, $(CH_2)_3NH(C=O)CH(Me)NH(C=O)CH(Me)NH_2$, $(CH_2)_3NHCH(CH_3)(C=O)NH_2$, and the like.

As used herein, an alkyl optionally substituted with a dipeptide includes $CH_2$-alanine-alanine, $CH_2CH_2$-alanine-alanine, $CH_2CH_2CH_2$-alanine-alanine, and the like, wherein each amino acid residue of the peptide is of the D or L configuration.

As used herein, an alkyl optionally substituted with a tripeptide includes an alkyl such as $CH_2$, $CH_2CH_2$, or $CH_2CH_2CH_2$ substituted with a tripeptide such as, but not limited to, alanine-alanine-alanine, valine-alanine-valine, alanine-valine-valine, and the like, wherein each amino acid residue of the peptide is of the D or L configuration.

As used herein, an alkyl optionally substituted with one or more heterocyclyl includes $(CH_2)_3$-(pyrrolidin-1-yl), $(CH_2)_3$-(piperidin-1-yl), $(CH_2)_3$-(4-methylpiperidin-1-yl), $(CH_2)_3$-(morpholin-4-yl), $(CH_2)_4$-(morpholin-4-yl), $(CH_2)_2$-(pyrrolidin-2-yl), and the like.

As used herein, an alkyl optionally substituted with one or more NR$^{10}$C(=O)N(R$^{11}$)OR$^{12}$ includes $CH_2NHC(=O)N(OMe)Me$ and the like.

As used herein, an alkyl optionally substituted with one or more NR$^{10}$C(=O)(CH_2)$_{0-2}$R$^{11}$ includes $(CH_2)_3NHC(=O)Me$, $(CH_2)_3NHC(=O)CH(CH_3)_2$, $(CH_2)_3NHC(=O)CH_2CH_2NMe_2$ and the like.

As used herein, an alkyl optionally substituted with one or more NR$^{10}$SO$_2$R$^{13}$ includes $(CH_2)_3NHSO_2Me$, $(CH_2)_2NHSO_2Me$ and the like.

The term "alkylene" as used herein refers to a linear or branched saturated divalent hydrocarbon radical of one to twelve carbon atoms, wherein the alkylene radical may be optionally substituted independently with one or more substituents described herein. Examples of alkylene groups include, but are not limited to, methylene, ethylene, propylene, 2-methylpropylene, pentylene and the like.

The term "alkenyl" refers to a linear or branched-chain monovalent hydrocarbon radical having two to ten carbon atoms and at least one double bond, and includes, but is not limited to, ethenyl, propenyl, 1-but-3-enyl, 1-pent-3-enyl, 1-hex-5-enyl and the like, wherein the alkenyl radical may be optionally substituted independently with one or more substituents described herein, and includes radicals having "cis" and "trans" orientations, or alternatively, "E" and "Z" orientations.

The term "alkenylene" refers to a linear or branched divalent hydrocarbon radical of two to twelve carbons containing at least one double bond, wherein the alkenylene radical may be optionally substituted independently with one or more substituents described herein. Examples include, but are not limited to, ethenylene, propenylene and the like.

The term "alkynyl" refers to a linear or branched monovalent hydrocarbon radical of two to twelve carbon atoms containing at least one triple bond. Examples include, but are not limited to, ethynyl, propynyl, butynyl, pentyn-2-yl and the like, wherein the alkynyl radical may be optionally substituted independently with one or more substituents described herein.

The term "alkynylene" refers to a linear or branched divalent hydrocarbon radical of two to twelve carbons containing at least one triple bond, wherein the alkynylene radical may be optionally substituted independently with one or more substituents described herein.

The terms "carbocycle," "carbocyclyl," "cycloalkyl," and "carbocyclic ring" are used interchangeably herein and refer to a saturated or partially unsaturated cyclic monovalent hydrocarbon radical having from three to ten carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl and the like. The cycloalkyl may be optionally substituted independently at one or more substitutable positions with one or more substituents described herein. Such cycloalkyl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl. Bicyclic carbocycles include those having 7 to 12 ring atoms arranged, for example, as a bicyclo[4,5], [5,5], [5,6] or [6,6] system, or as bridged systems such as bicyclo[2.2.1]heptane, bicyclo[2.2.2]octane, and bicyclo[3.2.2]nonane.

The term "heteroalkyl" refers to saturated linear or branched-chain monovalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroalkyl radical may be optionally substituted independently with one or more substituents described herein. The term "heteroalkyl" encompasses alkoxy and heteroalkoxy radicals. For example, heteroalkyls include methoxy ($OCH_3$), ethoxy($OCH_2CH_3$) and the like. Examples further include heteroalkyls substituted with one or more halogen. Examples include, but are not limited to, fluoromethoxy($OCH_2F$), difluoromethoxy($OCHF_2$), trifluoromethoxy($OCF_3$), and the like. Accordingly, a OR$^{10}$ substituent as defined herein can include, but is not limited to, $OCH_3$, $OCH_2CH_3$, $OCH_2F$, ($OCHF_2$), and ($OCF_3$).

The term "heteroalkylene" refers to a linear or branched saturated divalent hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical), such as —(CH$_2$)$_y$O— where y is 1 to 12.

The terms "heterocycloalkyl," "heterocycle," "hetercyclyl" and "heterocyclic ring" are used interchangeably herein and refer to a saturated or partially unsaturated carbocyclic radical of 3 to 8 ring atoms, wherein at least one of the carbon atoms in the ring is substituted with a heteroatom selected from N, O, or S, wherein one or more ring atoms may be optionally substituted independently with one or more substituents described below. The radical may be a carbon radical or heteroatom radical. The terms further include fused ring systems that include a heterocycle fused to a saturated or partially unsaturated cycloalkyl or heterocycloalkyl ring or an aryl or heteroaryl ring. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyclo[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (═O) moieties is 1,1-dioxo-thiomorpholinyl. The heterocycle groups herein are unsubstituted or, as specified, substituted in one or more substitutable positions with one or more substituents described herein. For example, such heterocycle groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$ alkenyl, $C_2$-$C_6$ alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

The term "aryl" refers to a monovalent aromatic carbocyclic radical having a single ring (e.g., phenyl), multiple rings (e.g., biphenyl), or multiple condensed rings in which at least one is aromatic, (e.g., 1,2,3,4-tetrahydronaphthyl, naphthyl, etc.), which are optionally mono-, di-, or trisubstituted independently with substituents such as halogen, lower alkyl, lower alkoxy, trifluoromethyl, aryl, heteroaryl, and hydroxy. The term "aryl" includes bicyclic radicals comprising an aromatic ring fused to a saturated, partially unsaturated ring, or aromatic carbocyclic or heterocyclic ring.

The term "heteroaryl" refers to a monovalent 5-, 6-, or 7-membered monovalent aromatic carbocyclic radical wherein at least one of the carbon atoms in the ring is substituted with a heteroatom selected from N, O, or S, and includes fused ring systems (at least one of which is aromatic) of 5-10 atoms. Examples of heteroaryl groups include, but are not limited to, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups are optionally substituted with one or more substituents described herein.

By way of example and not limitation, carbon bonded heterocycles and heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Further examples of carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles and heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of an isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

The term "halogen" represents fluorine, bromine, chlorine, and iodine.

The term "arylalkyl" means an alkyl moiety (as defined above) substituted with one or more aryl moiety (also as defined above). More preferred arylalkyl radicals are aryl-$C_{1-3}$-alkyls. Examples include, but are not limited to, benzyl, phenylethyl and the like.

The term "heteroarylalkyl" means an alkyl moiety (as defined above) substituted with a heteroaryl moiety (also as defined above). More preferred heteroarylalkyl radicals are 5- or 6-membered heteroaryl-$C_{1-3}$-alkyls. Examples include, but are not limited to, oxazolylmethyl, pyridylethyl and the like.

The term "heterocyclylalkyl" means an alkyl moiety (as defined above) substituted with a heterocyclyl moiety (also defined above). More preferred heterocyclylalkyl radicals are 5- or 6-membered heterocyclyl-$C_{1-3}$-alkyls. An example includes, but is not limited to, tetrahydropyranylmethyl.

The term "cycloalkylalkyl" means an alkyl moiety (as defined above) substituted with a cycloalkyl moiety (also defined above). More preferred cycloalkylalkyl radicals are 5- or 6-membered cycloalkyl-$C_{1-3}$-alkyls. Examples include cyclopropylmethyl.

The term "Me" means methyl, "Et" means ethyl, "Bu" means butyl and "Ac" means acetyl.

In general, the various moieties or functional groups of the compounds of Formula I may be optionally substituted by one or more substituents. Examples of substituents suitable for purposes of this invention include, but are not limited to, oxo, halogen, cyano, nitro, trifluoromethyl, difluoromethoxy, trifluoromethoxy, azido, $OR^{14}$, —$NR^{14}SO_2R^{15}$, —SO$_2$NR$^{14}$R$^{15}$, —C(O)R$^{14}$, —C(O)OR$^{14}$, —OC(O)R$^{14}$, —NR$^{14}$C(O)OR$^{15}$, —NR$^{14}$C(O)R$^{15}$, —C(O)NR$^{14}$R$^{15}$, —NR$^{14}$R$^{15}$, —NR$^{14}$C(O)NR$^{14}$R$^{15}$, —NR$^{14}$C(NCN)NR$^{14}$R$^{15}$, aryl, heteroaryl, arylalkyl, heteroarylalkyl, heterocyclyl, and heterocyclylalkyl, where R$^{14}$ and R$^{15}$ are as defined herein.

It is to be understood that in instances where two or more radicals are used in succession to define a substituent attached to a structure, the first named radical is considered to be terminal and the last named radical is considered to be attached to the structure in question. Thus, for example, an arylalkyl radical is attached to the structure in question by the alkyl group.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes all such isomers, including diastereomeric mixtures and pure enantiomers of the Formula I. Diastereomeric mixtures can be separated into their individual diastereomers on the basis of their physical chemical differences by methods known to those skilled in the art, for example, by chromatography or fractional crystallization. Enantiomers can be separated by converting the enantiomer mixture into a diastereomeric mixture by reaction with an appropriate optically active compound (e.g., alcohol), separating the diastereomers and converting (e.g., hydrolyzing) the individual diastereomers to the corresponding pure enantiomers. The methods for the determination of stereochemistry and the separation of stereoisomers are well known in the art (see discussion in Chapter 4 of "Advanced Organic Chemistry", 4th edition, J. March, John Wiley and Sons, New York, 1992).

In addition to compounds of the Formula I, the invention also includes solvates, pharmaceutically acceptable prodrugs, pharmaceutically active metabolites, solvates, and pharmaceutically acceptable salts of such compounds.

A "pharmaceutically acceptable prodrug" is a compound that may be converted under physiological conditions or by solvolysis to the specified compound or to a pharmaceutically acceptable salt of such compound. Prodrugs include compounds wherein an amino acid residue, or a polypeptide chain of two or more (e.g., two, three or four) amino acid residues (i.e., peptides) is covalently joined through an amide or ester bond to a free amino, hydroxy or carboxylic acid group of compounds of the present invention. Amino acid residues include, but are not limited to, the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. One preferred prodrug of this invention is a compound of Formula I covalently joined to a phosphate residue. Another preferred prodrug of this invention is a compound of Formula I covalently joined to a valine residue or an alanine-alanine dipeptide.

Additional types of prodrugs are also encompassed. For instance, free carboxyl groups can be derivatized as amides or alkyl esters. As another example, compounds of this invention comprising free hydroxy groups may be derivatized as prodrugs by converting the hydroxy group into groups such as, but not limited to, phosphate ester, hemisuccinate, dimethylaminoacetate, or phosphoryloxymethyloxycarbonyl groups, as outlined in *Advanced Drug Delivery Reviews*, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including, but not limited to, ether, amine and carboxylic acid functionalities, or where the acyl group is an amino acid ester as described above, are also encompassed. Prodrugs of this type are described in *J. Med Chem.*, 1996, 39, 10. More specific examples include replacement of the hydrogen atom of the alcohol group with a group such as (C$_1$-C$_6$)alkanoyloxymethyl, 1-((C$_1$-C$_6$)alkanoyloxy)ethyl, 1-methyl-1-((C$_1$-C$_6$)alkanoyloxy)ethyl, (C$_1$-C$_6$) alkoxycarbonyloxymethyl, N—(C$_1$-C$_6$) alkoxycarbonylaminomethyl, succinoyl, (C$_1$-C$_6$)alkanoyl, α-amino(C$_1$-C$_4$)alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O(C$_1$-C$_6$)alkyl)$_2$ or glycosyl (the radical resulting from the removal of a hydroxyl group of the hemiacetal form of a carbohydrate).

Free amines can also be derivatized as amides, sulfonamides or phosphonamides. All of these prodrug moieties may incorporate groups including, but not limited to, ether, amine and carboxylic acid functionalities. For example, a prodrug can be formed by the replacement of a hydrogen atom in the amine group with a group such as R-carbonyl, RO-carbonyl, NRR'-carbonyl where R and R' are each independently (C$_1$-C$_{10}$)alkyl, (C$_3$-C$_7$)cycloalkyl, benzyl, or R-carbonyl is a natural α-aminoacyl or natural α-aminoacyl-natural α-aminoacyl, —C(OH)C(O)OY wherein Y is H, (C$_1$-C$_6$)alkyl or benzyl, —C(OY$_0$)Y$_1$ wherein Y$_0$ is (C$_1$-C$_4$)alkyl and Y$_1$ is (C$_1$-C$_6$)alkyl, carboxy(C$_1$-C$_6$)alkyl, amino(C$_1$-C$_4$)alkyl or mono-N- or di-N,N— (C$_1$-C$_6$)alkylaminoalkyl, —C(Y$_2$)Y$_3$ wherein Y$_2$ is H or methyl and Y$_3$ is mono-N- or di-N,N—(C$_1$-C$_6$)alkylamino, morpholino, piperidin-1-yl or pyrrolidin-1-yl.

Prodrugs of a compound may be identified using routine techniques known in the art. Various forms of prodrugs are known in the art. For examples of such prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 "Design and Application of Prodrugs," by H. Bundgaard p. 113-191 (1991); c) H. Bundgaard, *Advanced Drug Delivery Reviews*, 8, 1-38 (1992); d) H. Bundgaard, et al., *Journal of Pharmaceutical Sciences*, 77:285 (1988); and e) N. Kakeya, et al., *Chem. Pharm. Bull.*, 32: 692 (1984), each of which is specifically incorporated herein by reference.

A "metabolite" is a pharmacologically active product produced through in vivo metabolism of a specified compound or salt or prodrug thereof. Such products may result for example from the oxidation, reduction, hydrolysis, amidation, deamidation, esterification, deesterification, enzymatic cleavage, and the like, of the administered compound. The invention also includes products produced by a process comprising contacting a compound of this invention with a mammal for a period of time sufficient to yield a metabolic product thereof.

Metabolites of a compound may be identified using routine techniques known in the art. For example, metabolite products typically are identified by preparing a radiolabelled (e.g., $^{14}$C or $^3$H) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well-known to those skilled in the art. The metabolite products, so long as they are not otherwise found in vivo, are useful in diagnostic assays for therapeutic dosing of the compounds of the invention.

The term "solvate" refers to an aggregate of a molecule with one or more solvent molecules.

A "pharmaceutically acceptable salt," unless otherwise indicated, includes salts that retain the biological effectiveness of the free acids and bases of the specified compound and that are not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitromenzoates, hydroxybenzoates, methoxybenzoates, phthalates, sulfonates, xylenesulfonates, pheylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates. Since a single compound of the present invention may include more than one acidic or basic moiety, the compounds of the present invention may include mono, di or tri-salts in a single compound.

If the inventive compound is a base, the desired pharmaceutically acceptable salt may be prepared by any suitable method available in the art, for example, treatment of the free base with an acidic compound, particularly an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base. Preferred inorganic salts are those formed with alkali and alkaline earth metals such as lithium, sodium, potassium, barium and calcium. Preferred organic base salts include, for example, ammonium, dibenzylammonium, benzylammonium, 2-hydroxyethylammonium, bis(2-hydroxyethyl)ammonium, phenylethylbenzylamine, dibenzyl-ethylenediamine, and the like salts. Other salts of acidic moieties may include, for example, those salts formed with procaine, quinine and N-methylglusoamine, plus salts formed with basic amino acids such as glycine, ornithine, histidine, phenylglycine, lysine and arginine.

The compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

The inventive compounds may be prepared using the reaction routes and synthetic schemes such as in Schemes I-XIX described below, employing techniques available in the art using starting materials that are readily available or can be synthesized using methods known in the art.

Scheme I

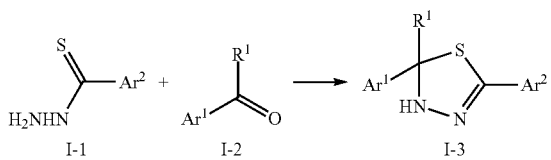

Scheme I illustrates one method of preparing thiadiazoline intermediates of the Formula I-3. Thiocarbazide I-1 (Takasugi, J. J., Buckwalter, B. L., European patent EP 1004241) can be condensed with the desired ketone or aldehyde I-2 in an appropriate organic solvent such as ethanol, methylene chloride, 1,1-diethoxyethane or the like, optionally in the presence of a suitable acid such as acetic acid, at room temperature or elevated temperatures to give a thiadiazoline of Formula I-3. In one embodiment, I-1 is combined with I-2 in ethanol at room temperature to afford thiadiazoline I-3, wherein $R^1$, $Ar^1$ and $Ar^2$ are as defined herein.

Scheme II

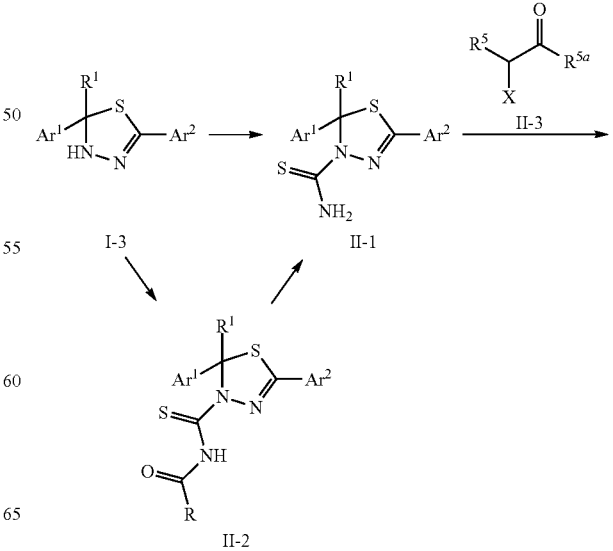

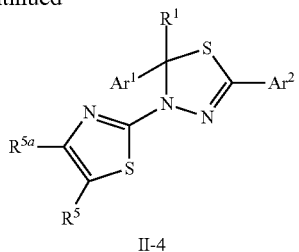

II-4

Thiadiazolylthiadiazolines of the Formula II-4 can be prepared from intermediate I-3 as illustrated in Scheme II. One method for generating thiourea intermediate II-1 comprises reacting intermediate I-3 with an appropriate thiocarbonylating agent such as thiocarbonyldiimidazole or thiocarbonylditriazole in a suitable solvent such as THF, 1,2-dichloroethane, methylene chloride, or acetonitrile at elevated temperatures, followed by treatment with ammonia. In one embodiment, intermediate I-3 is reacted with thiocarbonyldiimidazole in THF at elevated temperatures (e.g., from 60° C. to reflux) and then treated with concentrated aqueous ammonia to afford II-1. Alternatively, II-1 can be synthesized via treatment of I-3 with a suitable acyl isothiocyanate or alkoxycarbonyl isothiocyanate such as benzoyl isothiocyanate, ethoxycarbonyl isothiocyanate, acetyl isothiocyanate or 4-chlorobenzoyl isothiocyanate in an appropriate solvent such as THF, methylene chloride, ethanol, acetone, acetonitrile or DMF at elevated temperatures to form II-2, where R is alkyl, aryl or alkoxy.

Intermediate II-2 can then be converted to II-1 by removal of the acyl or alkoxycarbonyl group with a suitable base such as, but not limited to, $K_2CO_3$, NaOH, NaOMe, ammonia or hydrazine in a suitable solvent such as methanol, ethanol, acetone, THF, or aqueous mixtures of such solvents at elevated temperatures. In one embodiment, I-3 is treated with benzoyl isothiocyanate in THF at reflux to afford II-2, which is then subjected to aqueous $K_2CO_3$ in methanol with heating (70° C.) to generate II-1. Intermediate II-1 can be converted to II-4 by heating with an appropriate α-haloketone or α-haloaldehyde II-3 in a suitable solvent such as ethanol, DMF or acetone at elevated temperatures. Optionally, a base such as diisopropylethylamine or triethylamine can be added to the reaction mixture when either II-1 or II-3 bears acid-sensitive functionality. In one embodiment, intermediate II-1 is heated (60-70° C.) with II-3 and diisopropylethylamine in ethanol to provide compound II-4.

For the purposes of Scheme II, $R^1$, $Ar^1$ and $Ar^2$ are as defined herein, $R^5$ includes, but is not limited to, H, alkyl, cycloalkyl, alkenyl, alkynyl, aryl, heteroaryl, arylalkyl, heteroarylalkyl, heterocyclyl, heterocyclylalkyl, —C(=O)NR$^{10}$R$^{11}$, —C(=O)R$^{10}$, —C(O)OR$^{10}$, and substituted forms thereof, and $R^{5a}$ independently includes, but is not limited to, H, alkyl, cycloalkyl, alkenyl, alkynyl, aryl, heteroaryl, arylalkyl, heteroarylalkyl, heterocyclyl, heterocyclylalkyl, and substituted forms thereof.

Scheme III

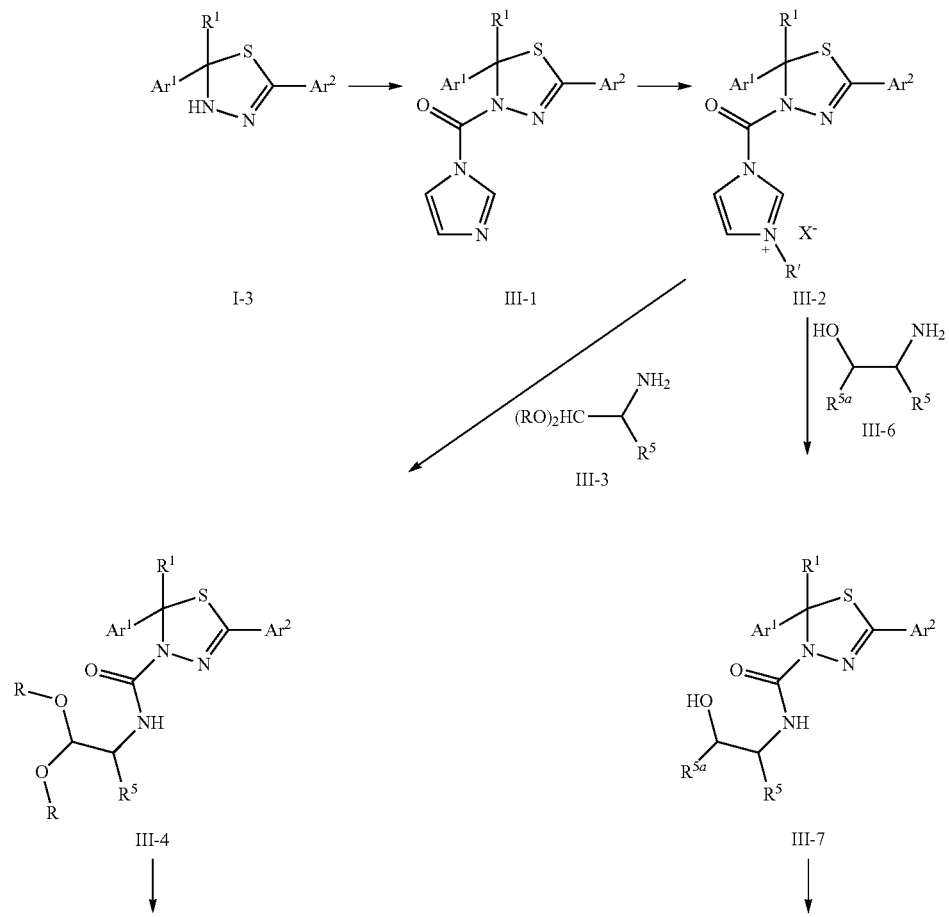

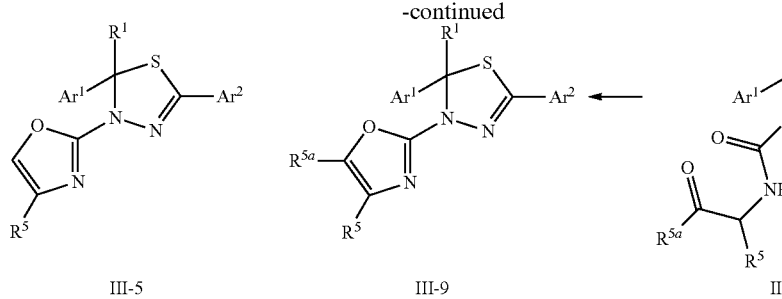

III-5　　　　　　　　III-9　　　　　　　　III-8

Compounds of Formulas III-5 and III-9 can be synthesized as illustrated in Scheme III. To prepare a compound of Formula III-5, intermediate I-3 can be reacted with carbonyldiimidazole in a suitable solvent such as THF or methylene chloride at elevated temperatures to provide III-1. Intermediate III-1 can then be alkylated with a suitable alkylating agent such as, but not limited to, iodomethane, methyl trifluoromethanesulfonate, or benzyl bromide, in an appropriate solvent such as acetonitrile or methylene chloride at room temperature or elevated temperatures to produce imidazolium intermediate III-2, where R' is alkyl or arylmethyl. In one embodiment, III-1 is alkylated using iodomethane in acetonitrile. III-4 can be synthesized by treating III-2 with an appropriate amine of the Formula III-3 in the presence of a base such as triethylamine, diisopropylethylamine or excess III-3 in a suitable solvent such as THF, DMF or methylene chloride. In another embodiment, III-2 is subjected to excess III-3 in methylene chloride to afford urea III-4. Urea III-4 can be converted to 3-oxazolylthiadiazoline III-5 by a procedure that includes hydrolysis of the dialkyl acetal utilizing an appropriate acid such as p-toluenesulfonic acid, TFA or sulfuric acid in a suitable aqueous-organic solvent mixture such as wet acetone, chloroform-water, or wet methanol, followed by isolation of the deprotected intermediate (which can exist as a mixture of aldehyde and hemiacetal species) and subjecting this crude material to conditions for oxazole formation. Oxazole formation can be achieved under a variety of reaction conditions such as, but not limited to: 1) a two-step, one-pot procedure in which the first step comprises treatment with a combination of a phosphine such as triphenylphosphine, a halogenating reagent such as iodine, bromine, hexachloroethane or 1,2-dibromo-1,1,2,2-tetrachloroethane, and a suitable base such as triethylamine, pyridine, collidine, or 2,6-di-tert-butylpyridine in an appropriate solvent such as methylene chloride or acetonitrile, and the second step comprises treatment with a suitable base such as DBU, triethylamine or diisopropylethylamine at room temperature or elevated temperatures; or 2) POCl₃, SOCl₂, Burgess reagent or like reagents in a suitable solvent such as toluene, pyridine, acetonitrile or THF at elevated temperatures. In one embodiment, III-4 is heated at elevated temperature (e.g., 70° C.) with p-toluenesulfonic acid in THF-water solvent. The crude product is then isolated and immediately treated with triphenylphosphine, 1,2-dibromo-1,1,2,2-tetrachloroethane and 2,6-di-tert-butylpyridine in dichloromethane followed by DBU in acetonitrile to afford III-5.

To prepare a compound of Formula III-9, as shown in Scheme III, imidazolium intermediate III-2 can be converted to urea intermediate III-7 by treatment with the appropriate amino alcohol III-6 in the presence of a base such as triethylamine, diisopropylethylamine or excess III-6 in a suitable solvent such as THF or methylene chloride. Oxidation of III-7 to provide ketone III-8 can be achieved by treatment with a suitable oxidizing agent in an appropriate solvent such as methylene chloride or chloroform. Suitable oxidizing agents include, but are not limited to, DMSO/oxalyl chloride/NEt₃ and Dess-Martin periodinane. Intermediate III-8 can be converted to III-9 under suitable reaction conditions such as, but not limited to: 1) a two-step, one-pot procedure in which the first step comprises treatment with a combination of a phosphine such as triphenylphosphine, a halogenating reagent such as iodine, bromine, hexachloroethane or 1,2-dibromo-1,1,2,2-tetrachloroethane, and a suitable base such as triethylamine, pyridine, collidine, or 2,6-di-tert-butylpyridine in an appropriate solvent such as methylene chloride or acetonitrile, and the second step comprises treatment with a suitable base such as DBU, triethylamine or diisopropylethylamine at room temperature or elevated temperatures; or 2) POCl₃, SOCl₂, Burgess reagent or like reagents in a suitable solvent such as toluene, pyridine, acetonitrile or THF at elevated temperatures.

For the purposes of Scheme III, $R^1$, $Ar^1$ and $Ar^2$ are as defined herein, $R^5$ includes, but is not limited to, H, alkyl, cycloalkyl, alkenyl, alkynyl, aryl, heteroaryl, arylalkyl, heteroarylalkyl, heterocyclyl, heterocyclylalkyl, —C(=O)NR$^{10}$R$^{11}$, —C(=O)R$^{10}$, —C(O)OR$^{10}$, and substituted forms thereof, and $R^{5a}$ independently includes, but is not limited to, H, alkyl, cycloalkyl, alkenyl, alkynyl, aryl, heteroaryl, arylalkyl, heteroarylalkyl, heterocyclyl, heterocyclylalkyl, and substituted forms thereof.

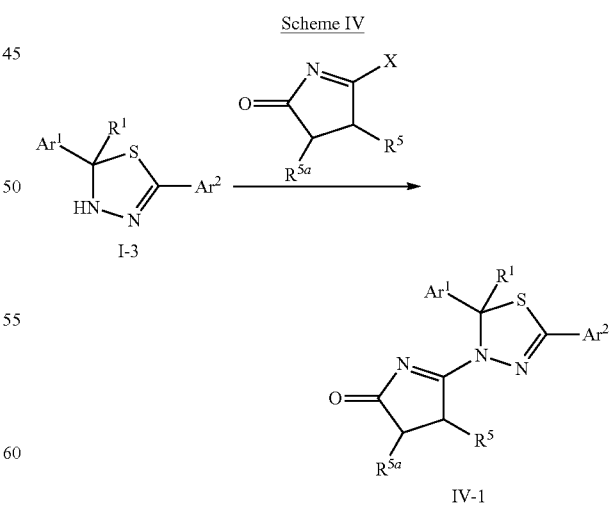

Scheme IV

Scheme IV illustrates a method for preparing 3-dihydropyrrol-one-thiadiazolines. Thiadiazolines of Formula IV-1 can be prepared by reacting intermediate I-3 with 3,4-dihydropyrrol-2-one (where X is a leaving group) in a suitable organic solvent such as THF, ethanol, methylene chloride, 1,1-diethoxyethane, isopropanol or the like at elevated temperatures (e.g., 60-80° C.). In one embodiment, I-3 is reacted with 5-ethoxy-3,4-dihydropyrrol-2-one (*Chem. Pharm. Bull.*, 22(12), 2999 (1974)) in THF and isopropanol at 80° C. to afford a thiadiazoline of Formula IV-1.

For the purposes of Scheme IV, $R^1$, $Ar^1$ and $Ar^2$ are as defined herein, and $R^5$ and $R^{5a}$ independently include, but are not limited to, H, halogen, cyano, nitro, azido, —$NR^{10}R^{11}$, —$NR^{10}SO_2R^{13}$, —$SO_2NR^{10}R^{11}$, —$C(=O)R^{10}$, —$C(O)OR^{10}$, —$OC(=O)R^{10}$, —$NR^{10}C(=O)OR^{13}$, —$NR^{10}C(=O)R^{11}$, —$C(=O)NR^{10}R^{11}$, —$SR^{10}$, —$S(O)R^{13}$, —$SO_2R^{13}$, $SO_2NHC(=O)R^{10}$, —$NR^{10}C(=O)NR^{11}R^{12}$, —$NR^{10}C(NCN)NR^{11}R^{12}$, —$OR^{10}$, alkyl, cycloalkyl, alkenyl, alkynyl, aryl, heteroaryl, arylalkyl, heteroarylalkyl, heterocyclyl, heterocyclylalkyl, and substituted forms thereof.

Scheme V

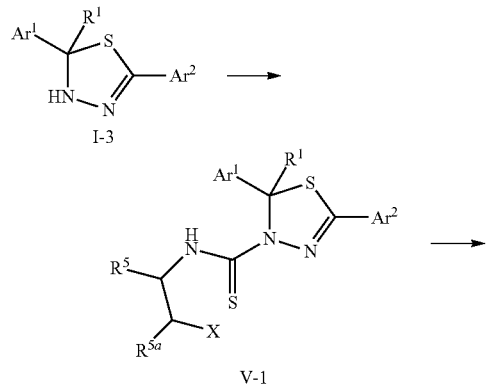

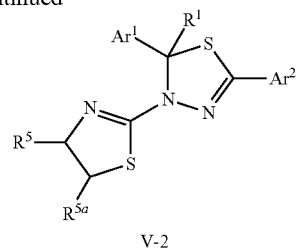

V-2

Scheme V illustrates a method of preparing 3-(4,5-dihydrothiazol-2-yl)-thiadiazolines of Formula V-2. Intermediate V-1 can be prepared from I-3 in a manner similar to the preparation of II-1 in Scheme II. In one embodiment, I-3 is reacted with thiocarbonyldiimidazole in THF at reflux and then treated with 2-bromoethylamine at reflux to afford V-1 where X is bromine. Optionally, a base such as diisopropylethylamine or triethylamine can be added in the presence of acid-sensitive functionality. Intermediate V-1, where X is a leaving group, can be converted to a thiadiazoline V-2 with a suitable base such as, but not limited to, a tertiary amine, $K_2CO_3$, NaOMe, or NaOH, or by heating intermediate V-1 at elevated temperatures in a suitable organic solvent such as THF, ethanol, methylene chloride, 1,1-diethoxyethane, isopropanol or the like. In one embodiment, V-1 is heated at elevated temperatures (e.g., 70-90° C.) in THF to afford a thiadiazoline of Formula V-2.

For the purposes of Scheme V, $R^1$, $Ar^1$ and $Ar^2$ are as defined herein $R^5$ and $R^{5a}$ independently include, but are not limited to, H, alkyl, cycloalkyl, alkenyl, alkynyl, aryl, heteroaryl, arylalkyl, heteroarylalkyl, heterocyclyl, heterocyclylalkyl, —$C(=O)NR^{10}R^{11}$, —$C(=O)R^{10}$, —$C(O)OR^{10}$, and substituted forms thereof.

Scheme VI

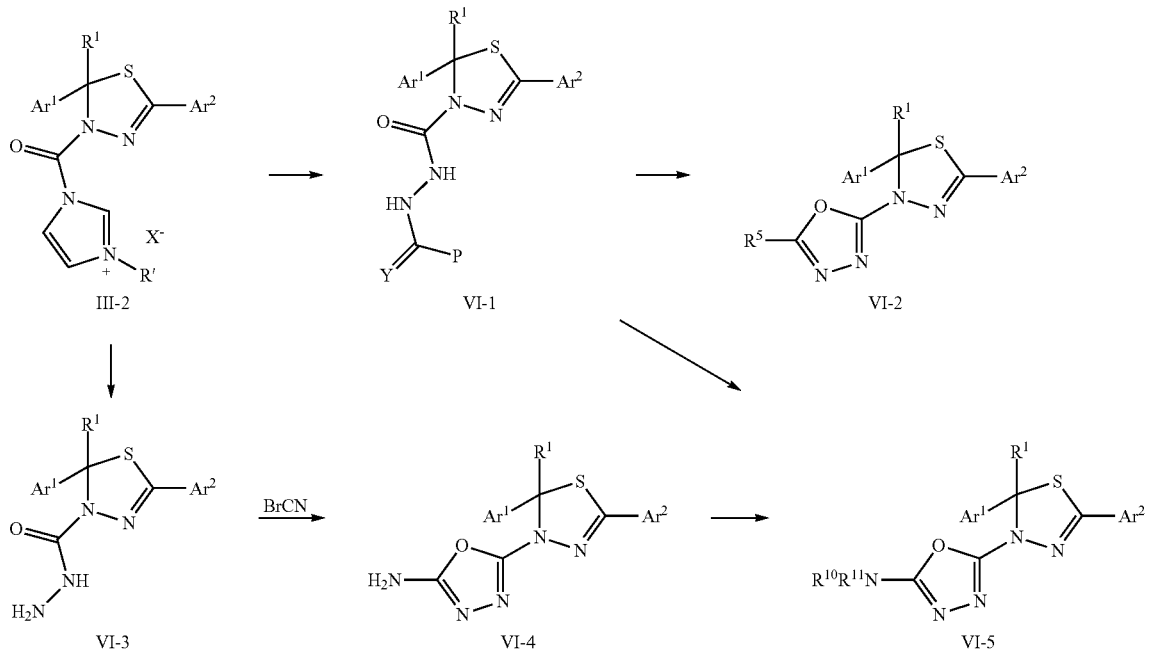

Y = O or S
P = $R^5$ or $NR^{10}R^{11}$

Scheme VI illustrates methods for preparing 5-(1,3,4-thiadiazol-3(2H)-yl)-1,3,4-oxadiazoles. According to one method, intermediate III-2 is reacted with the appropriate hydrazide, thiohydrazide, semicarbazide or thiosemicarbazide and a suitable base such as triethylamine or diisopropylethylamine in an organic solvent such as DCM, THF, DCE, acetone, DMF or acetonitrile to give thiadiazoline VI-1 where Y is O or S and P is $R^5$ or $NR^{10}R^{11}$, where $R^{10}$ and $R^{11}$ are as defined herein. For the purposes of Scheme VI, $R^5$ includes, but is not limited to, H, alkyl, cycloalkyl, alkenyl, alkynyl, aryl, heteroaryl, arylalkyl, heteroarylalkyl, heterocyclyl, heterocyclylalkyl, and substituted forms thereof. Thiadiazoline VI-2 can then be prepared by reacting intermediate VI-1 with $POCl_3$, EDCI, MeI or other activating agent with the optional addition of a suitable base such as triethylamine or diisopropylethylamine in a suitable organic solvent such as DCE, DCM, DMF, THF or acetonitrile. In one embodiment, intermediate III-2 is reacted with acetohydrazide and triethylamine in DCM to give intermediate VI-1, where P is methyl and Y is oxygen. Intermediate VI-1 is then reacted with $POCl_3$ and diisopropylethylamine in DCE at room temperature to give oxadiazole VI-2.

In another embodiment as shown in Scheme VI, intermediate III-2 can be reacted with a thiosemicarbazide in a suitable organic solvent such as THF, MeCN, DCM or DCE at room temperature to give intermediate VI-1 where Y is sulfur and P is $NR^{10}R^{11}$. Intermediate VI-1 is then treated with EDCI or other suitable activating agent to give amino oxadiazole VI-5, wherein $R^1$, $Ar^1$, $Ar^2$, $R^{10}$ and $R^{11}$ are as defined herein.

Alternatively, as also shown in Scheme VI, intermediate III-2 can be treated with hydrazine and an appropriate base such as triethylamine, diisopropylethylamine or excess hydrazine in a suitable organic solvent such as DCM, THF, DCE, acetone, DMF or acetonitrile to give intermediate VI-3. Intermediate VI-3 can then be treated with BrCN in the presence of a suitable base such as triethylamine, diisopropylethylamine, $K_2CO_3$, $NaHCO_3$, or NaOAc in an appropriate organic solvent such as DCE, DCM, THF, ether, or acetonitrile at room temperature or elevated temperatures to give oxadiazole VI-4. Functionalization of the amino group affords oxadiazoles VI-5 (*Arzneimittel-Forschung* (2003), 53(5), 301-306; *Heterocyclic Communications* (2003), 9(2), 199-202; *Arzneimittel-Forschung* (2003), 53(1), 44-52).

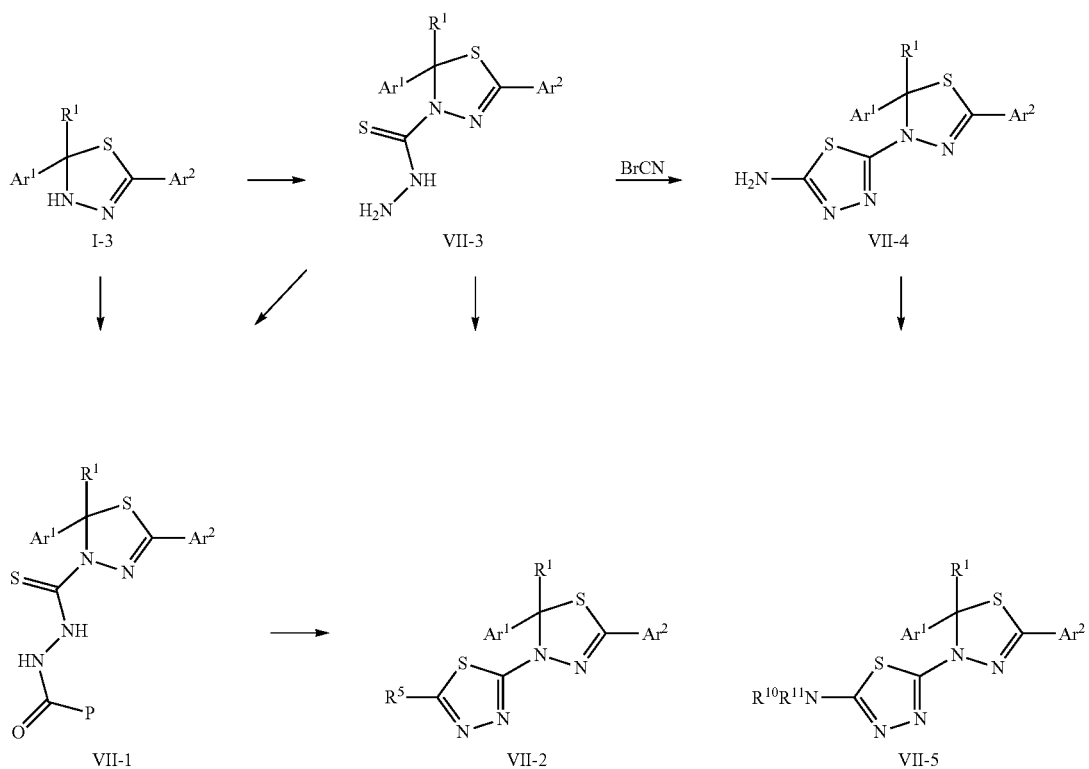

Scheme VII 5-(1,3,4-thiadiazol-3(2H)-yl)-1,3,4-thiadiazoles of Formula VII-2 can be prepared from intermediate I-3 as illustrated in Scheme VII. One method includes preparing intermediate VII-1 by reacting I-3 with an appropriate thiocarbonylating agent such as thiocarbonyldiimidazole or thiocarbonylditriazole in a suitable solvent such as THF, 1,2-dichloroethane, methylene chloride, or acetonitrile at elevated temperatures followed by treatment with the appropriate hydrazide or semicarbazide to provide intermediate VII-1. Thiadiazoline VII-2 can be prepared by reacting intermediate VII-1 with $POCl_3$, EDCI, MeI or other activating agent, optionally in the presence of a suitable base such as triethylamine or diisopropylethylamine, in a suitable organic solvent such as DCE, DCM, DMF, THF or acetonitrile. Alternatively, VII-1 can be synthesized via VII-3, which can be prepared by reacting I-3 with an appropriate thiocarbonylating agent such as thiocarbonyldiimidazole or thiocarbonylditriazole in a suitable solvent such as THF, 1,2-dichloroethane, methylene chloride, or acetonitrile at elevated temperatures followed by addition of hydrazine. Treatment of VII-3 with a suitable isocyanate, anhydride or acyl chloride in an appropriate solvent such as THF, methylene chloride, ethanol, acetone, acetonitrile or DMF provides intermediate VII-1. In one embodiment, intermediate I-3 is reacted with thiocarbonyldiimidazole in THF at elevated temperatures (e.g., from 60° C. to reflux) and then treated with hydrazine to afford intermediate VII-3. Intermediate VII-3 is then reacted with an acid anhydride in dichloromethane to give VII-1, which is treated with $POCl_3$ and diisopropylethylamine in DCE at room temperature to give thiadiazole VII-2.

Alternatively, as shown in Scheme VII, 5-(1,3,4-thiadiazol-3(2H)-yl)-1,3,4-thiadiazole VII-2 can be prepared through thiadiazoline VII-3 upon treatment with 1,1,1-trialkoxyalkanes and a suitable acid such as p-toluenesulfonic acid, camphorsulfonic acid or TFA in neat 1,1,1-trialkoxyalkane or in a suitable solvent such as DMF, DCM, or alcoholic solvent at elevated temperatures. In another embodiment, VII-3 is reacted with trimethyl orthoformate and catalytic amount of p-toluenesulfonic acid at 60° C. to afford VII-2 where $R^5$ is hydrogen.

Intermediate VII-3 can also be treated with BrCN in the presence of a suitable base such as triethylamine, diisopropylethylamine, $K_2CO_3$, $NaHCO_3$ or NaOAc in an appropriate organic solvent such as DCE, DCM, THF, ether, or acetonitrile at room temperature or elevated temperatures to give thiadiazole VII-4. Functionalization of the amino group affords thiadiazoles VII-5 (*Arzneimittel-Forschung* (2003), 53(5), 301-306; *Heterocyclic Communications* (2003), 9(2), 199-202; *Arzneimittel-Forschung* (2003), 53(1), 44-52).

For the purposes of Scheme VII, $R^1$, $Ar^1$, $Ar^2$, $R^{10}$ and $R^{11}$ are as defined herein, and $R^5$ includes, but is not limited to, H, $-NR^{10}R^{11}$, alkyl, cycloalkyl, alkenyl, alkynyl, aryl, heteroaryl, arylalkyl, heteroarylalkyl, heterocyclyl, heterocyclylalkyl, and substituted forms thereof.

Scheme VIII illustrates methods for preparing 5-(1,3,4-thiadiazol-3(2H)-yl)-1,2,4-oxadiazoles of Formula VIII-3. Thiadiazoline VIII-1 can be prepared by reacting intermediate III-2 with N-hydroxyamidine or N'-hydroxyguanidine in a suitable organic solvent such as DCM, THF, DCE, acetone, DMF or acetonitrile. Intermediate VIII-1 can be converted to thiadiazoline VIII-3 by treatment with a dehydrating agent or by heating. Alternatively, VIII-1 can be transformed to VIII-2, wherein OR' is a leaving group, by treatment with acetic anhydride, acetyl chloride, methanesulfonyl chloride, p-toluenesulfonyl chloride or like reagents. Intermediate VIII-2 can be cyclized to thiadiazoline VIII-3 by treatment with a dehydrating agent or by heating. In one embodiment, intermediate III-2 is reacted with N-hydroxyacetamidine in DCM to give intermediate VIII-1 wherein $R^5$ is methyl. Intermediate VIII-1 is treated with acetic anhydride in DCM to afford VIII-2, where R' is C(O)Me and $R^5$ is methyl. Intermediate VIII-2 is then heated in pyridine at 80° C. to give thiadiazoline VIII-3.

For the purposes of Scheme VIII, $R^1$, $Ar^1$, and $Ar^2$ are as defined herein, and $R^5$ includes, but is not limited to, H, $-NR^{10}R^{11}$, alkyl, cycloalkyl, alkenyl, alkynyl, aryl, heteroaryl, arylalkyl, heteroarylalkyl, heterocyclyl, heterocyclylalkyl, and substituted forms thereof.

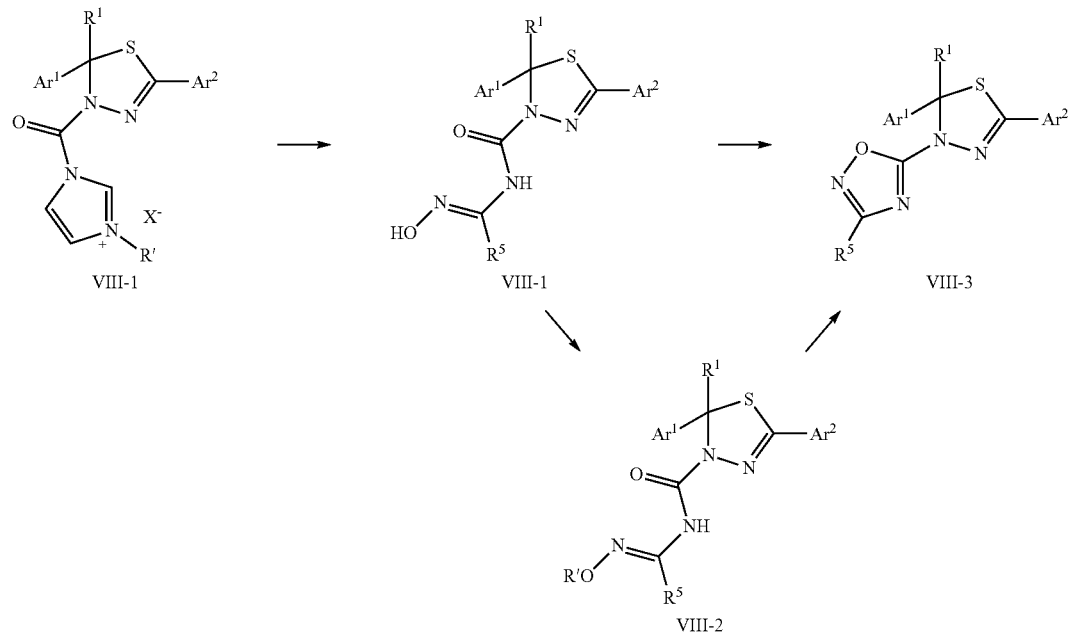

Scheme VIII

Scheme IX

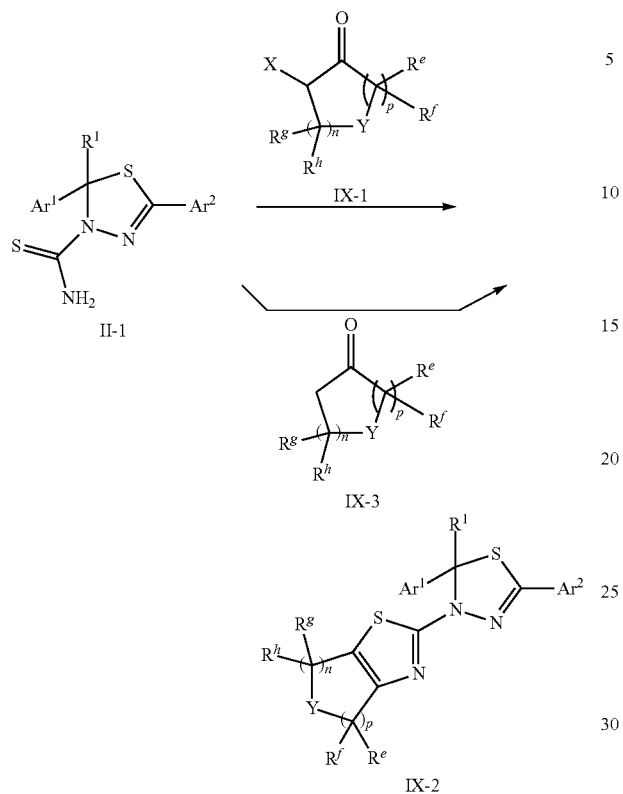

Scheme X

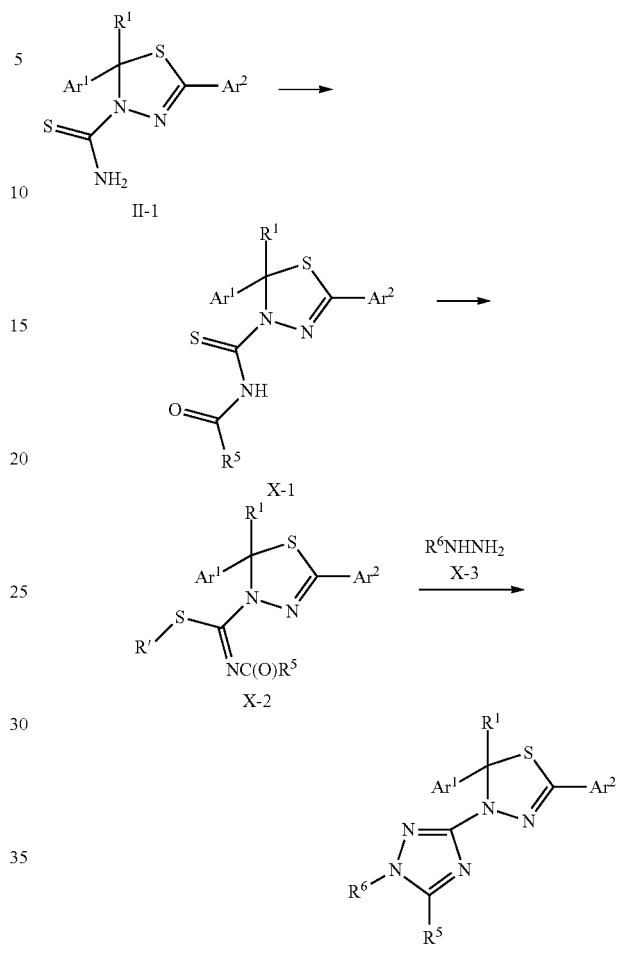

Thiadiazolylthiadiazolines of the Formula IX-2 can be prepared from intermediate II-1 as illustrated in Scheme IX. Intermediate II-1 can be converted to IX-2 by heating with an appropriate cyclic ketone X-1, wherein X is halogen or other suitable leaving group, Y is oxygen, sulfur, —S(O)—, —S(O)$_2$—, a substituted nitrogen group or an optionally substituted carbon group, n is an integer from 1 to 4 and p is an integer from 1 to 4, in an appropriate solvent such as ethanol, DMF or acetone at elevated temperatures to provide IX-2. Appropriate cyclic ketones IX-1 include, but are not limited to, 2-chlorocyclohexanone, 2-chlorocyclopentanone and tert-butyl 3-bromo-4-oxopiperidine-1-carboxylate. Optionally, a base such as diisopropylethylamine or triethylamine can be added to the reaction mixture when II-1 bears acid-sensitive functionality. Alternatively, compounds of the Formula IX-2 may be synthesized by a two-step, one-pot procedure in which an appropriate cyclic ketone of the Formula IX-3 is first halogenated by treatment with iodine, bromine or other suitable halogenating agent in a suitable solvent such as ethanol, acetic acid or carbon tetrachloride at elevated temperatures and then subjected to II-1 at elevated temperatures.

For the purposes of Scheme IX, $R^1$, $Ar^1$ and $Ar^2$ are as defined herein, and $R^e$, $R^f$, $R^g$, and $R^h$ include, but are not limited to, Cl, F, cyano, nitro, azido, —OR$^{10}$, —NR$^{10}$R$^{11}$, —NR$^{10}$SO$_2$R$^{13}$, SO$_2$NR$^{10}$R$^{11}$, —C(=O)R$^{10}$, —C(O)OR$^{10}$, —OC(=O)R$^{10}$, —NR$^{10}$C(=O)OR$^{13}$, —NR$^{10}$C(=O)R$^{11}$, —C(=O)NR$^{10}$R$^{11}$, —SR$^{10}$, —S(O)R$^{13}$, SO$_2$R$^{13}$, —SO$_2$NHC(=O)R$^{10}$—NR$^{10}$C(=O)NR$^{11}$R$^{12}$, —NR$^{10}$C(NCN)NR$^{11}$R$^{12}$, alkyl, cycloalkyl, alkenyl, alkynyl, aryl, heteroaryl, arylalkyl, heteroarylalkyl, heterocyclyl, heterocyclylalkyl, and substituted forms thereof.

Triazolylthiadiazolines of the Formula X-4 can be prepared from intermediate II-1 as illustrated in Scheme X. Intermediate II-1 may be acylated with the appropriate acyl halide or acid anhydride in a suitable solvent such as THF, methylene chloride, acetone, acetonitrile or DMF to form X-1. Alternatively, X-1 may be synthesized in a manner similar to that of intermediate II-2 as shown in Scheme II. Intermediate X-1 can then be alkylated to form X-2, where R' is an alkyl group, by treatment with methyl iodide, methyl trifluoromethanesulfonate or other suitable alkylating agent in the presence of a suitable base such as sodium carbonate, potassium carbonate, NaOH, or Ag$_2$O, in an appropriate solvent such as acetone, acetonitrile, THF, DMF or methanol. X-2 can then be treated with a hydrazine of formula X-3 in a suitable solvent such as ethanol, DMF, THF or acetonitrile at room temperature or at elevated temperatures to afford triazole X-4 as the predominant product. When $R^6$ is hydrogen, X-4 or a tautomer of X-4 is obtained. In one embodiment, I-3 is treated with benzoyl isothiocyanate in THF at reflux as shown in Scheme II to give X-1 wherein $R^5$ is phenyl. Alkylation of X-1 with methyl iodide and sodium carbonate in THF affords X-2 wherein R' is methyl. Treatment of X-2 with hydrazine in ethanol provides X-4 wherein $R^6$ is hydrogen.

For the purposes of Scheme X, $R^1$, $Ar^1$ and $Ar^2$ are as defined herein, $R^5$ includes, but is not limited to, H, alkyl, cycloalkyl, alkenyl, alkynyl, aryl, heteroaryl, arylalkyl, heteroarylalkyl, heterocyclyl, heterocyclylalkyl, and substituted forms thereof; and $R^6$ may include, but is not limited to, H, alkyl, cycloalkyl, alkenyl, alkynyl, aryl, heteroaryl, heterocyclyl, and substituted forms thereof.

$NR^{11}R^{12}$, $-NR^{10}C(NCN)NR^{11}R^{12}$, $-OR^{10}$, alkyl, cycloalkyl, alkenyl, alkynyl, aryl, heteroaryl, arylalkyl, heteroarylalkyl, heterocyclyl, heterocyclylalkyl, and substituted forms thereof.

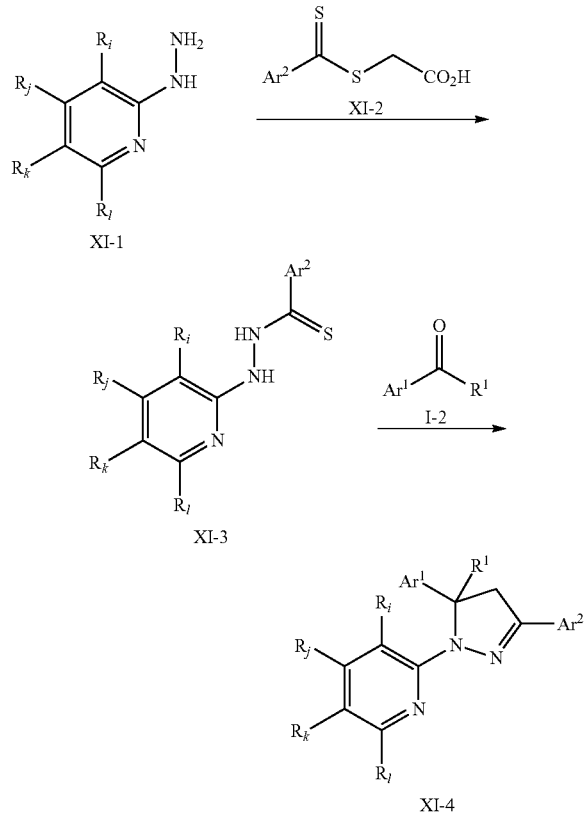

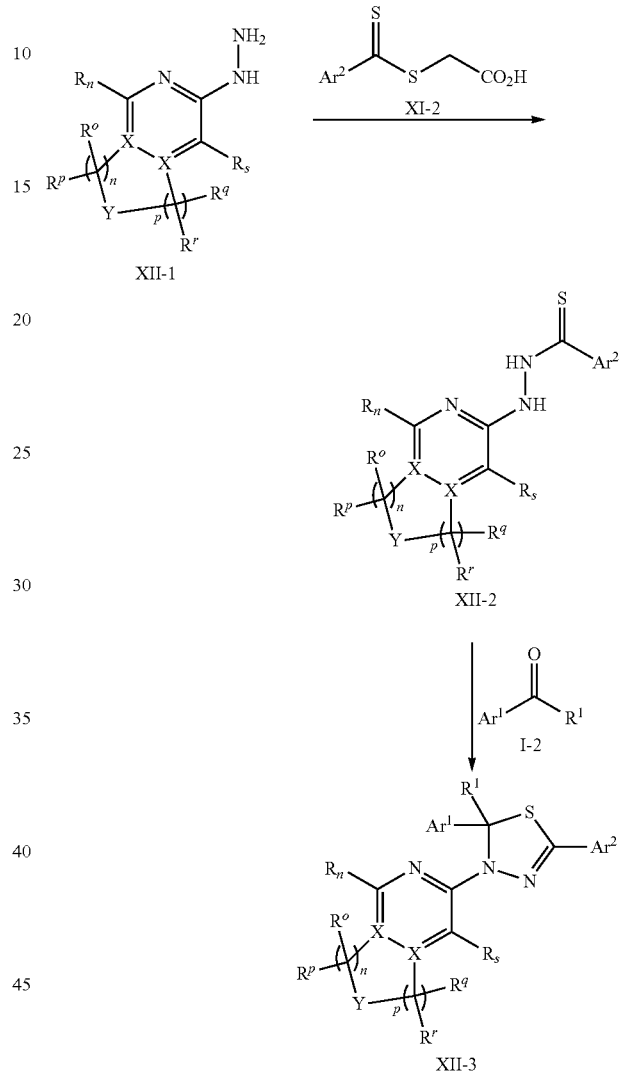

Scheme XI illustrates a method for preparing pyridinyl-thiadiazolines and pyrimidyl-thiadiazolines, using pyridine based analog XI-1 as shown, or an appropriately substituted pyrimidine. Substituted thiohydrazides of formula XI-3, can be readily formed by reaction of XI-1 with an appropriate conjugate thioester XI-2, in an appropriate solvent such as ethanol, DMF, THF, water or mixtures at room or below (for example, at a temperature ranging from −10° C. to 30° C.) under basic conditions such as, potassium carbonate, sodium carbonate, sodium bicarbonate, triethyl amine and similar entities. Thiadiazolines of Formula XI-4 can be prepared by reacting intermediate XI-3 with an appropriately substituted aldehyde or ketone I-2 in a suitable organic solvent such as THF, ethanol, methylene chloride, 1,1-diethoxyethane, isopropanol or the like, at a temperature ranging from, for example, 23-80° C. In one embodiment, XI-3 is reacted with benzaldehyde (Acta Chem. Scand. (14), 789, (1960); J. Chem. Soc. Perkin Trans I (2), 360 (1981)) in ethanol, with catalytic hydrochloric acid, at a temperature of, for example, 23° C., to afford a thiadiazoline of Formula XI-4.

For the purposes of Scheme XI, $R^1$, $Ar^1$ and $Ar^2$ are as defined herein, $R_i$, $R_j$, $R_k$, and $R_l$ independently include, but are not limited to, H, halogen, cyano, nitro, azido, $-NR^{10}R^{11}$, $-NR^{10}SO_2R^{13}$, $-SO_2NR^{10}R^{11}$, $-C(=O)R^{10}$, $-C(O)OR^{10}$, $-OC(=O)R^{10}$, $-NR^{10}C(=O)OR^{13}$, $-NR^{10}C(=O)R^{11}$, $-C(=O)NR^{10}R^{11}$, $-SR^{10}$, $-S(O)R^{13}$, $-SO_2R^{13}$, $-SO_2NHC(=O)R^{10}$, $-NR^{10}C(=O)$ Scheme XII illustrates a method for preparing bicyclic pyridinyl-thiadiazolines and bicyclic pyrimidinyl-thiadiazolines, using appropriately substituted pyridinyl hydrazines XII-1 as depicted or similarly substituted pyrimidinyl hydrazines. Intermediate XII-1 can be converted to XII-2 wherein Y is oxygen, sulfur, $-S(O)-$, $-S(O)_2-$, a substituted nitrogen group or an optionally substituted carbon group, n is an integer from 1 to 4 and p is an integer from 1 to 4; X is nitrogen or an optionally substituted carbon group, by reaction with an appropriate thioester XI-2, in an appropriate solvent such as ethanol, DMF, THF, water or mixtures at or below room temperature (for example between −10° C. to 30° C.) utilizing bases such as, potassium carbonate, sodium carbonate, sodium bicarbonate, triethylamine and similar entities. Thiadiazolines of Formula XII-3 can be prepared by reacting intermediate XII-2 with an appropriately substituted aldehyde or ketone I-2 in a suitable organic solvent such as THF, ethanol, methylene chloride, 1,1-diethoxyethane, isopropanol or the like at a temperature ranging, for example, from 23-80° C. as described in Scheme XI, and exemplified in (*Arkiv Kemi*. (9), 255, (1956); *Acta Chem. Scand*. (14), 789, (1960); *J. Chem. Soc. Perkin Trans I* (2), 360 (1981).

For the purposes of Scheme XII, $R^1$, $Ar^1$ and $Ar^2$ are as defined herein, $R_n$, $R_o$, $R_p$, $R_q$, $R_r$, and $R_s$ independently include, but are not limited to, H, halogen, cyano, nitro, azido, $—NR^{10}R^{11}$, $—NR^{10}SO_2R^{13}$, $—SO_2NR^{10}R^{11}$, $—C(=O)R^{10}$, $—C(O)OR^{10}$, $—OC(=O)R^{10}$, $—NR^{10}C(=O)OR^{13}$, $—NR^{10}C(=O)R^{11}$, $—C(=O)NR^{10}R^{11}$, $—SR^{10}$, $—S(O)R^{13}$, $—SO_2R^{13}$, $—SO_2NHC(=O)R^{10}$, $—NR^{10}C(=O)NR^{11}R^{12}$, $—NR^{10}C(NCN)NR^{11}R^{12}$, $—OR^{10}$, alkyl, cycloalkyl, alkenyl, alkynyl, aryl, heteroaryl, arylalkyl, heteroarylalkyl, heterocyclyl, heterocyclylalkyl, and substituted forms thereof.

Scheme XIII

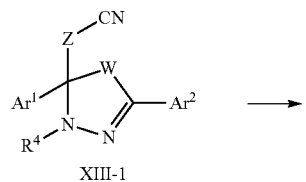

XIII-1

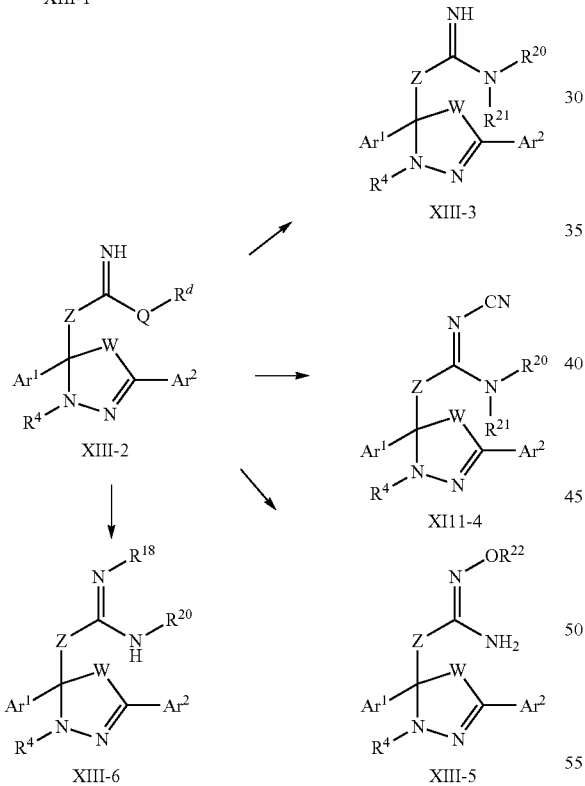

benzene. In certain embodiments, XIII-1 is subjected to anhydrous ethanolic HCl at 0° C. and allowed to warm to room temperature to afford the hydrochloride salt of XIII-2 wherein Q is oxygen and $R^d$ is ethyl. XIII-2 can then be converted to amidine XIII-3 by treatment with ammonia or the appropriate amine in ethanol, methanol or other appropriate solvent. In certain embodiments, XIII-2 is treated with an amine in methanol at room temperature to afford XIII-3 or a tautomer thereof. XIII-4 can be obtained by subjecting the hydrochloride salt XIII-2 to cyanamide in alcoholic solvent, followed by treatment with triethylamine or other suitable base and the appropriate amine. Alternatively, XIII-4 can be generated from XIII-3 by treatment with cyanogen bromide or cyanogen chloride and triethylamine or other suitable base in an appropriate solvent such as ethanol, acetonitrile, chloroform or DMF. XIII-5 is synthesized from XIII-2 by treatment with an alkoxyamine, hydroxylamine, or a salt thereof in the presence of triethylamine or other suitable base in ethanol, methanol, or other suitable solvent. In certain embodiments, XIII-2, wherein Q is oxygen and $R^d$ is ethyl is treated with the appropriate alkoxyamine hydrochloride in ethanol at room temperature to afford XIII-5 wherein $R^{18}$ is alkyl. XIII-6 can be produced from XIII-2 by subjecting XIII-2 to the appropriate mono-substituted amine at room temperature or elevated temperature in ethanol, methanol, or other appropriate solvent.

Scheme XIV

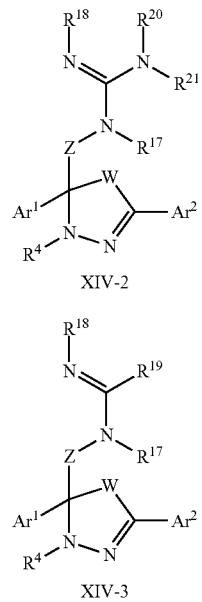

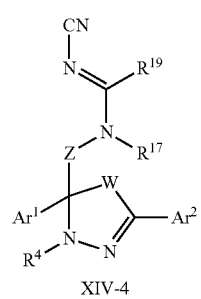

XIV-4

Scheme XIII illustrates a method of preparing compounds of the Formulas XIII-4, XIII-5, XIII-6 and XIII-7. XIII-1 can be synthesized in a manner similar to that previously described in the above Schemes. Nitrile XIII-1 can be converted to imidate XIII-2 wherein Q is oxygen by treatment with an anhydrous solution of HCl in methanol, ethanol or other appropriate alcohol at lowered or ambient temperatures. XIII-1 can be converted to thioimidate XIII-2 wherein Q is sulfur by treatment with HCl and the appropriate thiol in neat thiol or a suitable solvent such as methanol, ethanol, ether or Scheme XIV illustrates a method of preparing compounds of the Formulas XIV-2, XIV-3 and XIV-4. Amines of the formula XIV-1 are prepared in a manner similar to that described in the above Schemes. Amine XIV-1 can be converted to XIV-2 by treatment with a guanidinylating reagent such as, but not limited to, a substituted or unsubstituted S-methylisothiourea, carbodiimide, 3,5-dimethyl-1H-pyrazole-1-carboxamidine or aminoiminomethanesulfonic acid reagent in an appropriate solvent and at elevated temperature if necessary. Alternatively, XIV-2 can be prepared by subjecting XIV-1 to a N-protected guanidinylating reagent such as, but not limited to, di-Boc-S-methylisothiourea, di-CBz-triflylguanidine, or N,N-bis(tert-butoxycarbonyl)-1H-pyrazole-1-carboxamidine in a suitable solvent followed by subsequent removal of the protecting groups under the appropriate conditions to provide XIV-2 or a tautomer thereof. In certain embodiments, amine XIV-1 is treated with N,N'-bis(tert-butoxycarbonyl)-1H-pyrazole-1-carboxamidine in tetrahydrofuran, followed by treatment with hydrochloric acid in dioxane to remove the tert-butoxycarbonyl protecting groups to afford XIV-2 or a tautomer thereof wherein $R^{18}$, $R^{20}$ and $R^{21}$ are hydrogen. Compound XIV-3 can be obtained from amine XIV-1 by treatment with the appropriate imidate or imidate salt in combination with a suitable base, in an alcoholic solvent at elevated temperature. In certain embodiments, amine XIV-1 is treated with the hydrochloride salt of an ethyl imidate and triethylamine in refluxing anhydrous ethanol to afford XIV-3 or a tautomer thereof. Compound XIV-4 is prepared by treatment of amine XIV-1 with the appropriate cyanoimidate or cyanoimidate salt in combination with a suitable base, in an alcoholic solvent. In certain embodiments, amine XIV-1 is treated with an N-cyano ethyl imidate hydrochloride and triethylamine in anhydrous ethanol to afford XIV-4 or a tautomer thereof.

Scheme XV

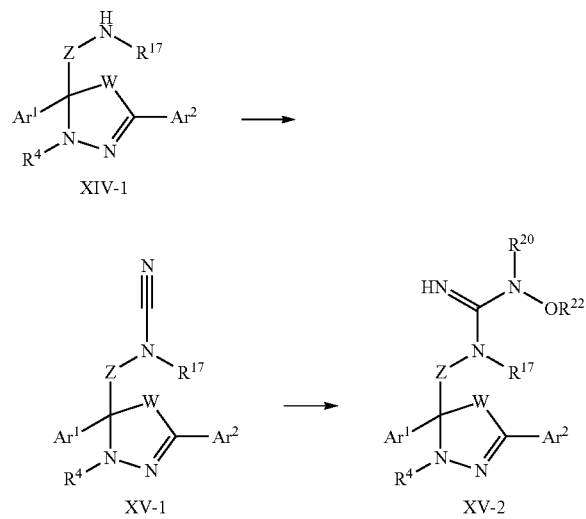

Scheme XV illustrates a method of preparing compounds of the Formula XV-2. Amine XIV-1 can be converted to compound XV-1 by treatment with cyanogen bromide or cyanogen chloride in the presence of a suitable base and appropriate solvent. In certain embodiments, amine XIV-1 is treated with cyanogen bromide and triethylamine in methylene chloride. Compound XV-2 can be prepared by treatment of compound XV-1 with excess of an alkoxyamine or alkoxyamine salt in the presence of an appropriate base in a suitable solvent optionally at elevated temperatures. In certain embodiments, XV-1 is treated with excess alkoxyamine hydrochloride salt and triethylamine in ethanol at reflux temperature to provide XV-2 or a tautomer thereof.

Scheme XVI

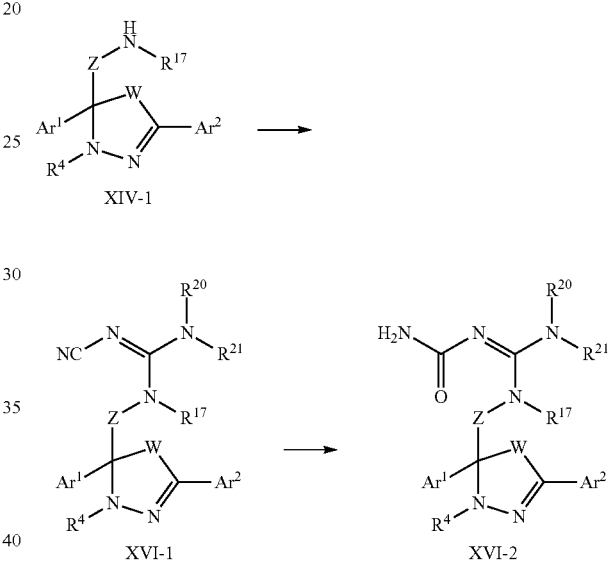

Scheme XVI illustrates a method of preparing compounds of the Formulas XVI-1 and XVI-2. Compound XVI-1 can be prepared in one step from amine XIV-1 by treatment with a cyano-guanidinylating reagent such as, but not limited to, an N-cyanocarbamimidate, an S-alkyl-N-cyanocarbamimidothioate, or dicyanamide salt. Alternatively, compound XVI-1 can be synthesized in a two-step procedure from XIV-1 by initial treatment with a reagent including, but not limited to, an N-cyanocarbonimidate or an N-cyanocarbonimidodithioate, optionally in the presence of a suitable base, followed by subsequent treatment with ammonia or the appropriate amine. In certain embodiments, the hydrochloride salt of amine XIV-1 is subjected to diphenylcyanocarbonimidate and triethylamine in isopropanol at room temperature, followed by treatment with ammonia or the appropriate amine in methanol at reflux temperature. Compound XVI-2 can be prepared by treatment of compound XVI-1 with acid and water in a suitable solvent. In certain embodiments, compound XVI-1 is treated with hydrochloric acid in methanol and water to provide compound XVI-2 or a tautomer thereof.

Scheme XVII

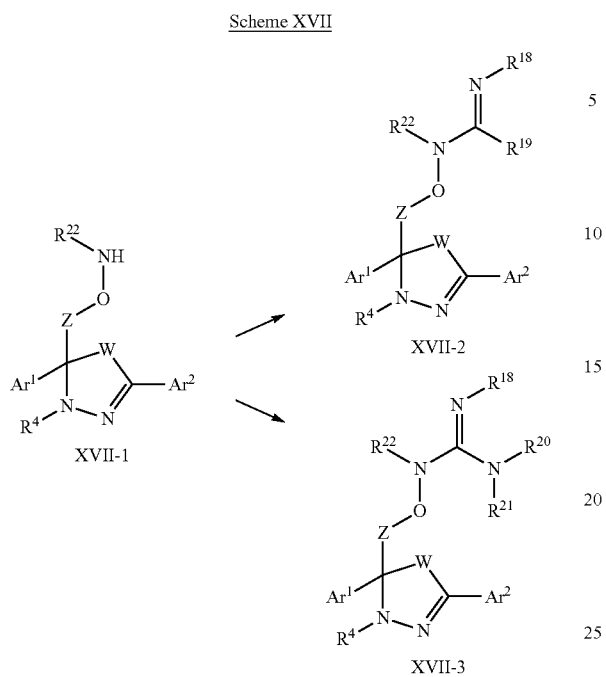

Scheme XVIII

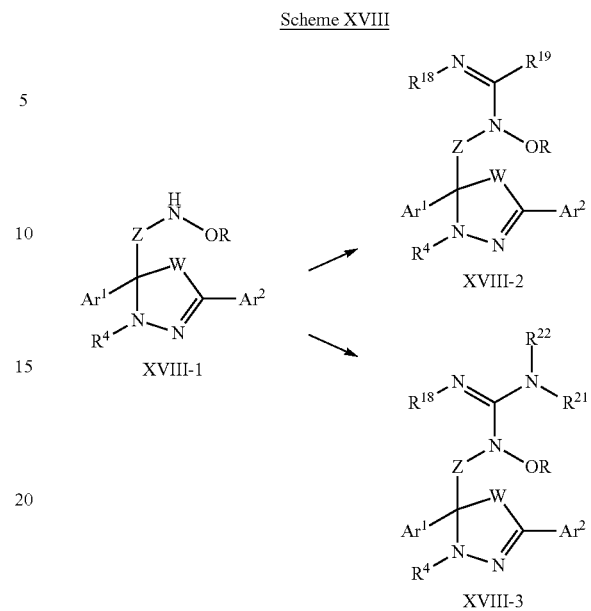

Scheme XVII illustrates a method of preparing compounds of the Formulas XVII-2 and XVII-3. Alkoxyamines of the formula XVII-I can be prepared by a similar route to the preparation of amines of the formula XIV-1 using the appropriate N-protected ketone precursor. Compound XVII-2 can be prepared by treatment of alkoxyamine XVII-1 with the appropriate imidate or imidate salt in combination with a suitable base, in an alcoholic solvent at elevated temperature. In certain embodiments, alkoxyamine XVII-1 is treated with the hydrochloride salt of an ethyl imidate and triethylamine in refluxing absolute ethanol to afford XVII-2 or a tautomer thereof. Compound XVII-3 can be prepared by treatment of alkoxyamine XVII-1 with a guanidinylating reagent such as, but not limited to, a substituted or unsubstituted S-methylisothiourea, carbodiimide, 3,5-dimethyl-1H-pyrazole-1-carboxamidine or aminoiminomethanesulfonic acid reagent in the appropriate solvent and at elevated temperature if necessary. Alternatively, XVII-3 can be prepared by subjecting XVII-1 to a N-protected guanidinylating reagent such as, but not limited to, di-Boc-S-methylisothiourea, di-CBz-trifylguanidine, or N,N-bis(tert-butoxycarbonyl)-1H-pyrazole-1-carboxamidine in a suitable solvent followed by removal of the protecting groups under the appropriate conditions to provide XVII-3 or a tautomer thereof. In certain embodiments, alkoxyamine XVII-1 is treated with N,N-bis(tert-butoxycarbonyl)-1H-pyrazole-1-carboxamidine in tetrahydrofuran, followed by treatment with hydrochloric acid in dioxane to remove the tert-butoxycarbonyl protecting groups to afford XVII-3 or a tautomer thereof wherein $R^{18}$, $R^{20}$ and $R^{21}$ are hydrogen.

Scheme XVIII illustrates a method of preparing compounds of the Formulas XVIII-2 and XVIII-3. Alkoxyamines of the formula XVIII-I can be prepared by a similar route to the preparation of amines of the formula XIV-1 using the appropriate N-protected ketone precursor. Compound XVIII-2 can be prepared by treatment of alkoxyamine XVIII-1 with the appropriate imidate or imidate salt in combination with a suitable base, in an alcoholic solvent at elevated temperature. In certain embodiments, alkoxyamine XVIII-1 is treated with the hydrochloride salt of an ethyl imidate and triethylamine in refluxing absolute ethanol to afford XVIII-2 or a tautomer thereof. Compound XVIII-3 can be prepared by treatment of alkoxyamine XVIII-1 with a guanidinylating reagent such as, but not limited to, a substituted or unsubstituted S-methylisothiourea, carbodiimide, 3,5-dimethyl-1H-pyrazole-1-carboxamidine or aminoiminomethanesulfonic acid reagent in the appropriate solvent and at elevated temperature if necessary. Alternatively, XVIII-3 can be prepared by subjecting XVIII-1 to a N-protected guanidinylating reagent such as, but not limited to, di-Boc-S-methylisothiourea, di-CBz-trifylguanidine, or N,N-bis(tert-butoxycarbonyl)-1H-pyrazole-1-carboxamidine in a suitable solvent followed by removal of the protecting groups under the appropriate conditions to provide XVIII-3 or a tautomer thereof. In certain embodiments, alkoxyamine XVIII-1 is treated with N,N-bis(tert-butoxycarbonyl)-1H-pyrazole-1-carboxamidine in tetrahydrofuran, followed by treatment with hydrochloric acid in dioxane to remove the tert-butoxycarbonyl protecting groups to afford XVIII-3 wherein $R^{18}$, $R^{20}$ and $R^{21}$ are hydrogen.

Scheme XIX

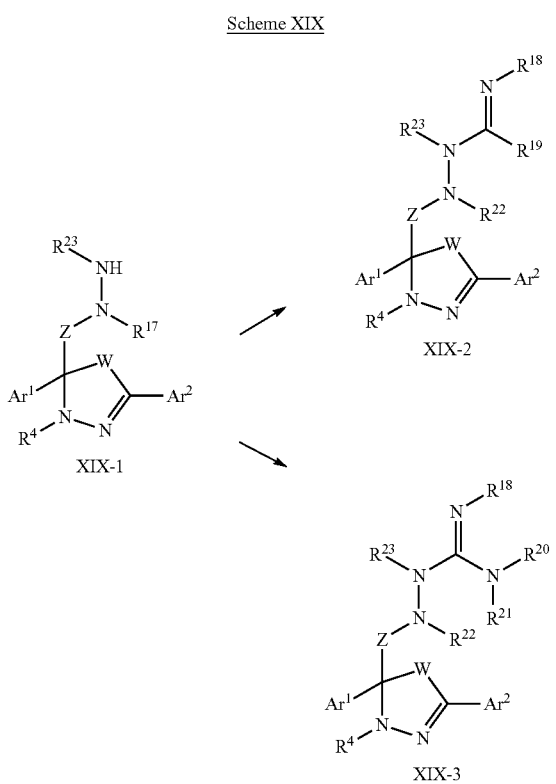

Scheme XIX illustrates a method of preparing compounds of the Formulas XIX-2 and XIX-3. Hydrazines of the formula XIX-1 can be prepared by a similar route to the preparation of amines of the formula XIV-1 using the appropriate N-protected ketone precursor. Compound XIX-2 can be prepared by treatment of hydrazine XIX-1 with the appropriate imidate or imidate salt in combination with a suitable base, in an alcoholic solvent at elevated temperature. In certain embodiments, hydrazine XIX-1 is treated with the hydrochloride salt of an ethyl imidate and triethylamine in refluxing absolute ethanol to afford XIX-2 or a tautomer thereof. Compound XIX-3 can be prepared by treatment of hydrazine XIX-1 with a guanidinylating reagent such as, but not limited to, a substituted or unsubstituted S-methylisothiourea, carbodiimide, 3,5-dimethyl-1H-pyrazole-1-carboxamidine or aminoiminomethanesulfonic acid reagent in the appropriate solvent and at elevated temperature if necessary. Alternatively, XIX-3 can be prepared by subjecting XIX-1 to a N-protected guanidinylating reagent such as, but not limited to, di-Boc-S-methylisothiourea, di-CBz-trifylguanidine, or N,N-bis(tert-butoxycarbonyl)-1H-pyrazole-1-carboxamidine in a suitable solvent followed by removal of the protecting groups under the appropriate conditions to provide XIX-3 or a tautomer thereof. In certain embodiments, hydrazine XIX-1 is treated with N,N'-bis(tert-butoxycarbonyl)-1H-pyrazole-1-carboxamidine in tetrahydrofuran, followed by treatment with hydrochloric acid in dioxane to remove the tert-butoxycarbonyl protecting groups to afford XIX-3 wherein $R^{18}$, $R^{20}$ and $R^{21}$ are hydrogen.

In the preparation of some analogues such as described in Schemes I-XIX, the use of appropriate protecting groups for functionality contained within the various substituents may be necessary. In these cases, deprotection of said functionality can be accomplished using standard methods known by and available to those skilled in the art.

The compounds of the invention find use in a variety of applications. As will be appreciated by those skilled in the art, mitosis may be altered in a variety of ways. That is, one can affect mitosis either by increasing or decreasing the activity of a component in the mitotic pathway. Stated differently, mitosis may be affected (e.g., disrupted) by disturbing equilibrium, either by inhibiting or activating certain components. Similar approaches may be used to alter meiosis.

In one embodiment, the compounds of the invention are used to modulate mitotic spindle formation, thus causing prolonged cell cycle arrest in mitosis. The term "modulate" as used herein means altering mitotic spindle formation, including increasing and decreasing spindle formation. The term "mitotic spindle formation" as used herein refers to organization of microtubules into bipolar structures by mitotic kinesins. "Mitotic spindle dysfunction" refers to mitotic arrest and monopolar spindle formation.

The compounds of the invention are useful to bind to and/or modulate the activity of a mitotic kinesin. In an embodiment, the mitotic kinesin is a member of the bimC subfamily of mitotic kinesins as described in U.S. Pat. No. 6,284,480, which is incorporated herein by reference. In a further embodiment, the mitotic kinesin is human KSP, although the activity of mitotic kinesins from other organisms may also be modulated by the compounds of the present invention. In this context, modulate means either increasing or decreasing spindle pole separation, causing malformation, i.e., splaying, of mitotic spindle poles, or otherwise causing morphological perturbation of the mitotic spindle. Also included within the definition of KSP for these purposes are variants and/or fragments of KSP. In addition, other mitotic kinesins may be inhibited by the compounds of the present invention.

The compounds of the invention are useful for treating diseases and conditions caused by abnormal cell growth or cellular proliferation. Disease states which can be treated by the methods and compositions provided herein include, but are not limited to, cancer, autoimmune disease, arthritis, graft rejection, inflammatory bowel disease, and proliferation induced after medical procedures, including, but not limited to, surgery, angioplasty, and the like. It is appreciated that in some cases the cells may not be in a hyperproliferative or hypoproliferative state (abnormal state), but still require treatment. For example, during wound healing, cells may be proliferating "normally", but proliferation enhancement may be desired. Similarly, in the agriculture arena, cells may be in a "normal" state, but proliferation modulation may be desired to enhance a crop by directly enhancing growth of a crop, or by inhibiting the growth of a plant or organism which adversely affects the crop. Thus, in one embodiment, the invention herein includes application to cells or individuals that are afflicted or may eventually become afflicted with any one of these disorders or states.

The invention also provides pharmaceutical compositions for treating a hyperproliferative disorder in a mammal, which comprise a therapeutically effective amount of a compound of the present invention, or a pharmaceutically acceptable salt, prodrug, metabolite or solvate thereof, and a pharmaceutically acceptable carrier. In one embodiment, said pharmaceutical composition is for the treatment of a hyperproliferative disorder such as cancer, including, but not limited to, skin, brain, lung, squamous cell, bladder, gastric, pancreatic, breast, head, neck, renal, kidney, ovarian, prostate, colorectal, esophageal, testicular, gynecological, cardiac, liver, bone, meninges, spinal cord, blood, skin, adrenal and thyroid cancer.

The compounds of the present invention may also be useful as antifungal agents, by modulating the activity of the fungal members of the bimC kinesin subgroup, as described in U.S. Pat. No. 6,284,480.

The invention also relates to a method of treating a hyperproliferative disorder in a mammal, comprising administering to said mammal a therapeutically effective amount of a compound of the present invention, or a pharmaceutically acceptable salt, prodrug, metabolite or solvate thereof. In one embodiment, said method relates to the treatment of cancer such as brain, lung, squamous cell, bladder, gastric, pancreatic, breast, head, neck, renal, kidney, ovarian, prostate, colorectal, esophageal, testicular, gynecological, cardiac, liver, bone, meninges, spinal cord, blood, skin, adrenal or thyroid cancer.

Patients that can be treated with compounds of the present invention, or pharmaceutically acceptable salts, prodrugs, metabolites or solvates of said compounds, according to the methods of this invention include, for example, patients that have been diagnosed as having lung cancer, bone cancer, CMML, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, testicular, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

The terms "abnormal cell growth" and "hyperproliferative disorder" are used interchangeably in this application and, unless otherwise indicated, refer to cell growth that is independent of normal regulatory mechanisms (e.g., loss of contact inhibition). This includes, but is not limited to, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The term "treating," as used herein, unless otherwise indicated, means reversing, alleviating, inhibiting the progress of, or preventing the disorder or condition to which such term applies, or one or more symptoms of such disorder or condition. The term "treatment," as used herein, unless otherwise indicated, refers to the act of treating as "treating" is defined immediately above. "Treating" is intended to mean at least the mitigation of a disease condition in a mammal, such as a human, and includes, but is not limited to, modulating and/or inhibiting the disease condition; and/or alleviating the disease condition.

The compounds of this invention may be used alone or in combination with other drugs and therapies used in the treatment of disease states which would benefit from the inhibition of mitotic kinesins. Accordingly, another aspect of this invention provides a method for treating a hyperproliferative disorder in a mammal that comprises administering to said mammal a therapeutically effective amount of a compound of the present invention, or a pharmaceutically acceptable salt, prodrug, metabolite or solvate thereof, in combination with an anti-tumor agent such as, but not limited to:

(i) antiproliferative/anti-neoplastic drugs and combinations thereof, as used in medical oncology, such as alkylating agents (for example, cisplatin, carboplatin, cyclophosphamide, nitrogen mustard, melphalan, chlorambucil, busulphan and nitrosoureas); anti-metabolites (for example, antifolates such as such as fluoropyrimidines like 5-fluorouracil and tegafur, raltitrexed, methotrexate, cytosine arabinside, hydroxyurea, or, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid); antitumor antibiotics (for example, anthracyclines like adriamycin, bleomycin, doxorubicin, daunomycin, epirubicin, idarubicin, mitomycin-C, dactinomycin and mithramycin); antimitotic agents (for example, vinca alkaloids like vincristine, vinblastine, vindesine and vinorelbine and taxoids like taxol and taxotere); and topoisomerase inhibitors (for example epipodophyllotoxins like eptoposide and teniposide, amsacrine, topotecan and campothecin);

(ii) cytostatic agents such as anti-estrogens (for example, tamoxifen, toremifene, raloxifene, droloxifene and iodoxyfene), estrogen receptor down regulators (for example, fulvestratrant), anti-androgens (for example, bicalutamide, flutamide, nilutamide, cyproxerone acetate and Casodex™ (4'-cyano-3-(4-fluorophenylsulphonyl)-2-hydroxy-2-methyl-3'-(trifluoromethyl)propionanilide)), LHRH antagonists or LHRH agonists (for example, goserelin, leuporelin and buserelin), progestogens (for example, megestrol acetate), aromatase inhibitors (for example, asanastrozole, letrozole, vorazole and exemestane) and inhibitors of 5α-reductase such as finasteride;

(iii) agents which inhibit cancer cell invasion (for example, metalloproteinase inhibitors like marimastat and inhibitors of urokinase plasminogen activator receptor function);

(iv) inhibitors of growth factor function like growth factor antibodies, growth factor receptor antibodies (for example, the anti-erbB2 antibody trastumuzab [Herceptin™] and the anti-erbB1 antibody cetuximab [C225]), farnesyl transferase inhibitors, tyrosine kinase inhibitors and serine-threonine kinase inhibitors (for example, inhibitors of the epidermal growth factor family tyrosine kinases such as N-(3-chloro-4-fluorophenyl)-7-methoxy-6-(3-morpholinopropoxy) quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), inhibitors of the platelet-derived growth factor family and inhibitors of the hepatocyte growth factor family;

(v) anti-angiogenic agents such as those which inhibit the effects of vascular endothelial growth factor (for example, the anti-vascular endothelial cell growth factor antibody bevacizumab [Avastin™], compounds such as those disclosed in PCT Publication Nos. WO 97/22596, WO 97/30035, WO 97/32856, and WO 98/13354) and compounds that work by other mechanisms (for example, linomide, inhibitors of integrin αvβ3 function, MMP inhibitors, COX-2 inhibitors and angiostatin);

(vi) vascular damaging agents such as Combretastatin A4 and compounds disclosed in PCT Publication Nos. WO 99/02166, WO 0/40529, WO 00/41669, WO 01/92224, WO 02/04434, and WO 02/08213;

(vii) antisense DNA or RNA therapies (for example, those which are directed to the targets listed above such as ISIS 2503, and anti-ras antisense);

(viii) gene therapy approaches, including for example GVAX™, approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy;

(ix) interferon;

(x) immunotherapy approaches, including for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches to using transfected immune cells such as cytokine-transfected dendritic cells, approaches using cytokine-transfected tumor cell lines and approaches using anti-idiotypic antibodies; and (xi) miscellaneous agents such as intercalating antibiotics, signal transduction inhibitors, cell cycle inhibitors, enzyme inhibitors, retinoid receptor modulators, proteasome inhibitors, biological response modifiers, anti-hormones, targeted antibodies, HMG-CoA reductase inhibitors, and prenyl-protein transferase inhibitors.

According to this aspect of the invention there is also provided a pharmaceutical composition comprising a compound of Formula I as defined herein and an additional anti-tumor agent as defined herein for the conjoint treatment of abnormal cell growth. Such conjoint treatment may be achieved by way of the simultaneous, sequential or separate dosing of the individual components of treatment. Such compositions employ the compounds of this invention within the dose ranges described herein and the additional anti-tumor agent within its approved dose range This invention also relates to a pharmaceutical composition for inhibiting abnormal cell growth in a mammal which comprises an amount of a compound of Formula I or a pharmaceutically acceptable salt, solvate, metabolite or prodrug thereof, in combination with an amount of a chemotherapeutic, wherein the amounts of the compound of Formula I or pharmaceutically acceptable salt, solvate, metabolite or prodrug thereof, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, anti-androgens, targeted antibodies, HMG-CoA reductase inhibitors, and prenyl-protein transferase inhibitors.

This invention further relates to a method for inhibiting abnormal cell growth in a mammal or treating a hyperproliferative disorder which comprises administering to the mammal an amount of a compound of Formula I or a pharmaceutically acceptable salt, metabolite, solvate or prodrug thereof, in combination with radiation therapy, wherein the amounts of the compound of Formula I or pharmaceutically acceptable salt, metabolite, solvate or prodrug thereof, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

This invention further provides a method for inhibiting proliferation of cells, comprising contacting said cells with an effective amount of a compound of Formula I or a solvate or pharmaceutically acceptable salt thereof, or a pharmaceutical composition comprising a compound of Formula I.

It is believed that the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation, which comprises administering to the mammal an amount of a compound of Formula I or a pharmaceutically acceptable salt, solvate, metabolite or prodrug thereof, which amount is effective in sensitizing abnormal cells to radiation treatment. The amount of the compound of Formula I or pharmaceutically acceptable salt, solvate, metabolite or prodrug thereof, to be used in this method can be determined according to means for ascertaining effective amounts of such compounds as described herein or by methods know to those skilled in the art.

The compounds of this invention may be used alone or in combination with other drugs and therapies used in the treatment of disease states which would benefit from the inhibition of KSP kinesin. For example, a compound of Formula I or a pharmaceutically acceptable salt, solvate, metabolite or prodrug thereof may be administered to a mammal in need thereof in combination with one or more other anti-tumor substances, including, but not limited to, mitotic inhibitors such as vinblastine; alkylating agents such as cis-platin, carboplatin and cyclophosphamide; anti-metabolites such as 5-fluorouracil, cytosine arabinside and hydroxyurea; one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid (also known as ZD 1694 and ICI 1694); antisense RNA and DNA oligonucleotides such as G3139, ODN698, and GEM231; growth factor inhibitors; signal transduction inhibitors, such as agents that can inhibit EGFR (epidermal growth factor receptor) responses, such as EGRF antibodies, EGF antibodies and molecules that are EGFR inhibitors such as the compounds ZD-1839 (AstraZeneca) and BIBX-1382 (Boehringer Ingelheim); VEGF inhibitors such as SU-6668 (Sugen, Inc. of South San Francisco, Calif.) or the anti-VEGF monoclonal antibody of Genentech, Inc. of South San Francisco, Calif.; cell cycle inhibitors; intercalating antibiotics such as adriamycin and bleomycin; enzymes, for example, interferon; retinoid receptor modulators such as bexarotene, ILX23-7553, and N-4-carboxyphenyl retinamide; proteasome inhibitors such as lactacystin and bortezomib; topoisomerase inhibitors such as topotecan, rebutecan and teniposide; anti-hormone such as anti-estrogens such as Nolvadex™ (tamoxifen); anti-androgens such as Casodex™ (4'-cyano-3-(4-fluorophenylsulphonyl)-2-hydroxy-2-methyl-3'-(trifluoromethyl)propionanilide); monoclonal antibody targeted therapeutic agents which have cytotoxic agents or radioisotopes attached to a cancer cell specific or target cell specific monoclonal antibody; inhibitors of HMG-CoA reductase (3-hydroxy-3-methylglutaryl-CoA reductase) such as simvastatin (ZOCOR®) and atorvastatin (LIPITOR®); prenyl-protein transferase inhibitors; inhibitors of protein kinases that transduce cell cycle checkpoint signals (e.g., ART, ARM, the Chk1 and Chk2 kinases, cdk and cdc kinase) such as 7-hydroxystaurosporin, flavopiridol and CYC202 (Cyclacel); and inhibitors of kinases involved in mitotic progression where such kinases include, but are not limited to, Polo-like kinases and aurora kinase. Such conjoint treatment may be achieved by way of simultaneous, sequential or separate dosing of the individual components of treatment.

The compounds of the present invention may also be used in combination with inhibitors of mitotic kinesins. Examples of inhibitors of mitotic kinesins, and in particular the human mitotic kinesin KSP, are described in PCT Publication Nos. WO 00/130,768, WO 01/30768, WO 01/98278, WO 03/050,064, WO 03/050,122, WO 03/049,527, WO 03/049,679, WO 03/049,678, WO 03/39460 WO 03/079,973, WO 03/088,903, WO 03/094,839, WO 03/097,053, WO 03/099,211, WO 03/099,286, WO 03/103,575, WO 03/105,855, WO 03/106,426, WO 04/032,840, WO 04/034,879, WO 04/037,171, WO 04/039,774, WO 04/055,008, WO 04/058,148, WO 04/058,700 and WO 04/064,741.

The compounds of the present invention may also be used in the treatment of cancer in combination with compounds that are not anti-tumor compounds. For example, a compound of this invention may be applied in combination with one or more substances, including, but not limited to, PPAR-γ and PPAR-δ agonists such as proglitazone, rosiglatazone, gene therapy agents, and inhibitors of inherent multi-drug resistance (e.g. p-glycoprotein inhibitors).

A compound of the present invention may also be employed in conjunction with anti-emetic agents to treat nausea or emesis, by way of simultaneous, sequential or separate dosing of the individual components of treatment.

A compound of the present invention may also be administered in combination with an agent useful in the treatment of anemia, such as epoetin, by way of simultaneous, sequential or separate dosing of the individual components of treatment.

A compound of the present invention may also be administered in combination with an agent useful in the treatment of neutropenia, by way of simultaneous, sequential or separate dosing of the individual components of treatment. Such a neutropenia treatment agent is, for example, a hematopoietic growth factor, which regulates the production and function of neutrophils such as a human granulocyte colony stimulating factor, (G-CSF). An example of a G-CSF is filgrastim.

A compound of the present invention may also be administered in combination with an immunologic-enhancing drug, such as levamisole, isoprinosine and Zadaxin, by way of simultaneous, sequential or separate dosing of the individual components of treatment.

Although the compounds of Formula I are primarily of value as therapeutic agents for use in warm-blooded animals (including humans), they are also useful whenever it is required to inhibit the effects of KSP kinesin. Thus, they are also useful as pharmacological standards in the development of new biological tests and in the search for new pharmacological agents.

The invention also provides pharmaceutical compositions comprising a compound of Formula I, or a pharmaceutically acceptable salt, metabolite, solvate or prodrug thereof, and methods of use thereof for inhibiting abnormal cell growth in a mammal, comprising administering to a mammal in need thereof an amount of a compound of Formula I or a pharmaceutically acceptable salt, solvate, metabolite, or prodrug, thereof, alone or in combination with an amount of one or more substances selected from anti-angiogenesis agents, signal transduction inhibitors, and antiproliferative agents, in amounts effective to inhibit abnormal cell growth.

For example, anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound or pharmaceutical compositions of the present invention. Examples of useful COX-II inhibitors include CELEBREX™ (alecoxib), valdecoxib, etoricoxib, lumiracoxib and rofecoxib). Examples of useful matrix metalloprotienase inhibitors are described in PCT Publication Nos. WO 96/33172, WO 96/27583, WO 98/07697, WO 98/03516, WO 98/34918, WO 98/34915, WO 98/33768, WO 98/30566, WO 90/05719, WO 99/52910, WO 99/52889, WO 99/29667, U.S. Pat. No. 5,863,949, and U.S. Pat. No. 5,861,510. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13). Such conjoint treatment may be achieved by way of the simultaneous, sequential or separate dosing of the individual components of treatment. Such combination products employ the compounds of this invention within the dose range described herein and the other pharmaceutically active agent within its approved dose range.

It will be understood that the specific dosage level and frequency of dosage for any particular subject may be varied and will depend upon a variety of factors including the activity of the specific compound of Formula I, the species, age, body weight, general health, sex and diet of the subject, the mode and time of administration, rate of excretion, drug combination, and severity of the particular condition, but can nevertheless be routinely determined by one skilled in the art.

This invention also provides compounds of Formula I for use in therapy. An additional aspect of the invention is the use of a compound of Formula I for the preparation of a medicament for use as a kinesin inhibitor.

In order to use a compound of the Formula I, or a pharmaceutically acceptable salt, solvate, metabolite or prodrug thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the Formula I, or a pharmaceutically acceptable salt, solvate, metabolite or prodrug thereof as defined herein, in association with a pharmaceutically acceptable diluent or carrier.

To prepare the pharmaceutical compositions according to this invention, a therapeutically or prophylactically effective amount of a compound of Formula I or pharmaceutically acceptable salt, solvate, metabolite or prodrug thereof (alone or together with an additional therapeutic agent as disclosed herein) is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. Examples of suitable carriers include any and all solvents, dispersion media, adjuvants, coatings, antibacterial and antifungal agents, isotonic and absorption delaying agents, sweeteners, stabilizers (to promote long term storage), emulsifiers, binding agents, thickening agents, salts, preservatives, solvents, dispersion media, coatings, flavoring agents, and miscellaneous materials such as buffers and absorbents that may be needed in order to prepare a particular therapeutic composition. The use of such media and agents with pharmaceutically active substances is well known in the art. Except insofar as any conventional media or agent is incompatible with a compound of Formula I, its use in the therapeutic compositions and preparations is contemplated. Supplementary active ingredients can also be incorporated into the compositions and preparations as described herein.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing).

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil. For example, compositions intended for oral use may also contain, for example, one or more coloring, sweetening, flavoring and/or preservative agents.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate), anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. For parenteral formulations, the carrier will usually comprise sterile water, aqueous sodium chloride solution, 1,3-butanediol, or any other suitable non-toxic parenterally-acceptable diluent or solvent. Other ingredients including those that aid dispersion may be included. Of course, where sterile water is to be used and maintained as sterile, the compositions and carriers must also be sterilized. Injectable suspensions may also be prepared, in which case appropriate liquid carriers, suspending agents and the like may be employed.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

Compositions for transdermal administration may be in the form of those transdermal skin patches that are well known to those of ordinary skill in the art.

For further information on formulations, see Chapter 25.2 in Volume 5 of Comprehensive Medicinal Chemistry (Corwin Hansch; Chairman of Editorial Board), Pergamon Press 1990.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. However, an effective dosage is in the range of about 0.001 to about 100 mg per kg body weight per day, preferably about 0.5 to about 35 mg/kg/day, in single or divided doses. For a 70 kg human, this would amount to about 0.0035 to 2.5 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press 1990.

The size of the dose for therapeutic or prophylactic purposes of a compound of Formula I will naturally vary according to the nature and severity of the conditions, the age and sex of the animal or patient and the route of administration, according to well known principles of medicine.

In another embodiment of the invention, an article of manufacture, or "kit", containing materials useful for the treatment of the disorders described above is provided. In one embodiment, the kit comprises a container comprising a composition of Formula I or a pharmaceutically acceptable solvate or salt thereof. The kit may further comprise a label or package insert on or associated with the container. Suitable containers include, for example, bottles, vials, syringes, blister pack, etc. The container may be formed from a variety of materials such as glass or plastic. The container holds a compound of Formula I or a pharmaceutically acceptable solvate or salt thereof, or a formulation thereof which is effective for treating the condition and may have a sterile access port (for example, the container may be an intravenous solution bag or a vial having a stopper pierceable by a hypodermic injection needle). The label or package insert indicates that the composition is used for treating the condition of choice, such as cancer. In one embodiment, the label or package inserts indicates that the composition comprising a compound of Formula I or a pharmaceutically acceptable solvate or salt thereof, can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I or a pharmaceutically acceptable solvate or salt thereof, and, if present, the second pharmaceutical formulation. For example, if the kit comprises a first composition comprising a compound of Formula I or a pharmaceutically acceptable solvate or salt thereof, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, or a pharmaceutically acceptable solvate or salt thereof, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, an article of manufacture may comprise (a) a first container with a compound of Formula I or a pharmaceutically acceptable solvate or salt thereof, contained therein; and optionally (b) a second container with a second pharmaceutical formulation contained therein, wherein the second pharmaceutical formulation comprises a second compound with anti-hyperproliferative activity. Alternatively, or additionally, the article of manufacture may further comprise a third container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet; however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Accordingly this invention also provides a kit for treating an abnormal cell growth condition, wherein said kit comprises a) a first pharmaceutical composition comprising a compound of this invention or a pharmaceutically acceptable salt thereof; and b) instructions for use.

In certain embodiments, the kit further comprises (c) a second pharmaceutical composition, wherein the second pharmaceutical composition comprises a second compound having anti-hyperproliferative activity. In certain embodiment comprising a second pharmaceutical composition, the kit further comprises instructions for the simultaneous, sequential or separate administration of said first and second pharmaceutical compositions to a patient in need thereof. In certain embodiments, said first and second pharmaceutical compositions are contained in separate containers. In other embodiments, said first and second pharmaceutical compositions are contained in the same container.

In certain embodiments, this invention provides a kit for treating an abnormal cell growth condition such as hyperproliferative disorder or a hypoproliferative disorder. In other embodiments, this invention provides a kit for treating an abnormal cell growth condition such as cancer, autoimmune disease, arthritis, graft rejection, inflammatory bowel disease, or proliferation induced after a medical procedure. In other embodiments, this invention provides a kit for treating a fungal or other eukaryote infection in a mammal.

Representative compounds of the present invention, which are encompassed by the present invention include, but are not limited to the compounds of the examples and the salts, solvates, metabolites or prodrugs thereof. The examples presented below are intended to illustrate particular embodiments of the invention, and are not intended to limit the scope of the specification or the claims in any way.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other KSP inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. Tetrahydrofuran (THF), N,N-dimethylformamide (DMF), dichloromethane (DCM), toluene, dioxane and 1,2-dichloroethane (DCE) were purchased from Aldrich in Sure seal bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters).

$^1$H-NMR spectra were recorded on a Varian instrument operating at 400 MHz. $^1$H-NMR spectra were obtained as CDCl$_3$ solutions (reported in ppm), using chloroform as the reference standard (7.25 ppm). Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

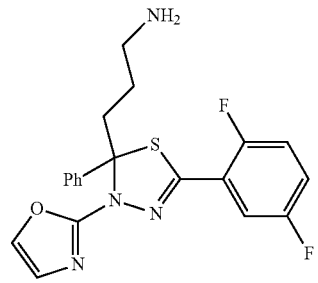 [SMILES: NCCCC1(c2ccccc2)SC(c2cc(F)ccc2F)=NN1c1ncco1]

3-(5-(2,5-difluorophenyl)-3-(oxazol-2-yl)-2-phenyl-2,3-dihydro-1,3,4-thiadiazol-2-yl)propan-1-amine Step A: di-tert-butyl 3-(5-(2,5-difluorophenyl)-2-phenyl-2,3-dihydro-1,3,4-thiadiazol-2-yl)propylaminodicarboxylate: A mixture of 2,4-difluorobenzothiohydrazide (1.57 g, 8.32 mmol) and di-tert-butyl 4-oxo-4-phenylbutylamino dicarboxylate (3.32 g, 9.15 mmol) in EtOH/DCM (20 mL/20 mL) was stirred at room temperature for 48 hours. The mixture was concentrated under reduced pressure and the residue was chromatographed (20:1 hexanes/EtOAc) to provide the product (3.12 g, 70%).

Step B: di-tert-butyl 3-(5-(2,5-difluorophenyl)-3-(1H-imidazole-1-carbonyl)-2-phenyl-2,3-dihydro-1,3,4-thiadiazol-2-yl)propylaminodicarboxylate: A mixture of di-tert-butyl 3-(5-(2,5-difluorophenyl)-2-phenyl-2,3-dihydro-1,3,4-thiadiazol-2-yl)propylaminodicarboxylate (0.49 g, 0.92 mmol) and carbonyldiimidazole (0.179 g, 1.11 mmol) in THF (9 mL) was heated to 70° C. for 16 hours. Two more equivalents of CDI were added and the mixture was heated to 75° C. for 1 hour. The reaction mixture was partitioned between dichloromethane (25 mL) and 0.2 M HCl (35 mL). The aqueous layer was extracted with dichloromethane (25 mL) and the combined organics were dried over Na$_2$SO$_4$, filtered, and concentrated under reduced pressure to provide the crude product (0.58 g, 100%) as a brown oil.

Step C: di-tert-butyl 3-(5-(2,5-difluorophenyl)-3-((2,2-dimethoxyethyl) carbamoyl)-2-phenyl-2,3-dihydro-1,3,4-thiadiazol-2-yl)propylaminodicarboxylate: To a solution of di-tert-butyl 3-(5-(2,5-difluorophenyl)-3-(1H-imidazole-1-carbonyl)-2-phenyl-2,3-dihydro-1,3,4-thiadiazol-2-yl)propylaminodicarboxylate (0.289 g, 0.461 mmol) in acetonitrile (3 mL) was added iodomethane (0.288 mL, 4.61 mmol). After stirring at room temperature for 4 hours, another 5 equivalents of MeI were added, and then again at 20 hours, 24 hours, and 28 hours (5 equivalents MeI at each time point). The mixture was concentrated under reduced pressure and the residue was dissolved in dichloromethane (5 mL). To this solution was added 2,2-dimethoxyethanamine (0.121 mL, 1.11 mmol). After stirring at room temperature for 16 hours, water (30 mL) was added and the mixture was extracted with dichloromethane (2×25 mL). The combined organics were dried over Na$_2$SO$_4$, filtered, and concentrated under reduced pressure to provide the product (0.270 g, 88%) as a brown oil.

Step D: tert-butyl 3-(5-(2,5-difluorophenyl)-3-((2-oxoethyl)carbamoyl)-2-phenyl-2,3-dihydro-1,3,4-thiadiazol-2-yl)propylcarbamate: To a solution of di-tert-butyl 3-(5-(2,5-difluorophenyl)-3-((2,2-dimethoxyethyl)carbamoyl)-2-phenyl-2,3-dihydro-1,3,4-thiadiazol-2-yl)propylaminodicarboxylate (0.258 g, 0.388 mmol) in THF/water (10 mL, 5:1) was added p-toluenesulfonic acid (0.060 g, 0.345 mmol). After heating to 70° C. for 16 hours, the mixture was diluted with ethyl acetate (100 mL) and washed with saturated NaHCO₃ (30 mL), brine (30 mL), dried over Na₂SO₄, filtered and concentrated under reduced pressure to provide the crude product (188 mg) as a brown film.

Step E: 3-(5-(2,5-difluorophenyl)-3-(oxazol-2-yl)-2-phenyl-2,3-dihydro-1,3,4-thiadiazol-2-yl)propan-1-amine: To a cooled (0° C.) solution of tert-butyl 3-(5-(2,5-difluorophenyl)-3-((2-oxoethyl)carbamoyl)-2-phenyl-2,3-dihydro-1,3,4-thiadiazol-2-yl)propylcarbamate (0.188 g, 0.363 mmol) in dichloromethane (15 mL) was added triphenylphosphine (0.475 g, 1.81 mmol) and 2,6-di-tert-butylpyridine (1.63 mL, 7.25 mmol) followed by 1,2-dibromo-1,1,2,2-tetrachloroethane (0.590 g, 1.81 mmol). After stirring at 0° C. for 45 minutes, a solution of DBU (1.63 mL, 10.9 mmol) in acetonitrile (15 mL) was added. The mixture was slowly warmed to room temperature. After stirring for 36 hours, the reaction mixture was concentrated under reduced pressure. The residue was dissolved in ethyl acetate (50 mL) and washed with 0.2 M HCl (30 mL). The aqueous layer was extracted with ethyl acetate (30 mL) and the combined organics were dried over Na₂SO₄, filtered, and concentrated under reduced pressure. The residue was chromatographed (20% ethyl acetate in hexanes) to provide the Boc-protected product. To this product dissolved in dichloromethane (0.5 mL) was added TFA (50 µL). After stirring at 0° C. for 30 minutes and at room temperature for 30 minutes, the mixture was concentrated under reduced pressure to provide the di-TFA salt product as pale yellow film. MS ESI (+) m/z 401 (M+1) detected; ¹H NMR (400 MHz, CDCl₃) δ 8.28 (br, 2H), 7.69 (m, 1H), 7.46 (m, 2H), 7.33 (m, 3H), 7.22 (m, 1H), 7.07 (m, 2H), 6.89 (m, 1H), 3.05 (m, 2H), 2.64 (m, 1H), 2.24 (m, 1H), 1.94 (m, 1H), 1.83 (m, 1H).

Example 2

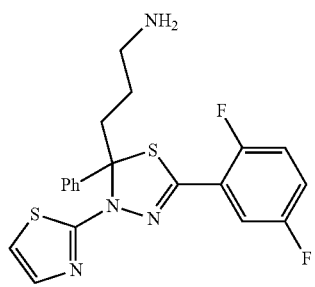 [SMILES: NCCCC1(c2ccccc2)SC(c2cc(F)ccc2F)=NN1c1nccs1]

3-(5-(2,5-difluorophenyl)-2-phenyl-3-(thiazol-2-yl)-2,3-dihydro-1,3,4-thiadiazol-2-yl)propan-1-amine Step A: di-tert-butyl 3-(3-carbamothioyl-5-(2,5-difluorophenyl)-2-phenyl-2,3-dihydro-1,3,4-thiadiazol-2-yl)propylaminodicarboxylate: A mixture of di-tert-butyl 3-(5-(2,5-difluorophenyl)-2-phenyl-2,3-dihydro-1,3,4-thiadiazol-2-yl)propylaminodicarboxylate (0.029 g, 0.054 mmol) and di(1H-imidazol-1-yl)methanethione (0.019 g, 0.11 mmol) in DMF (0.5 mL) was heated to 95° C. for 17 hours to provide a crude mixture containing the desired di-tert-butyl 3-(5-(2,5-difluorophenyl)-3-(1H-imidazole-1-carbonothioyl)-2-phenyl-2,3-dihydro-1,3,4-thiadiazol-2-yl)propylaminodicarboxylate. To this mixture was added ammonia (0.1 mL of 0.5 M solution in dioxane). After heating to 40° C. for 13 hours, concentrated aqueous ammonium hydroxide (5 drops) was added. After stirring at room temperature for 16 hours, the mixture was diluted with ethyl acetate (70 mL) and washed with brine (30 mL). The organic layer was dried over Na₂SO₄, filtered, and concentrated under reduced pressure. The residue was chromatographed (15% ethyl acetate in hexanes) to afford the product (5.8 mg) as a brown film.

Step B: 3-(5-(2,5-difluorophenyl)-2-phenyl-3-(thiazol-2-yl)-2,3-dihydro-1,3,4-thiadiazol-2-yl)propan-1-amine: To a solution of di-tert-butyl 3-(3-carbamothioyl-5-(2,5-difluorophenyl)-2-phenyl-2,3-dihydro-1,3,4-thiadiazol-2-yl)propylaminodicarboxylate (0.006 g, 0.010 mmol) in EtOH (1 mL) was added 2-chloroacetaldehyde (50% aqueous solution, 0.015 mL, 0.12 mmol). After heating to 80° C. for 16 hours, another 15 µL of the 2-chloroacetaldehyde solution was added followed by DIEA (0.041 mL, 0.23 mmol). After heating to 90° C. for 7 hours, the mixture was partitioned between ethyl acetate (25 mL) and saturated NaHCO₃ (30 mL). The aqueous layer was extracted with ethyl acetate (2×25 mL). The combined organics were washed with brine (30 mL), dried over Na₂SO₄, filtered, and concentrated under reduced pressure. The residue was chromatographed (10% ethyl acetate in hexanes) to provide 2.5 mg of the mono Boc-protected product as a yellow film. To this product dissolved in dichloromethane (0.5 mL) and cooled to 0° C. was added TFA (50 µL). After stirring at 0° C. for 2 hours, the mixture was concentrated under reduced pressure to provide the TFA salt product as a pale yellow film. MS ESI (+) m/z 417 (M+1) detected; ¹H NMR (400 MHz, CDCl₃) δ 8.56 (br, 1H), 7.59 (m, 1H), 7.38 (d, 2H, J=7 Hz), 7.31 (m, 3H), 7.06 (m, 4H), 6.65 (d, 1H, J=4 Hz), 3.36 (m, 1H), 3.00 (m, 2H), 2.60 (m, 1H), 2.21 (m, 1H), 1.83 (m, 1H).

The following were prepared similarly using the appropriate 2-haloketone:

Example 2A

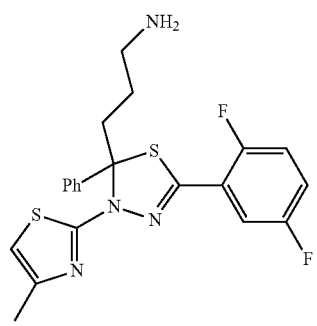 [SMILES: Cc1csc(N2N=C(c3cc(F)ccc3F)SC2(CCCN)c2ccccc2)n1]

3-(5-(2,5-difluorophenyl)-3-(4-methylthiazol-2-yl-2-phenyl-2,3-dihydro-1,3,4-thiadiazol-2-yl)propan-1-amine MS ESI (+) m/z 431 (M+1) detected; ¹H NMR (400 MHz, CDCl3) δ 8.58 (br, 3H), 7.67 (m, 2H), 7.41 (m, 3H), 7.07 (m, 2H), 6.19 (m, 1H), 3.71 (s, 3H), 3.42 (m, 1H), 3.10 (m, 1H), 2.68 (m, 1H), 2.32 (m, 2H), 1.32 (m, 1H).

Example 2B

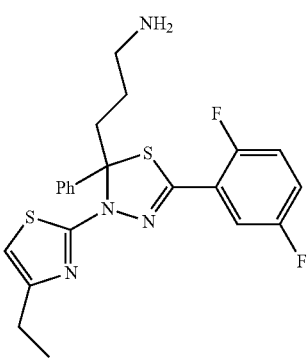 [SMILES: CCc1csc(N2N=C(c3cc(F)ccc3F)SC2(CCCN)c2ccccc2)n1]

3-(5-(2,5-difluorophenyl)-3-(4-ethylthiazol-2-yl)-2-phenyl-2,3-dihydro-1,3,4-thiadiazol-2-yl)propan-1-amine MS ESI (+) m/z 445 (M+1) detected; ¹H NMR (400 MHz, CDCl$_3$) δ 8.58 (br, 3H), 7.71 (m, 2H), 7.43 (m, 3H), 7.09 (m, 2H), 6.20 (m, 1H), 3.71 (m, 2H), 3.40 (m, 1H), 3.09 (m, 1H), 2.72 (m, 3H), 2.10 (m, 1H), 1.11 (m, 3H).

Example 3

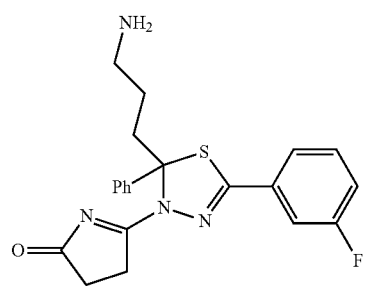 [SMILES: NCCCC1(c2ccccc2)SC(c2cccc(F)c2)=NN1C1=NC(=O)CC1]

5-(2-(3-aminopropyl)-5-(3-fluorophenyl)-2-phenyl-1,3,4-thiadiazol-3(2H)-yl)-3,4-dihydropyrrol-2-one To a solution of 5-ethoxy-3,4-dihydropyrrol-2-one (0.16 g, 1.3 mmol) in IPA/THF (2 mL/2 mL) was added tert-butyl 3-(5-(3-fluorophenyl)-2-phenyl-2,3-dihydro-1,3,4-thiadiazol-2-yl)propylcarbamate (0.052 g, 0.13 mmol) and acetic acid (0.1 mL). After heating to 90° C. for 5 hours in a sealed tube, the mixture was concentrated under reduced pressure. The residue was chromatographed (1:6 to 1:4 ethyl acetate/hexanes) to provide the Boc-protected product (0.026 g, 42%). To this product dissolved in dichloromethane (1 mL) was added TFA (1 mL). After stirring at room temperature for 30 minutes, the mixture was concentrated under high vacuum for 16 hours to provide the final product as the di-TFA salt. MS ESI (+) m/z 397 (M+1) detected; ¹H NMR (400 MHz, CDCl$_3$) δ 8.11 (br, 2H), 7.44 (m, 5H), 7.34 (m, 3H), 7.22 (m, 1H), 3.57 (m, 1H), 3.29 (m, 1H), 3.20 (m, 2H), 3.05 (m, 1H), 2.57 (m, 1H), 2.46 (m, 2H), 2.13 (m, 1H), 1.78 (m, 1H).

Example 4

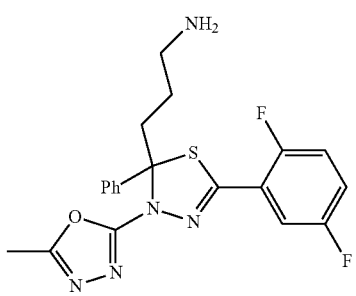 [SMILES: Cc1nnc(N2N=C(c3cc(F)ccc3F)SC2(CCCN)c2ccccc2)o1]

3-(5-(2,5-difluorophenyl)-3-(4,5-dihydrothiazol-2-yl)-2-phenyl-2,3-dihydro-1,3,4-thiadiazol-2-yl)propan-1-amine To a solution of di-tert-butyl 3-(5-(2,5-difluorophenyl)-2-phenyl-2,3-dihydro-1,3,4-thiadiazol-2-yl)propylaminodicarboxylate (0.182 g, 0.34 mmol) in THF (3 mL) was added di(1H-imidazol-1-yl)methanethione (0.091 g, 0.51 mmol). After heating to 70° C. for 2 hours, the mixture was cooled to room temperature and 2-bromoethanamine hydrobromide (0.69 g, 3.4 mmol) followed by acetic acid (0.061 g, 1.0 mmol) were added. After heating to 88° C. for 8 hours, the mixture was cooled to room temperature and chromatographed (1:20 to 1:10 ethyl acetate/hexanes) to provide the Boc-protected product (21 mg, 10%). To this product was added formic acid (1 mL). The mixture was stirred at room temperature for 1 hour and concentrated under reduced pressure to provide the final product as the formate salt. MS ESI (+) m/z 419 (M+1) detected; ¹H NMR (400 MHz, CDCl$_3$) δ 8.40 (br, 1H), 7.54 (m 1H), 7.35 (m, 4H), 7.27 (m, 2H), 7.03 (m, 2H), 4.08 (m, 1H), 3.89 (m, 1H), 3.22 (m, 3H), 2.94 (m, 2H), 2.47 (m, 1H), 2.14 (m, 1H), 1.80 (m, 1H).

Example 5

3-(5-(2,5-difluorophenyl)-3-(5-methyl-1,3,4-oxadiazol-2-yl)-2-phenyl-2,3-dihydro-1,3,4-thiadiazol-2-yl)propan-1-amine Step A: (5-(2,5-difluorophenyl)-2-(3-di-tert-butoxycarbonylaminopropyl)-2-phenyl-1,3,4-thiadiazol-3(2H)-yl)(1H-3-methylimidazolium-1-yl)methanone iodide: To a solution of di-tert-butyl 3-(5-(2,5-difluorophenyl)-2-phenyl-2,3-dihydro-1,3,4-thiadiazol-2-yl)propylaminodicarboxylate (0.335 g, 0.628 mmol) in THF (3 mL) was added di(1H-imidazol-1-yl)methanone (0.122 g, 0.753 mmol). After heating to 70° C. for 2 hours, the mixture was cooled to room temperature and concentrated under reduced pressure. The residue was dissolved in dichloromethane (5 mL) and washed with water (2×3 mL), dried over $Na_2SO_4$, and concentrated under reduced pressure. This residue was dissolved in acetonitrile (2 mL) and treated with iodomethane (0.446 g, 3.14 mmol) for 24 hours. The mixture was then concentrated under reduced pressure to afford the crude product.

Step B: N'-acetyl-2-(3-di-tert-butoxycarbonylaminopropyl)-5-(2,5-difluorophenyl)-2-phenyl-1,3,4-thiadiazole-3(2H)-carbohydrazide: To a solution of (5-(2,5-difluorophenyl)-2-(3-di-tert-butoxycarbonylaminopropyl)-2-phenyl-1,3,4-thiadiazol-3(2H)-yl)(1H-3-methylimidazolium-1-yl)methanone iodide (0.211 g, 0.274 mmol) and triethylamine (0.069 g, 0.0685 mmol) in dichloromethane (3 mL) was added acetohydrazide (0.041 g, 0.548 mmol). After stirring for 30 minutes, the mixture was partitioned between dichloromethane (10 mL) and saturated $NaHCO_3$ (5 mL). The aqueous layer was extracted with dichloromethane (10 mL). The combined organics were washed with brine (10 mL), dried over $Na_2SO_4$, and concentrated under reduced pressure. The residue was chromatographed (10:1 to 4:1 hexanes/ethyl acetate) to provide the final product (0.123 g, 71%).

Step C: 3-(5-(2,5-difluorophenyl)-3-(5-methyl-1,3,4-oxadiazol-2-yl)-2-phenyl-2,3-dihydro-1,3,4-thiadiazol-2-yl)propan-1-amine: To a solution of N'-acetyl-2-(3-di-tert-butoxycarbonylaminopropyl)-5-(2,5-difluorophenyl)-2-phenyl-1,3,4-thiadiazole-3(2H)-carbohydrazide (0.052 g, 0.082 mmol) and DIEA (0.11 g, 0.82 mmol) in dichloroethane (2 mL) was added $POCl_3$ (0.063 g, 0.41 mmol). After stirring at room temperature for 30 minutes, the mixture was partitioned between dichloromethane (10 mL) and saturated $NaHCO_3$ (5 mL). The aqueous layer was extracted with dichloromethane and the combined organics were washed with brine (10 mL), dried over $Na_2SO_4$, and concentrated under reduced pressure. The residue was chromatographed (20:1 to 10:1 hexanes/ethyl acetate) to provide the Boc-protected product (0.033 g, 65%). To this product was added formic acid (1 mL). After stirring at room temperature for 45 minutes, the mixture was concentrated under reduced pressure to provide the final product as the formate salt. MS ESI (+) m/z 416 (M+1) detected; $^1$H NMR (400 MHz, $CDCl_3$) δ 8.88 (br, 2H), 7.64 (m, 1H), 7.47 (d, 2H, J=8 Hz), 7.31 (m, 3H), 7.11 (m, 2H), 3.27 (m, 1H), 3.02 (m, 2H), 2.51 (m, 1H), 2.39 (s, 3H), 2.15 (m, 1H), 1.74 (m, 1H).

The following were prepared similarly using the appropriate hydrazides:

Example 5A

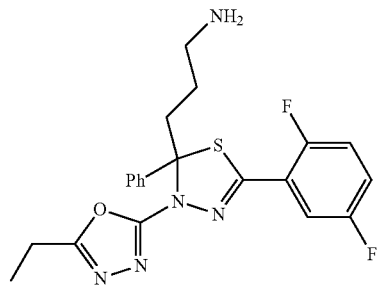 [SMILES: CCc1nnc(N2N=C(c3cc(F)ccc3F)SC2(CCCN)c2ccccc2)o1]

3-(5-(2,5-difluorophenyl)-3-(5-ethyl-1,3,4-oxadiazol-2-yl)-2-phenyl-2,3-dihydro-1,3,4-thiadiazol-2-yl)propan-1-amine MS ESI (+) m/z 430 (M+1) detected; $^1$H NMR (400 MHz, $CDCl_3$) δ 8.30 (br, 1H), 7.65 (m, 1H), 7.49 (d, 2H, J=8 Hz), 7.45 (br, 1H), 7.30 (m, 2H), 7.10 (m, 2H), 3.29 (m, 1H), 3.01 (m, 2H), 2.73 (q, 2H, J=7 Hz), 2.52 (m, 1H), 2.15 (m, 1H), 1.76 (m, 1H), 1.27 (t, 3H, J=7 Hz).

Example 5B

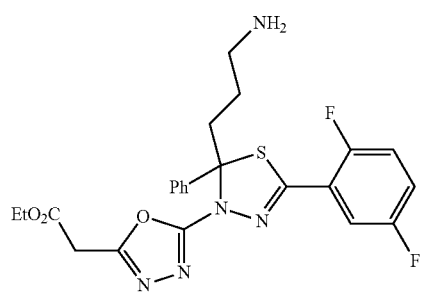 [SMILES: CCOC(=O)Cc1nnc(N2N=C(c3cc(F)ccc3F)SC2(CCCN)c2ccccc2)o1]

Ethyl 2-(5-(2-(3-aminopropyl)-5-(2,5-difluorophenyl)-2-phenyl-1,3,4-thiadiazol-3(2H)-yl)-1,3,4-oxadiazol-2-yl)acetate MS ESI (+) m/z 488 (M+1) detected; $^1$H NMR (400 MHz, $CDCl_3$) δ 8.38 (s, 1H), 7.66 (m, 1H), 7.50 (d, 2H), 7.31 (m, 3H), 7.09 (m, 2H), 6.87 (br, 2H), 4.18 (q, 2H), 3.82 (d, 2H), 3.26 (m, 1H), 2.99 (m, 2H), 2.58 (m, 1H), 2.15 (m, 1H), 1.73 (m, 1H), 1.25 (t, 3H).

Example 6

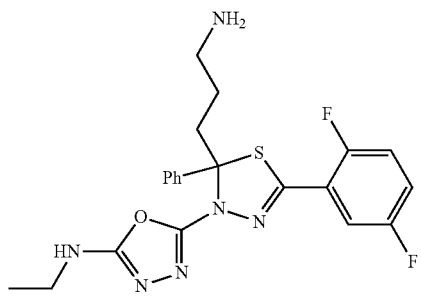 [SMILES: CCNc1nnc(N2N=C(c3cc(F)ccc3F)SC2(CCCN)c2ccccc2)o1]

5-(2-(3-aminopropyl)-5-(2,5-difluorophenyl)-2-phenyl-1,3,4-thiadiazol-3(2H)-yl)-N-ethyl-1,3,4-oxadiazol-2-amine Step A: 1-(2-(3-di-tert-butoxycarbonylaminopropyl)-5-(2,5-difluorophenyl)-2-phenyl-2,3-dihydro-1,3,4-thiadiazole-3-carbonyl)-4-ethylthiosemicarbazide: To a stirred solution of tert-butyl 3-(5-(2,5-difluorophenyl)-3-(1H-3-methylimidazolium-1-carbonyl)-2-phenyl-2,3-dihydro-1,3,4-thiadiazol-2-yl)propylcarbamate iodide (0.396 g, 0.591 mmol) in dichloromethane (4 mL) under $N_2$ was added triethylamine (0.206 mL, 1.48 mmol) followed by 4-ethylthiosemicarbazide (0.141 g, 1.18 mmol). After stirring for 30 minutes, the mixture was diluted with dichloromethane and saturated $NaHCO_3$. The aqueous layer was extracted with dichloromethane and the combined organics were washed with brine, dried over $Na_2SO_4$ and concentrated under reduced pressure. The residue was chromatographed (2:1 hexanes/ethyl acetate) to provide the product (0.167 g, 49%) as a white foam.

Step B: 5-(2-(3-aminopropyl)-5-(2,5-difluorophenyl)-2-phenyl-1,3,4-thiadiazol-3(2H)-yl)-N-ethyl-1,3,4-oxadiazol-2-amine: To a solution of 1-(2-(3-di-tert-butoxycarbonylaminopropyl)-5-(2,5-difluorophenyl)-2-phenyl-2,3-dihydro-1,3,4-thiadiazole-3-carbonyl)-4-ethylthiosemicarbazide (0.033 g, 0.057 mmol) in THF (1 mL) under $N_2$, was added triethylamine (0.0199 mL, 0.143 mmol) followed by EDCI (0.022 g, 0.114 mmol). After heating the mixture to 50° C. for 16 hours, the mixture was cooled to room temperature and diluted with ethyl acetate. The organic layer was washed with saturated $NH_4Cl$ (2×), saturated $NaHCO_3$, and brine. The solution was dried over $Na_2SO_4$ and concentrated under reduced pressure. The residue was chromatographed (1:1 hexanes/ethyl acetate) to provide the Boc-protected product (0.021 g, 68%) as yellow solid. To this product was added formic acid (0.5 mL). After stirring at room temperature for 90 minutes, the mixture was concentrated under reduced pressure, sonicated with pentane, and dried in vacuo to provide the final product (0.017 g, 90%) as the formate salt. MS APCI (+) m/z 445 (M+1) detected; $^1$H NMR (400 MHz, $CDCl_3$) δ 7.86 (br, 2H), 7.58 (m, 1H), 7.48 (d, 2H), 7.28 (m, 3H), 7.06 (m, 2H), 6.00 (br, 1H), 3.18 (m, 3H), 3.01 (m, 1H), 2.91 (m, 1H), 2.43 (m, 1H), 2.12 (m, 1H), 1.81 (m, 1H), 1.11 (t, 3H).

Example 7

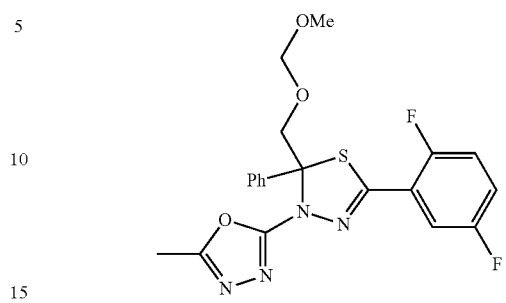

2-(5-(2,5-difluorophenyl)-2-((methoxymethoxy)methyl)-2-phenyl-1,3,4-thiadiazol-3(2H)-yl)-5-methyl-1,3,4-oxadiazole Step A: 2-(methoxymethoxy)-1-phenylethanone: To a cooled (0° C.) solution of 2-hydroxy-1-phenylethanone (1.0 g, 7.3 mmol) in anhydrous DMF (50 mL) was added lithium hydride (74 mg, 95%, 8.8 mmol). After stirring the brown mixture for 30 minutes, MOM-Cl (0.73 mL, 9.5 mmol) was added slowly via syringe. The mixture warmed slowly to room temperature and stirred for 16 hours. The mixture was treated with $NH_4Cl$ (100 mL) and then extracted with ethyl acetate (3×50 mL). The combined organics were washed with water (6×50 mL) and brine (50 mL) then dried over $Na_2SO_4$ and concentrated under reduced pressure. The brown residue was chromatographed (9:1 to 4:1 hexanes/ethyl acetate) to provide the product (0.60 g, 45%) as a colorless oil.

Step B: 5-(2,5-difluorophenyl)-2-((methoxymethoxy)methyl)-2-phenyl-2,3-dihydro-1,3,4-thiadiazole: To a solution of 2-(methoxymethoxy)-1-phenylethanone (600 mg, 3.33 mmol) in ethanol/dichloromethane (12 mL, 3:1) was added 2,5-difluorobenzothiohydrazide (627 mg, 3.33 mmol). After stirring at room temperature for 16 hours, the mixture was concentrated under reduced pressure and chromatographed (9:1 hexanes/ethyl acetate) to afford the product (734 mg, 63%) as a yellow oil.

Step C: (5-(2,5-difluorophenyl)-2-((methoxymethoxy)methyl)-2-phenyl-1,3,4-thiadiazol-3(2H)-yl)(1H-3-methylimidazolium-1-yl)methanone iodide: To a solution of 5-(2,5-difluorophenyl)-2-((methoxymethoxy)methyl)-2-phenyl-2,3-dihydro-1,3,4-thiadiazole (0.234 g, 0.668 mmol) in THF (3 mL) was added di(1H-imidazol-1-yl)methanone (0.162 g, 1.00 mmol). After heating to 70° C. for 2 hours, the mixture was cooled to room temperature, concentrated under reduced pressure and dissolved in dichloromethane (5 mL). The solution was washed with water (2×3 mL), dried over $Na_2SO_4$, concentrated under reduced pressure and dissolved in acetonitrile (2 mL). Iodomethane (0.474 g, 3.34 mmol) was added and the mixture was stirred at room temperature for 24 hours. The mixture was concentrated under reduced pressure to provide the crude product.

Step D: N'-acetyl-5-(2,5-difluorophenyl)-2-((methoxymethoxy)methyl)-2-phenyl-1,3,4-thiadiazol-3(2H)-carbohydrazide: To a solution of (5-(2,5-difluorophenyl)-2-((methoxymethoxy)methyl)-2-phenyl-1,3,4-thiadiazol-3(2H)-yl)(1H-3-methylimidazolium-1-yl)methanone iodide (0.392 g, 0.668 mmol) in dichloromethane (4 mL) was added acetohydrazide (0.099 g, 1.34 mmol). After stirring for 1 hour, the mixture was concentrated under reduced pressure and chromatographed (10:1 hexanes/ethyl acetate) to provide the product (0.221 g, 73%).

Step E: 2-(5-(2,5-difluorophenyl)-2-((methoxymethoxy)methyl)-2-phenyl-1,3,4-thiadiazol-3(2H)-yl)-5-methyl-1,3,4-oxadiazole: To a mixture of N'-acetyl-5-(2,5-difluorophenyl)-2-((methoxymethoxy)methyl)-2-phenyl-1,3,4-thiadiazole-3(2H)-carbohydrazide (0.221 g, 0.491 mmol) and DIEA (0.634 g, 4.91 mmol) in dichloroethane (10 mL) was added POCl₃ (0.376 g, 2.45 mmol). After stirring for 30 minutes, the mixture was partitioned between dichloromethane (10 mL) and saturated NaHCO₃ (5 mL). The organic layer was extracted with dichloromethane (10 mL). The combined organic layers were washed with brine (10 mL), dried over Na₂SO₄, and chromatographed (20:1 to 10:1 hexanes/ethyl acetate) to provide the final product (0.080 g, 38%). MS ESI (+) m/z 433 (M+1) detected; ¹H NMR (400 MHz, CDCl₃) δ 7.68 (m, 1H), 7.54 (d, 2H, J=7 Hz), 7.35 (m, 3H), 7.10 (m, 2H), 4.90 (d, 1H, J=11 Hz), 4.74 (m, 2H), 4.52 (d, 1H, J=11 Hz), 3.37 (s, 3H), 2.44 (s, 3H).

Example 8

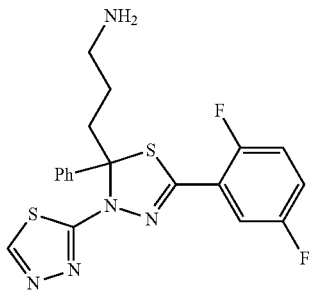 [SMILES: NCCCC1(c2ccccc2)SC(c2cc(F)ccc2F)=NN1c1nncs1]

3-(5-(2,5-difluorophenyl)-2-phenyl-3-(1,3,4-thiadiazol-2-yl)-2,3-dihydro-1,3,4-thiadiazol-2-yl)propan-1-amine Step A: 2-(3-tert-butoxycarbonylaminopropyl)-5-(2,5-difluorophenyl)-2-phenyl-1,3,4-thiadiazole-3(2H)-carbothiohydrazide: To a solution of tert-butyl 3-(5-(2,5-difluorophenyl)-2-phenyl-2,3-dihydro-1,3,4-thiadiazol-2-yl)propylcarbamate (0.123 g, 0.284 mmol) in THF (2 mL) was added di(1H-imidazol-1-yl)methanethione (0.061 g, 0.340 mmol). After heating to 70° C. for 2 hours, the reaction mixture was cooled to room temperature and treated with hydrazine (0.027 g, 0.851 mmol). After stirring for 1 hour, the mixture was concentrated under reduced pressure and chromatographed (10:1 hexanes/ethyl acetate) to provide the product (0.036 g, 25%).

Step B: 3-(5-(2,5-difluorophenyl)-2-phenyl-3-(1,3,4-thiadiazol-2-yl)-2,3-dihydro-1,3,4-thiadiazol-2-yl)propan-1-amine: To a solution of 2-(3-tert-butoxycarbonylaminopropyl)-5-(2,5-difluorophenyl)-2-phenyl-1,3,4-thiadiazole-3 (2H)-carbothiohydrazide (0.018 g, 0.035 mmol) in trimethoxymethane (1 mL) was added 4-methylbenzenesulfonic acid (0.6 mg, 0.0035 mmol). After heating to 60° C. for 1 hour, the mixture was cooled to room temperature and chromatographed (10:1 hexanes/ethyl acetate) to provide the Boc-protected product (5 mg, 27%). To this product was added formic acid (1 mL). After stirring at room temperature for 30 minutes, the reaction mixture was concentrated under reduced pressure to provide the final product as the formate salt. MS ESI (+) m/z 418 (M+1) detected; ¹H NMR (400 MHz, CDCl₃) δ 8.49 (s, 1H), 8.30 (s, 1H), 7.56 (m, 1H), 7.45 (d, 2H), 7.41 (br, 1H), 7.31 (m, 2H), 7.24 (m, 1H), 7.10 (m, 2H), 3.52 (m, 1H), 2.94 (m, 2H), 2.52 (m, 1H), 2.13 (m, 1H), 1.67 (m, 1H).

Example 9

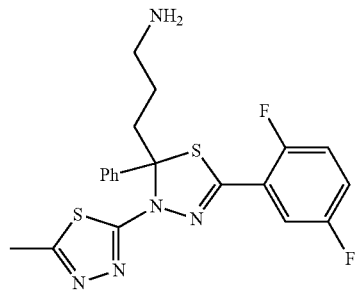 [SMILES: Cc1nnc(N2N=C(c3cc(F)ccc3F)SC2(CCCN)c2ccccc2)s1]

3-(5-(2,5-difluorophenyl)-3-(5-methyl-1,3,4-thiadiazol-2-yl)-2-phenyl-2,3-dihydro-1,3,4-thiadiazol-2-yl)propan-1-amine Step A: N'-acetyl-2-(3-tert-butoxycarbonylaminopropyl)-5-(2,5-difluorophenyl)-2-phenyl-1,3,4-thiadiazole-3(2H)-carbothiohydrazide: To a solution of 2-(3-tert-butoxycarbonylaminopropyl)-5-(2,5-difluorophenyl)-2-phenyl-1,3,4-thiadiazole-3(2H)-carbothiohydrazide (0.016 g, 0.032 mmol) in dichloromethane (1 mL) was added acetic anhydride (0.032 g, 0.32 mmol). After stirring for 1 hour at room temperature, the reaction mixture was concentrated under reduced pressure and chromatographed (10:1 hexanes/ethyl acetate) to provide the product.

Step B: 3-(5-(2,5-difluorophenyl)-3-(5-methyl-1,3,4-thiadiazol-2-yl)-2-phenyl-2,3-dihydro-1,3,4-thiadiazol-2-yl)propan-1-amine: To a solution of N'-acetyl-2-(3-tert-butoxycarbonylaminopropyl)-5-(2,5-difluorophenyl)-2-phenyl-1,3,4-thiadiazole-3(2H)-carbothiohydrazide (0.008 g, 0.015 mmol) in dichloroethane (1 mL) was added POCl₃ (0.011 g, 0.073 mmol) and DIEA (0.019 g, 0.15 mmol). After stirring at room temperature for 30 minutes, the mixture was partitioned between saturated NaHCO₃ (2 mL) and dichloromethane (5 mL). The organic layer was dried over Na₂SO₄, concentrated under reduced pressure and chromatographed (10:1 hexanes/ethyl acetate) to provide the Boc-protected product (2 mg, 26%). To this product was added formic acid (1 mL). After stirring for 30 minutes, the mixture was concentrated under reduced pressure to provide the final product as the formate salt. MS ESI (+) m/z 432 (M+1) detected; ¹H NMR (400 MHz, CDCl₃) δ 8.20 (br, 2H), 7.53 (m, 1H), 7.44 (d, 2H), 7.32

(m, 3H), 7.11 (m, 2H), 3.53 (m, 1H), 3.03 (m, 1H), 2.97 (m, 1H), 2.52 (s, 3H), 2.45 (m, 1H), 2.19 (m, 1H), 1.75 (m, 1H).

Example 10

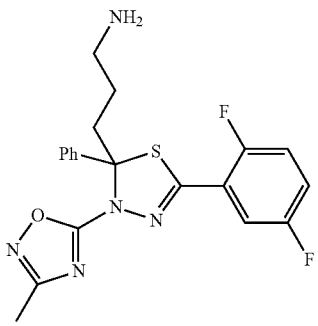 [SMILES: Cc1noc(N2N=C(c3cc(F)ccc3F)SC2(CCCN)c2ccccc2)n1]

3-(5-(2,5-difluorophenyl)-3-(3-methyl-1,2,4-oxadiazol-5-yl)-2-phenyl-2,3-dihydro-1,3,4-thiadiazol-2-yl)propan-1-amine Step A: di-tert-butyl 3-(5-(2,5-difluorophenyl)-3-((1-(acetoxyimino)ethyl) carbamoyl)-2-phenyl-2,3-dihydro-1,3,4-thiadiazol-2-yl)propylaminodicarboxylate: To a solution of (5-(2,5-difluorophenyl)-2-(3-di-tert-butoxycarbonylaminopropyl)-2-phenyl-1,3,4-thiadiazol-3(2H)-yl)(1H-3-methylimidazolium-1-yl)methanone iodide (0.101 g, 0.131 mmol) dissolved in dichloromethane (2 mL) was added N'-hydroxyacetamidine (0.009 g, 0.131 mmol) followed by triethylamine (0.016 g, 0.157 mmol). After stirring at room temperature for 1 hour, the mixture was chromatographed (10:1 hexanes/ethyl acetate) to provide the oxime product. This product was dissolved in dichloromethane (1 mL) and treated with acetic anhydride (0.080 g, 0.787 mmol). After stirring at room temperature for 24 hours, the reaction mixture was concentrated under reduced pressure to provide the crude product.

Step B: 3-(5-(2,5-difluorophenyl)-3-(3-methyl-1,2,4-oxadiazol-5-yl)-2-phenyl-2,3-dihydro-1,3,4-thiadiazol-2-yl)propan-1-amine: di-tert-butyl 3-(5-(2,5-difluorophenyl)-3-((1-(acetoxyimino)ethyl)carbamoyl)-2-phenyl-2,3-dihydro-1,3,4-thiadiazol-2-yl)propylaminodicarboxylate was heated in pyridine (1 mL) in a sealed tube to 80° C. for 12 hours. The reaction mixture was cooled to room temperature and diluted with ethyl acetate (10 mL) and HCl (5 mL of 1M solution). The organic layer was dried over $Na_2SO_4$ and chromatographed (20:1 to 10:1 hexanes/ethyl acetate) to provide the Boc-protected product (2 mg, 27%). To this product was added formic acid (1 mL). After stirring at room temperature for 30 minutes, the reaction mixture was concentrated under reduced pressure to provide the final product as the formate salt. MS ESI (+) m/z 416 (M+1) detected; $^1$H NMR (400 MHz, $CDCl_3$) δ 8.19 (br, 1H), 7.71 (m, 1H), 7.43 (d, 2H), 7.33 (m, 3H), 7.10 (m, 2H), 3.19 (m, 1H), 3.03 (m, 2H), 2.64 (m, 1H), 2.21 (m, 1H), 2.17 (s, 3H), 1.73 (m, 1H).

Example 11

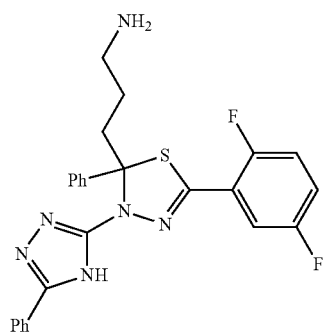 [SMILES: NCCCC1(c2ccccc2)SC(c2cc(F)ccc2F)=NN1c1nnc(-c2ccccc2)[nH]1]

3-(5-(2,5-difluorophenyl)-2-phenyl-3-(5-phenyl-4H-1,2,4-triazol-3-yl)-2,3-dihydro-1,3,4-thiadiazol-2-yl)propan-1-amine Step A: tert-butyl 3-(3-(benzoylcarbamothioyl)-5-(2,5-difluorophenyl)-2-phenyl-2,3-dihydro-1,3,4-thiadiazol-2-yl)propylcarbamate: To a solution of tert-butyl 3-(5-(2,5-difluorophenyl)-2-phenyl-2,3-dihydro-1,3,4-thiadiazol-2-yl)propylcarbamate (1.60 g, 3.69 mmol) in THF (37 mL) was added benzoyl isothiocyanate (0.595 mL, 4.43 mmol). After heating to reflux for 5 hours and to 60° C. for 16 hours, the reaction mixture was concentrated under reduced pressure. The residue was chromatographed (30% ethyl acetate in hexanes) to provide the product (1.84 g, 84%) as an orange-yellow foam.

Step B: methyl N-benzoyl-2-(3-(tert-butoxycarbonyl)propyl)-5-(2,5-difluorophenyl)-2-phenyl-1,3,4-thiadiazole-3(2H)-carbthioimidate: To a cooled (0° C.) solution of tert-butyl 3-(3-(benzoylcarbamothioyl)-5-(2,5-difluorophenyl)-2-phenyl-2,3-dihydro-1,3,4-thiadiazol-2-yl)propylcarbamate (0.022 g, 0.037 mmol) in THF (0.4 mL) was added sodium carbonate (0.022 g, 0.208 mmol) followed by iodomethane (0.006 mL, 0.096 mmol). After stirring at room temperature for 1 hour, more iodomethane (25 μL, 11 equiv.) was added to the mixture. After stirring at room temperature for 15 hours, the mixture was diluted with saturated $NaHCO_3$ and extracted with ethyl acetate (3×25 mL). The combined organics were washed with brine, dried over $Na_2SO_4$, filtered and concentrated under reduced pressure to provide the crude product as a brown film.

Step C: 3-(5-(2,5-difluorophenyl)-2-phenyl-3-(5-phenyl-4H-1,2,4-triazol-3-yl)-2,3-dihydro-1,3,4-thiadiazol-2-yl)propan-1-amine: To a cooled (0° C.) solution of methyl N-benzoyl-2-(3-(tert-butoxycarbonyl)propyl)-5-(2,5-difluorophenyl)-2-phenyl-1,3,4-thiadiazole-3(2H)-carbthioimidate (0.011 g, 0.018 mmol) in ethanol (0.5 mL) was added hydrazine (0.007 mL, 0.223 mmol). The ice bath was removed and the mixture stirred at room temperature for 1 hour. After concentrating the mixture under reduced pressure, the residue was chromatographed (20% ethyl acetate in hexanes) to provide the Boc-protected product (0.010 g, 98%). To this product was added HCl (0.5 mL of 4.0 M solution, 2.0 mmol). After stirring at 0° C. for 2 hours and room temperature for 1 hour, the reaction mixture was concentrated under reduced pressure, washed with ether, filtered and dried to provide the final product as the di-HCl salt. MS ESI (+) m/z 477 (M+1) detected; $^1$H NMR (400 MHz, CDCl$_3$) δ 7.95 (m, 3H), 7.52 (m, 5H), 7.34 (m, 3H), 7.14 (m, 2H), 3.45 (m, 1H), 3.14 (m, 1H), 3.05 (m, 1H), 2.64 (m, 1H), 2.30 (m, 1H), 1.92 (m, 1H).

The compounds of Examples 12-15 were prepared according to the above-described methods, using the appropriate starting materials.

Example 12

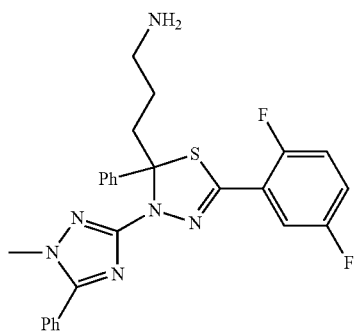 [SMILES: Cn1nc(N2N=C(c3cc(F)ccc3F)SC2(CCCN)c2ccccc2)nc1-c1ccccc1]

3-(5-(2,5-difluorophenyl)-3-(1-methyl-5-phenyl-H-1,2,4-triazol-3-yl)-2-phenyl-2,3-dihydro-1,3,4-thiadiazol-2-yl)propan-1-amine MS ESI (+) m/z 491 (M+1) detected; $^1$H NMR (400 MHz, 19:1 CDCl$_3$:CD$_3$OD) δ 7.93 (m, 1H), 7.78-7.71 (m, 2H), 7.68-7.56 (m, 5H), 7.42 (t, 2H, J=7 Hz), 7.35 (m, 1H), 7.15-7.11 (m, 2H), 3.43 (m, 1H), 3.37 (s, 3H), 3.21-3.04 (m, 2H), 2.57 (m, 1H), 2.28 (m, 1H), 2.02 (m, 1H).

Example 13

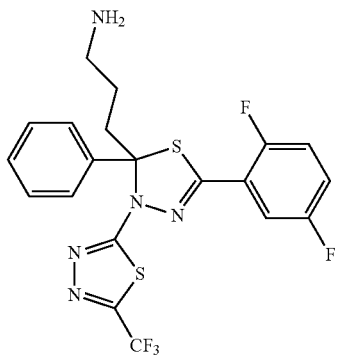 [SMILES: NCCCC1(c2ccccc2)SC(c2cc(F)ccc2F)=NN1c1nnc(C(F)(F)F)s1]

3-(5-(2,5-difluorophenyl)-2-phenyl-3-(5-(trifluoromethyl)-1,3,4-thiadiazol-2-yl)-2,3-dihydro-1,3,4-thiadiazol-2-yl)propan-1-amine MS ESI (+) m/z 485 (M+1) detected; $^1$H NMR (400 MHz, CD$_3$OD) δ 7.67 (m, 1H), 7.54 (m, 2H), 7.42 (m, 2H), 7.33 (m, 3H), 3.49 (m, 1H), 3.09 (m, 2H), 2.79 (m, 4H), 2.27 (m, 1H), 1.74 (m, 1H).

Example 14

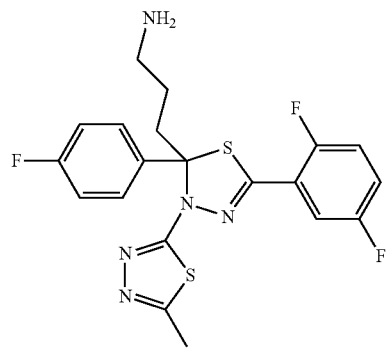 [SMILES: Cc1nnc(N2N=C(c3cc(F)ccc3F)SC2(CCCN)c2ccc(F)cc2)s1]

3-(5-(2,5-difluorophenyl)-2-(4-fluorophenyl)-3-(5-methyl-1,3,4-thiadiazol-2-yl)-2,3-dihydro-1,3,4-thiadiazol-2-yl)propan-1-amine MS ESI (+) m/z 522 (M−17 [NH$_3$]) detected; $^1$H NMR (400 MHz, CDCl$_3$) δ 8.65 (s, 3H), 7.68 (m, 2H), 7.54 (m, 1H), 7.16 (m, 2H), 7.08 (t, 2H, J=8.2 Hz), 3.70 (m, 1H), 3.25 (s, 1H), 3.04 (s, 1H), 2.93 (2, 3H), 2.43 (t, 1H, J=11.7 Hz), 2.22 (s, 1H), 2.02 (s, 1H).

Example 15

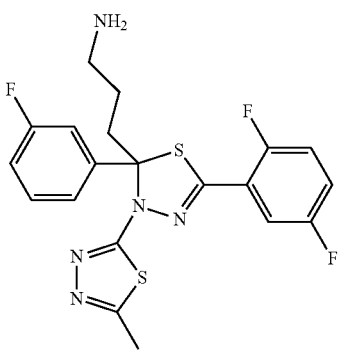 [SMILES: Cc1nnc(N2N=C(c3cc(F)ccc3F)SC2(CCCN)c2cccc(F)c2)s1]

3-(5-(2,5-difluorophenyl)-2-(3-fluorophenyl)-3-(5-methyl-1,3,4-thiadiazol-2-yl)-2,3-dihydro-1,3,4-thiadiazol-2-yl)propan-1-amine MS ESI (+) m/z 522 (M−17 [NH$_3$]) detected; $^1$H NMR (400 MHz, CD$_3$OD) δ 7.61 (m, 1H), 7.41 (m, 1H), 7.29 (m, 4H), 7.08 (m, 1H), 3.43 (m, 1H), 3.08 (m, 2H), 2.69 (m, 1H), 2.59 (s, 3H), 2.32 (m, 1H), 1.76 (m, 1H).

Example 16

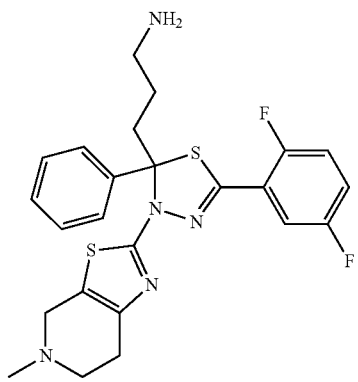 [SMILES: CN1CCc2nc(N3N=C(c4cc(F)ccc4F)SC3(CCCN)c3ccccc3)sc2C1]

3-(5-(2,5-difluorophenyl-3-(5-methyl-4,5,6,7-tetrahydrothiazolo[5,4-c]pyridin-2-yl)-2-phenyl-2,3-dihydro-1,3,4-thiadiazol-2-yl)propan-1-amine Step A: Preparation of N-(2-(3-azidopropyl)-5-(2,5-difluorophenyl)-2-phenyl-2,3-dihydro-1,3,4-thiadiazole-3-carbonothioyl)benzamide: To a solution of 2-(3-azidopropyl)-5-(2,5-difluorophenyl)-2-phenyl-2,3-dihydro-1,3,4-thiadiazole (1.00 g, 2.79 mmol) in 20 mL of anhydrous THF was added benzoyl isothiocyanate (0.45 mL, 3.34 mmol). The reaction mixture was stirred overnight at reflux, then cooled and concentrated in vacuo. The residue was purified by flash column chromatography (5-35% ethyl acetate/hexanes) to afford the desired product as a yellow gum (1.45 g, 54%).

Step B: Preparation of 2-(3-azidopropyl)-5-(2,5-difluorophenyl)-2-phenyl-1,3,4-thiadiazole-3(2H)-carbothioamide: To a solution of N-(2-(3-azidopropyl)-5-(2,5-difluorophenyl)-2-phenyl-2,3-dihydro-1,3,4-thiadiazole-3-carbonothioyl)benzamide (0.737 g, 1.41 mmol) in 20 mL of anhydrous THF was added hydrazine (0.088 mL, 2.82 mmol). The reaction mixture was stirred at room temperature for 3 hours, and then concentrated in vacuo. The residue was purified by flash column chromatography (10-20% ethyl acetate/hexanes) to afford the desired product as a pale yellow foam, 0.504 g, 85%.

Step C: Preparation of tert-butyl 2-(2-(3-azidopropyl)-5-(2,5-difluorophenyl)-2-phenyl-1,3,4-thiadiazol-3(2H)-yl)-6,7-dihydrothiazolo[5,4-c]pyridine-5 (4H)-carboxylate: To a solution of 2-(3-azidopropyl)-5-(2,5-difluorophenyl)-2-phenyl-1,3,4-thiadiazole-3(2H)-carbothioamide (0.300 g, 0.717 mmol) in 10 mL of ethanol was added tert-butyl 3-bromo-4-oxopiperidine-1-carboxylate (0.239 g, 0.860 mmol) followed by DIEA (0.25 mL, 1.43 mmol). The mixture was allowed to stir overnight at reflux then treated with tert-butyl 3-bromo-4-oxopiperidine-1-carboxylate (100 mg) and stirred at reflux for a further 3 hrs. The cooled mixture was partitioned between saturated NaHCO$_3$ solution (30 mL) and EtOAc (30 mL) and the aqueous layer was extracted with EtOAc (2×20 mL). The combined organic phases were washed with brine (20 mL) dried over Na$_2$SO$_4$ and concentrated in vacuo. The residue was purified by flash column chromatography (5-10% ethyl acetate/hexanes) to afford the desired product as a bright yellow foam (0.313 g, 73%).

Step D: Preparation of 2-(2-(3-azidopropyl)-5-(2,5-difluorophenyl)-2-phenyl-1,3,4-thiadiazol-3(2H)-yl)-4,5,6,7-tetrahydrothiazolo[5,4-c]pyridine: To a solution of tert-butyl 2-(2-(3-azidopropyl)-5-(2,5-difluorophenyl)-2-phenyl-1,3,4-thiadiazol-3(2H)-yl)-6,7-dihydrothiazolo[5,4-c]pyridine-5(4H)-carboxylate (0.313 g, 0.524 mmol) in 10.0 mL of DCM at 0° C. was added TFA (1 mL). The mixture was stirred for 1 hour at 0° C. then at room temperature for 1 hour. The reaction was then concentrated to dryness and partitioned between EtOAc (30 mL) and saturated NaHCO$_3$ solution (30 mL). The aqueous layer was extracted with EtOAc (2×20 mL) and the combined organic phases were washed with brine (20 mL), dried over Na$_2$SO$_4$ and concentrated in vacuo to afford the desired product as a yellow gum (0.251 g, 96%).

Step E: Preparation of 2-(2-(3-azidopropyl)-5-(2,5-difluorophenyl)-2-phenyl-1,3,4-thiadiazol-3(2H)-yl)-5-methyl-4,5,6,7-tetrahydrothiazolo[5,4-c]pyridine. To a solution of 2-(2-(3-azidopropyl)-5-(2,5-difluorophenyl)-2-phenyl-1,3,4-thiadiazol-3(2H)-yl)-4,5,6,7-tetrahydrothiazolo[5,4-c]pyridine (0.050 g, 0.100 mmol) in 1 mL DCE was added formaldehyde (0.033 g, 37 wt % in water, 0.401 mmol) followed by sodium triacetoxyborohydride (0.023 g, 0.110 mmol). The resulting suspension was stirred vigorously at room temperature overnight then was treated with saturated Na$_2$CO$_3$ solution (10 mL) and stirred for 10 minutes. The mixture was extracted with EtOAc (3×10 mL) and the combined organic phases were washed with brine (10 mL), dried over Na$_2$SO$_4$ and concentrated in vacuo. The residue was purified by flash column chromatography (0-3% MeOH/DCM) to afford the desired product as a yellow foam (0.046 g, 89%).

Step F: Preparation of 3-(5-(2,5-difluorophenyl)-3-(5-methyl-4,5,6,7-tetrahydrothiazolo[5,4-c]pyridin-2-yl)-2-phenyl-2,3-dihydro-1,3,4-thiadiazol-2-yl)propan-1-amine. To a solution of 2-(2-(3-azidopropyl)-5-(2,5-difluorophenyl)-2-phenyl-1,3,4-thiadiazol-3(2H)-yl)-5-methyl-4,5,6,7-tetrahydrothiazolo[5,4-c]pyridine (0.046 g, 0.090 mmol) in 2 mL of methanol was added 1N HCl/MeOH (0.27 mL, 0.27 mmol) followed by 10% Pd/C (10 mg). The mixture was hydrogenated under a balloon atmosphere for 1 hour then filtered through GF paper and the filtrate concentrated in vacuo. The residue was triturated with diethyl ether, filtered, washed with ether and dried in vacuo to afford the desired product as a bright yellow solid (0.027 g, 50%). MS ESI (+) m/z 486 (M+1) detected; $^1$H NMR (400 MHz, CDCl$_3$) δ 7.59 (m, 1H), 7.45 (d, 2H, J=7.6 Hz), 7.32 (m, 2H), 7.26 (m, 1H), 7.06 (m, 2H), 3.50 (m, 2H), 3.43 (m, 1H), 2.77 (t, 2H, J=6.9 Hz), 2.68 (m, 2H), 2.56 (m, 2H), 2.46 (s, 3H), 2.41 (m, 1H), 1.99 (m, 1H), 1.55 (m, 1H) ppm.

Example 17

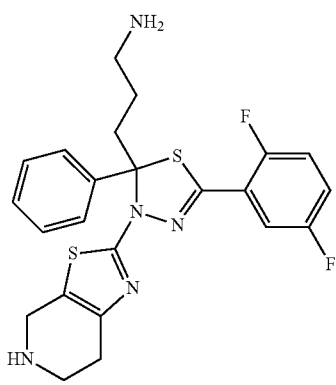 [SMILES: NCCCC1(c2ccccc2)SC(c2cc(F)ccc2F)=NN1c1nc2c(s1)CNCC2]

3-(5-(2,5-difluorophenyl)-2-phenyl-3-(4,5,6,7-tetrahydrothiazolo[5,4-c]pyridin-2-yl)-2,3-dihydro-1,3,4-thiadiazol-2-yl)propan-1-amine To a solution of 2-(2-(3-azidopropyl)-5-(2,5-difluorophenyl)-2-phenyl-1,3,4-thiadiazol-3(2H)-yl)-4,5,6,7-tetrahydrothiazolo[5,4-c]pyridine (prepared as in Example 16, Steps A-D) (0.050 g, 0.100 mmol) in 2 mL of methanol was added 1N HCl/MeOH (0.30 mL, 0.30 mmol) followed by 10% Pd/C (10 mg). The mixture was hydrogenated under a balloon atmosphere for 1 hour then filtered through GF paper and the filtrate concentrated in vacuo. The residue was triturated with diethyl ether, filtered, washed with ether and dried in vacuo to afford the desired product as a bright yellow solid, 0.018 g, 31%. MS ESI (+) m/z 472 (M+1) detected; $^1$H NMR (400 MHz, CDCl$_3$) δ 7.59 (m, 1H), 7.46 (m, 2H), 7.33 (m, 3H), 7.05 (m, 2H), 3.88 (m, 2H), 3.46 (m, 1H), 3.06 (m, 2H), 2.79 (m, 2H), 2.44 (m, 3H), 2.01 (m, 1H), 1.57 (m, 1H) ppm.

Example 18

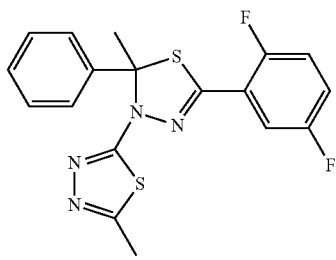 [SMILES: Cc1nnc(N2N=C(c3cc(F)ccc3F)SC2(C)c2ccccc2)s1]

2-(5-(2,5-difluorophenyl)-2-methyl-2-phenyl-1,3,4-thiadiazol-3(2H)-yl)-5-methyl-1,3,4-thiadiazole Step A: Preparation of 5-(2,5-difluorophenyl)-2-methyl-2-phenyl-2,3-dihydro-1,3,4-thiadiazole. To a solution of acetophenone (0.600 g, 5.00 mmol) in 20 mL of a 3:1 EtOH/DCM mixture was added 2,5-difluorobenzothiohydrazide (0.941 g, 5.00 mmol). The reaction was allowed to stir overnight at room temperature. The reaction was then heated to 45° C., for 14 hours. The reaction mixture was then concentrated in vacuo, and the residue was loaded directly to Biotage-(45), followed by flash column chromatography (20% ethyl acetate/hexanes), yielding 5-(2,5-the desired product (1.021 g, 70% yield) as a yellow semi-solid.

Step B: Preparation of 5-(2,5-difluorophenyl)-2-methyl-2-phenyl-1,3,4-thiadiazole-3(2H)-carbothiohydrazide. 5-(2,5-difluorophenyl)-2-methyl-2-phenyl-2,3-dihydro-1,3,4-thiadiazole (0.290 g, 1.00 mmol) was weighed into a 25 mL flask, and suspended in 10 mL of anhydrous THF, followed by addition of thiocarbonyldiimidazole (0.196 g, 1.10 mmol). The reaction was then heated to reflux for 3 hours, at which time all starting material was consumed. The reaction was cooled to room temperature, followed by addition of hydrazine (0.156 mL, 5.00 mmol). Following 4 hours at room temperature, all intermediate was consumed by LC-MS. The reaction was then concentrated, then loaded to Biotage-(45) followed by flash column chromatography (10-50% ethyl acetate/hexanes), affording the desired product (80% purity; 0.268 g, 74%).

Step C: Preparation of 2-(5-(2,5-difluorophenyl)-2-methyl-2-phenyl-1,3,4-thiadiazol-3(2H)-yl)-5-methyl-1,3,4-thiadiazole. 5-(2,5-difluorophenyl)-2-methyl-2-phenyl-1,3,4-thiadiazole-3(2H)-carbothiohydrazide (0.268 g, 0.735 mmol) was weighed into a 25 mL 1 neck flask, and suspended in 9.0 mL of trimethylorthoacetate (0.088 g, 0.74 mmol). P-toluenesulfonic acid hydrate (0.0028 g, 0.015 mmol) was then added, and the reaction heated to 80° C. for 1 hour. The reaction was then concentrated in vacuo, and then purified by flash column chromatography (20-50% ethyl acetate/hexanes) yielding 0.201 g, 70% of the desired product as a white solid. MS ESI (+) m/z 389 (M+1) detected; $^1$H NMR (400 MHz, CDCl$_3$) δ 7.56 (m, 2H), 7.34 (m, 2H), 7.27 (m, 2H), 7.08 (m, 2H), 2.59 (s, 3H), 2.56 (s, 3H).

Example 19

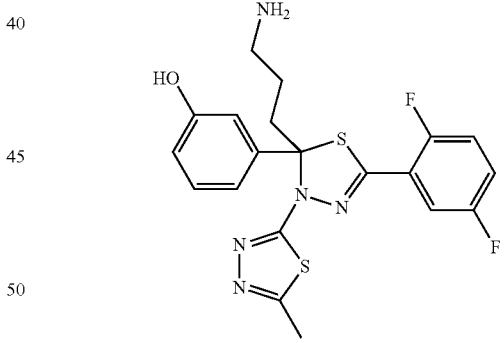

3-(2-(3-aminopropyl)-5-(2,5-difluorophenyl)-3-(5-methyl-1,3,4-thiadiazol-2-yl)-2,3-dihydro-1,3,4-thiadiazol-2-yl)phenol Step A: Preparation of tert-butyl 3-(2-(3-(tert-butyldimethylsilyloxy)phenyl)-5-(2,5-difluorophenyl)-2,3-dihydro-1,3,4-thiadiazol-2-yl)propylcarbamate. To a solution of tert-butyl 4-(3-(tert-butyldimethylsilyloxy)phenyl)-4-oxobutylcarbamate (1.400 g, 3.55 mmol) in 20 mL of a 3:1 EtOH/DCM mixture was added 2,5-difluorobenzothiohydrazide (0.704 g, 3.74 mmol). The reaction was stirred overnight at room temperature, then heated to 45° C. for 10 hours. The reaction mixture was then concentrated in vacuo, loaded directly to Biotage (45), followed by flash column chromatography (20-50% ethyl acetate/hexanes), yielding the desired product as a yellow semi-solid (1.742 g, 82%).

Step B: Preparation of tert-butyl 3-(2-(3-(tert-butyldimethylsilyloxy)phenyl)-5-(2,5-difluorophenyl)-3-(hydrazinecarbonothioyl)-2,3-dihydro-1,3,4-thiadiazol-2-yl)propylcarbamate. Tert-butyl 3-(2-(3-(tert-butyldimethylsilyloxy)phenyl)-5-(2,5-difluorophenyl)-2,3-dihydro-1,3,4-thiadiazol-2-yl)propylcarbamate (0.845 g, 1.50 mmol) was weighed into a 25 mL flask and suspended in 10 mL of anhydrous THF, followed by addition of thiocarbonyldiimidazole (0.294 g, 1.65 mmol). The reaction mixture was then heated to reflux for 3 hours. The reaction was cooled to room temperature, and then hydrazine (0.235 mL 7.50 mmol) was added and the reaction mixture was stirred for 4 hours at room temperature. The reaction mixture was concentrated, and the residue was loaded onto Biotage (flash column chromatography 10-50% ethyl acetate/hexanes) to provide 143 mg (80% purity) of the desired product.

Step C: Preparation of tert-butyl 3-(2-(3-(tert-butyldimethylsilyloxy)phenyl)-5-(2,5-difluorophenyl)-3-(5-methyl-1,3,4-thiadiazol-2-yl)-2,3-dihydro-1,3,4-thiadiazol-2-yl)propylcarbamate. Tert-butyl 3-(2-(3-(tert-butyldimethylsilyloxy)phenyl)-5-(2,5-difluorophenyl)-3-(hydrazinecarbonothioyl)-2,3-dihydro-1,3,4-thiadiazol-2-yl)propylcarbamate (100 mg, 0.157 mmol) was weighed into a 25 mL flask and suspended in 5.0 mL of 1,1,1-trimethoxyethane (5 mL, 0.157 mmol). 4-methylbenzenesulfonic acid (0.540 mg, 0.00314 mmol) was then added, and the reaction heated to 80° C. for 1 hour. The reaction mixture was concentrated in vacuo, and the residue was purified by flash column chromatography (20-50% ethyl acetate/hexanes), to afford 75 mg (72% yield) of the desired product as a yellow solid on standing.

Step D: Preparation of tert-butyl 3-(5-(2,5-difluorophenyl)-2-(3-hydroxyphenyl)-3-(5-methyl-1,3,4-thiadiazol-2-yl)-2,3-dihydro-1,3,4-thiadiazol-2-yl)propylcarbamate: t-Butyl 3-(2-(3-(tert-butyldimethylsilyloxy)phenyl)-5-(2,5-difluorophenyl)-3-(5-methyl-1,3,4-thiadiazol-2-yl)-2,3-dihydro-1,3,4-thiadiazol-2-yl)propylcarbamate (75 mg, 0.113 mmol) was weighed into a 25 mL flask and dissolved in 10.0 mL of THF, then cooled to 0° C. TBAF (0.39 mL, 0.39 mmol) was added dropwise and the reaction mixture was allowed to warm to room temperature overnight. The reaction mixture was concentrated to dryness, then re-dissolved in DCM, washed with saturated NaHCO$_3$ solution, dried over Na$_2$SO$_4$, and concentrated in vacuo. The residue was purified by removal of tributylamine via successive washes with 1N HCl. The organic layer was concentrated in vacuo, and the yellow oil subject to purification by flash column chromatography (25-60% ethyl acetate/hexanes) to afford the desired product (51 mg, 82% yield) as a yellow foam.

Step E: Preparation of 3-(2-(3-aminopropyl)-5-(2,5-difluorophenyl)-3-(5-methyl-1,3,4-thiadiazol-2-yl)-2,3-dihydro-1,3,4-thiadiazol-2-yl)phenol: Tert-butyl 3-(5-(2,5-difluorophenyl)-2-(3-hydroxyphenyl)-3-(5-methyl-1,3,4-thiadiazol-2-yl)-2,3-dihydro-1,3,4-thiadiazol-2-yl)propylcarbamate (51 mg, 0.093 mmol) was weighed into a 25 mL flask, and dissolved in 7 mL of Et$_2$O/DCM (1:1). HCl-Et$_2$O (1.8 mL, 1.863 mmol) was added, and the reaction mixture was stirred at room temperature for 2 hours. An additional 20 equivalents of HCl-Et$_2$O was added and the reaction mixture was stirred an additional 2 hours. The crude reaction mixture was concentrated in vacuo to afford a yellow solid. The solid was then purified by flash column chromatography (10-40% MeOH/DCM), affording the desired product (31 mg, 74% yield) as a yellow foam. MS ESI (+) m/z 448 (M+1) detected; $^1$H NMR (400 MHz, DMSO-D$_6$) δ 7.90 (m, 1H), 7.51 (m, 2H), 7.19 (m, 1H), 6.84 (m, 2H), 6.74 (m, 1H), 3.21 (m, 1H), 2.98 (m, 1H), 2.89 (m, 2H), 2.56 (m, 3H), 2.61 (m, 1H), 2.10 (m, 1H), 1.60 (m, 1H).

Example 20

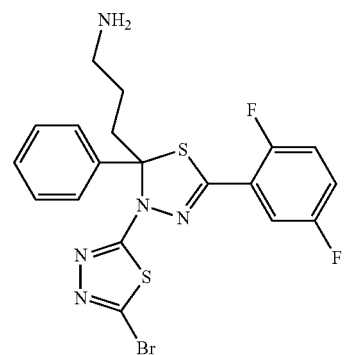 [SMILES: NCCCC1(c2ccccc2)SC(c2cc(F)ccc2F)=NN1c1nnc(Br)s1]

3-(3-(5-bromo-1,3,4-thiadiazol-2-yl)-5-(2,5-difluorophenyl)-2-phenyl-2,3-dihydro-1,3,4-thiadiazol-2-yl)propan-1-amine Step A: Preparation of 2-(3-azidopropyl)-5-(2,5-difluorophenyl)-2-phenyl-1,3,4-thiadiazole-3(2H)-carbothiohydrazide: 2-(3-azidopropyl)-5-(2,5-difluorophenyl)-2-phenyl-2,3-dihydro-1,3,4-thiadiazole (577 mg, 1.61 mmol) was dissolved in 8 mL THF, followed by addition of thio-carbonyldiimidazole (458 mg, 2.57 mmol), and heated to reflux for 1 hour. The reaction mixture was cooled to 23° C., and hydrazine (257 mg, 8.03 mmol) was added. The reaction mixture was stirred for 12 hours. The crude reaction mixture was then concentrated and purified by flash column chromatography, eluting with 4:1 (hexanes/ethyl acetate), to afford the desired product (135 mg, 20%).

Step B: 2-(2-(3-azidopropyl)-5-(2,5-difluorophenyl)-2-phenyl-1,3,4-thiadiazol-3(2H)-yl)-1,3,4-thiadiazole: 2-(3-azidopropyl)-5-(2,5-difluorophenyl)-2-phenyl-1,3,4-thiadiazole-3(2H)-carbothiohydrazide (220 mg, 0.51 mmol) was dissolved in trimethyl-orthoformate (1.62 g, 15.2 mmol) with a few crystals of pTsOH (10 mg, 0.05 mmol), and heated to 80° C. for 20 minutes. The reaction mixture was then concentrated and purified by flash column chromatography, eluting with 4:1 (hexanes/ethyl acetate), to afford the desired product as a light yellow oil (202 mg, 90%).

Step C: Preparation of 2-(2-(3-azidopropyl)-5-(2,5-difluorophenyl)-2-phenyl-1,3,4-thiadiazol-3(2H)-yl)-5-bromo-1,3,4-thiadiazole: 2-(2-(3-azidopropyl)-5-(2,5-difluorophenyl)-2-phenyl-1,3,4-thiadiazol-3(2H)-yl)-1,3,4-thiadiazole (0.020 g, 0.0451 mmol) was dissolved in 0.25 mL ACN, followed by addition of N-Bromosuccinimide (0.00883 g, 0.0496 mmol), and the reaction mixture was heated at 60° C. for 14 hours. The reaction mixture was concentrated, and the residue was partitioned between ethyl acetate and saturated sodium bicarbonate solution. The organic layer was washed with brine, dried over Na$_2$SO$_4$, filtered, and concentrated. The crude material was then purified by flash column chromatography, eluting with 5.3:1 (hexanes/ethyl acetate), to afford the desired product as a thick golden oil (22 mg, 93%).

Step D: Preparation of 3-(3-(5-bromo-1,3,4-thiadiazol-2-yl)-5-(2,5-difluorophenyl)-2-phenyl-2,3-dihydro-1,3,4-thiadiazol-2-yl)propan-1-amine: 2-(2-(3-azidopropyl)-5-(2,5-difluorophenyl)-2-phenyl-1,3,4-thiadiazol-3(2H)-yl)-5-bromo-1,3,4-thiadiazole (0.006 g, 0.011 mol) was dissolved in 0.25 mL THF, followed by addition of water (0.015 g, 15 µL) and triphenylphosphine (0.015 g, 0.057 mmol), and the reaction mixture was stirred at 23° C. overnight. The crude mixture was purified by directly loading onto a preparative TLC plate and eluting first with 12:1 (DCM:MeOH), followed by a second elution with 10:1 (DCM:MeOH) (both with NH$_4$OH present), to afford the desired product (0.003 g, 53%). MS ESI (+) m/z 495/497 (M+1) detected; $^1$H NMR (400 MHz, CDCl$_3$) δ 7.52 (m, 3H), 7.35 (t, 2H, J=7.6 Hz), 7.30 (d, 1H, J=7.2 Hz), 7.12 (m, 2H), 3.46 (m, 1H), 2.65 (m, 6H), 2.05 (m, 1H), 1.61 (m, 1H).

Example 21

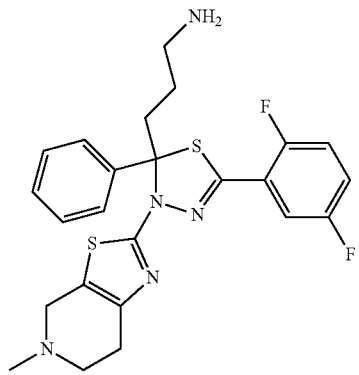 [SMILES: CN1CCc2nc(N3N=C(c4cc(F)ccc4F)SC3(CCCN)c3ccccc3)sc2C1]

3-(5-(2,5-difluorophenyl)-3-(5-methyl-4,5,6,7-tetrahydrothiazolo[5,4-c]pyridin-2-yl)-2-phenyl-2,3-dihydro-1,3,4-thiadiazol-2-yl)propan-1-amine Step A: Preparation of N-(2-(3-azidopropyl)-5-(2,5-difluorophenyl)-2-phenyl-2,3-dihydro-1,3,4-thiadiazole-3-carbonothioyl)benzamide: To a solution of 2-(3-azidopropyl)-5-(2,5-difluorophenyl)-2-phenyl-2,3-dihydro-1,3,4-thiadiazole (1.00 g, 2.79 mmol) in 20 mL of anhydrous THF was added benzoyl isothiocyanate (0.45 mL, 3.34 mmol). The reaction was allowed to stir overnight at reflux, then cooled and concentrated in vacuo. The residue was purified by flash column chromatography (5-35% ethyl acetate/hexanes) to afford the desired product as a yellow gum, 1.45 g, 54%.

Step B: Preparation of 2-(3-azidopropyl)-5-(2,5-difluorophenyl)-2-phenyl-1,3,4-thiadiazole-3(2H)-carbothioamide: To a solution of N-(2-(3-azidopropyl)-5-(2,5-difluorophenyl)-2-phenyl-2,3-dihydro-1,3,4-thiadiazole-3-carbonothioyl)benzamide (0.737 g, 1.41 mmol) in 20 mL of anhydrous THF was added hydrazine (0.088 mL, 2.82 mmol). The reaction was stirred at room temperature for 3 hours, then concentrated in vacuo. The residue was purified by flash column chromatography (10-20% ethyl acetate/hexanes) to afford the desired product as a pale yellow foam, 0.504 g, 85%.

Step C: Preparation of tert-butyl 2-(2-(3-azidopropyl)-5-(2,5-difluorophenyl)-2-phenyl-1,3,4-thiadiazol-3(2H)-yl)-6,7-dihydrothiazolo[5,4-c]pyridine-5 (4H)-carboxylate: To a solution of 2-(3-azidopropyl)-5-(2,5-difluorophenyl)-2-phenyl-1,3,4-thiadiazole-3(2H)-carbothioamide (0.300 g, 0.717 mmol) in 10 mL of ethanol was added tert-butyl 3-bromo-4-oxopiperidine-1-carboxylate (0.239 g, 0.860 mmol) followed by DIEA (0.25 mL, 1.43 mmol). The mixture was allowed to stir overnight at reflux, then treated with tert-butyl 3-bromo-4-oxopiperidine-1-carboxylate (100 mg) and stirred at reflux for a further 3 hours. The cooled mixture was partitioned between a saturated NaHCO$_3$ solution (30 mL) and EtOAc (30 mL), and the aqueous layer was extracted with EtOAc (2×20 mL). The combined organic phases were washed with brine (20 mL), dried over Na$_2$SO$_4$, and concentrated in vacuo. The residue was purified by flash column chromatography (5-10% ethyl acetate/hexanes) to afford the desired product as a bright yellow foam, 0.313 g, 73%.

Step D: Preparation of 2-(2-(3-azidopropyl)-5-(2,5-difluorophenyl)-2-phenyl-1,3,4-thiadiazol-3(2H)-yl)-4,5,6,7-tetrahydrothiazolo[5,4-c]pyridine: To a solution of tert-butyl 2-(2-(3-azidopropyl)-5-(2,5-difluorophenyl)-2-phenyl-1,3,4-thiadiazol-3(2H)-yl)-6,7-dihydrothiazolo[5,4-c]pyridine-5(4H)-carboxylate (0.313 g, 0.524 mmol) in 10.0 mL of DCM at 0° C. was added TFA (1 mL). The mixture was stirred for 1 hour at 0° C. then at room temperature for 1 hour. The reaction mixture was then concentrated to dryness and partitioned between EtOAc (30 mL) and a saturated NaHCO$_3$ solution (30 mL). The aqueous layer was extracted with EtOAc (2×20 mL), and the combined organic phases were washed with brine (20 mL), dried over Na$_2$SO$_4$ and concentrated in vacuo to afford the desired product as a yellow gum, 0.251 g, 96%.

Step E: Preparation of 2-(2-(3-azidopropyl)-5-(2,5-difluorophenyl)-2-phenyl-1,3,4-thiadiazol-3(2H)-yl)-5-methyl-4,5,6,7-tetrahydrothiazolo[5,4-c]pyridine: To a solution of 2-(2-(3-azidopropyl)-5-(2,5-difluorophenyl)-2-phenyl-1,3,4-thiadiazol-3(2H)-yl)-4,5,6,7-tetrahydrothiazolo[5,4-c]pyridine (0.050 g, 0.100 mmol) in 1 mL DCE was added formaldehyde (0.033 g, 37 wt % in water, 0.401 mmol), followed by sodium triacetoxy borohydride (0.023 g, 0.110 mmol). The resulting suspension was stirred vigorously at room temperature overnight, then treated with saturated Na$_2$CO$_3$ solution (10 mL) and stirred for 10 minutes. The mixture was extracted with EtOAc (3×10 mL) and the combined organic phases were washed with brine (10 mL), dried over Na$_2$SO$_4$ and concentrated in vacuo. The residue was purified by flash column chromatography (0-3% MeOH/DCM) to afford the desired product as a yellow foam, 0.046 g, 89%.

Step F: Preparation of 3-(5-(2,5-difluorophenyl)-3-(5-methyl-4,5,6,7-tetrahydrothiazolo[5,4-c]pyridin-2-yl)-2-phenyl-2,3-dihydro-1,3,4-thiadiazol-2-yl)propan-1-amine: To a solution of 2-(2-(3-azidopropyl)-5-(2,5-difluorophenyl)-2-phenyl-1,3,4-thiadiazol-3(2H)-yl)-5-methyl-4,5,6,7-tetrahydrothiazolo[5,4-c]pyridine (0.046 g, 0.090 mmol) in 2 mL of methanol was added 1N HCl/MeOH (0.27 mL, 0.27 mmol) followed by 10% Pd/C (10 mg). The mixture was hydrogenated under a balloon atmosphere for 1 hour then filtered through GF paper, and the filtrate concentrated in vacuo. The residue was triturated with diethyl ether, filtered, washed with ether and dried in vacuo to afford the desired product as a bright yellow solid, 0.027 g, 50%. MS ESI (+) m/z 486 (M+1) detected; $^1$H NMR (400 MHz, CDCl$_3$) δ 7.59 (m, 1H), 7.45 (d, 2H, J=7.6 Hz), 7.32 (m, 2H), 7.26 (m, 1H), 7.06 (m, 2H), 3.50 (m, 2H), 3.43 (m, 1H), 2.77 (t, 2H, J=6.9 Hz), 2.68 (m, 2H), 2.56 (m, 2H), 2.46 (s, 3H), 2.41 (m, 1H), 1.99 (m, 1H), 1.55 (m, 1H) ppm.

Example 22

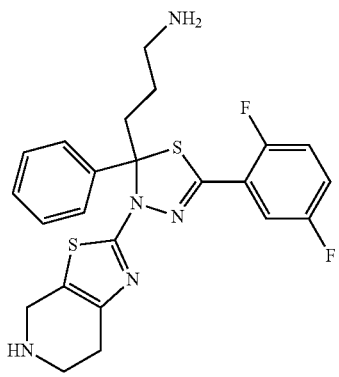 [SMILES: NCCCC1(c2ccccc2)SC(c2cc(F)ccc2F)=NN1c1nc2c(s1)CNCC2]

3-(5-(2,5-difluorophenyl)-2-phenyl-3-(4,5,6,7-tetrahydrothiazolo[5,4-c]pyridin-2-yl)-2,3-dihydro-1,3,4-thiadiazol-2-yl)propan-1-amine To a solution of 2-(2-(3-azidopropyl)-5-(2,5-difluorophenyl)-2-phenyl-1,3,4-thiadiazol-3(2H)-yl)-4,5,6,7-tetrahydrothiazolo[5,4-c]pyridine (prepared according to Example 21, Steps A-D; 0.050 g, 0.100 mmol) in 2 mL of methanol was added 1N HCl/MeOH (0.30 mL, 0.30 mmol) followed by 10% Pd/C (10 mg). The mixture was hydrogenated under a balloon atmosphere for 1 hour then filtered through GF paper, and the filtrate concentrated in vacuo. The residue was triturated with diethyl ether, filtered, washed with ether and dried in vacuo to afford the desired product as a bright yellow solid, 0.018 g, 31%. MS ESI (+) m/z 472 (M+1) detected; $^1$H NMR (400 MHz, CDCl$_3$) δ 7.59 (m, 1H), 7.46 (m, 2H), 7.33 (m, 3H), 7.05 (m, 2H), 3.88 (m, 2H), 3.46 (m, 1H), 3.06 (m, 2H), 2.79 (m, 2H), 2.44 (m, 3H), 2.01 (m, 1H), 1.57 (m, 1H) ppm.

Example 23

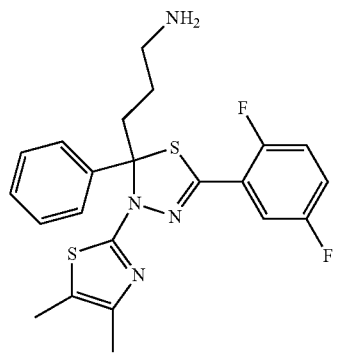 [SMILES: Cc1nc(N2N=C(c3cc(F)ccc3F)SC2(CCCN)c2ccccc2)sc1C]

3-(5-(2,5-difluorophenyl)-3-(4,5-dimethylthiazol-2-yl)-2-phenyl-2,3-dihydro-1,3,4-thiadiazol-2-yl)propan-1-amine 2-(3-Azidopropyl)-5-(2,5-difluorophenyl)-3-(4,5-dimethylthiazol-2-yl)-2-phenyl-1,3,4-thiadiazole was prepared as in Example 21, Step C, utilizing 3-chlorobutan-2-one in place of tert-butyl 3-bromo-4-oxopiperidine-1-carboxylate. Reduction of the azide as in Example 21, Step F afforded the desired product as a yellow powder, 25%. MS ESI (+) m/z 445 (M+1) detected; $^1$H NMR (400 MHz, CDCl$_3$) δ 7.59 (m, 1H), 7.47 (d, 2H, J=7.6 Hz), 7.33 (m, 3H), 7.04 (m, 2H), 3.45 (m, 1H), 2.78 (m, 2H), 2.43 (m, 1H), 2.19 (s, 3H), 1.99 (m, 1H), 1.97 (s, 3H), 1.58 (m, 1H) ppm.

Example 24

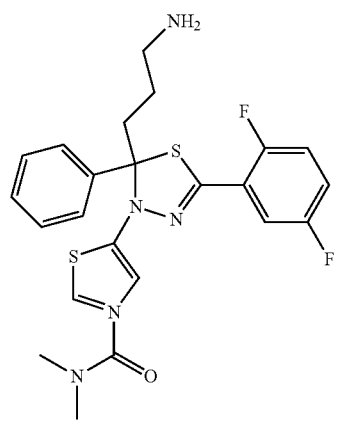

2-(2-(3-aminopropyl)-5-(2,5-difluorophenyl)-2-phenyl-1,3,4-thiadiazol-3(2H)-yl)-N,N-dimethylthiazole-4-carboxamide Step A: Preparation of ethyl 2-(2-(3-azidopropyl)-5-(2,5-difluorophenyl)-2-phenyl-1,3,4-thiadiazol-3(2H)-yl)thiazole-4-carboxylate: Prepared from 2-(3-azidopropyl)-5-(2,5-difluorophenyl)-2-phenyl-1,3,4-thiadiazole-3(2H)-carbothioamide as in Example 21, Step C, utilizing ethyl 3-bromo-2-oxopropanoate in place of tert-butyl 3-bromo-4-oxopiperidine-1-carboxylate, 57%.

Step B: Preparation of 2-(2-(3-azidopropyl)-5-(2,5-difluorophenyl)-2-phenyl-1,3,4-thiadiazol-3(2H)-yl)-N,N-dimethylthiazole-4-carboxamide: To a solution of dimethylamine (0.102 mL, 2.0 M, 0.2 mmol) in 1 mL of anhydrous THF was added trimethylaluminum (0.102 mL, 2.0 M, 0.2 mmol). The solution was stirred at room temperature for 15 minutes, then treated with a solution of ethyl 2-(2-(3-azidopropyl)-5-(2,5-difluorophenyl)-2-phenyl-1,3,4-thiadiazol-3(2H)-yl)thiazole-4-carboxylate (0.035 g, 0.07 mmol) in 0.5 mL of anhydrous THF. After stirring at room temperature for 16 hours the mixture was treated with 0.5 N aqueous Rochelle's salt solution (10 mL), then partitioned between saturated NH$_4$Cl (10 mL) and EtOAc (10 mL). The aqueous layer was extracted with EtOAc (2×10 mL) and the combined organic phases were washed with brine (10 mL), dried over Na$_2$SO$_4$ and concentrated in vacuo. The residue was purified by flash column chromatography (20-35% ethyl acetate/hexanes) to afford the desired product as a yellow gum, 0.026 g, 74%.

Step C: Preparation of 2-(2-(3-aminopropyl)-5-(2,5-difluorophenyl)-2-phenyl-1,3,4-thiadiazol-3(2H)-yl)-N,N-dimethylthiazole-4-carboxamide: 2-(2-(3-Azidopropyl)-5-(2,5-difluorophenyl)-2-phenyl-1,3,4-thiadiazol-3(2H)-yl)-N,N-dimethylthiazole-4-carboxamide (0.026 g, 0.051 mmol) was reduced as in Example 21, Step F, to afford the desired product as a yellow powder, 0.024 g, 60%. MS ESI (+) m/z 488 (M+1) detected; $^1$H NMR (400 MHz, CDCl$_3$) δ 7.63 (m, 1H), 7.50 (d, 2H, J=8 Hz), 7.31 (m, 3H), 7.24 (m, 1H), 7.10 (m, 2H), 3.29 (m, 1H), 2.92 (s, 3H), 2.78 (m, 2H), 2.51 (s, 3H), 2.41 (m, 1H), 1.99 (m, 1H), 1.51 (m, 1H) ppm.

Example 25

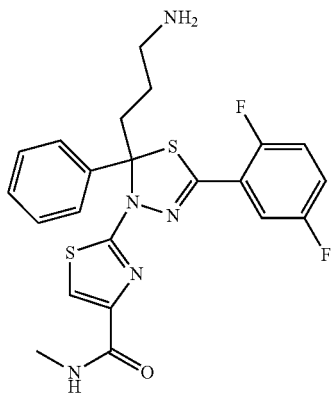 [SMILES: CNC(=O)c1csc(N2N=C(c3cc(F)ccc3F)SC2(CCCN)c2ccccc2)n1]

2-(2-(3-aminopropyl)-5-(2,5-difluorophenyl)-2-phenyl-1,3,4-thiadiazol-3(2H)-yl)-N-methylthiazole-4-carboxamide Prepared in an analogous manner to Example 24, utilizing methylamine in place of dimethylamine in Step B, to afford the desired product as a yellow solid, 80%. MS ESI (+) m/z 474 (M+1) detected; $^1$H NMR (400 MHz, CD$_3$OD) δ 7.62 (m, 1H), 7.53 (m, 3H), 7.38 (m, 2H), 7.30 (m, 3H), 3.63 (m, 1H), 3.10 (m, 2H), 2.79 (s, 3H), 2.72 (m, 1H), 2.29 (m, 1H), 1.82 (m, 1H) ppm.

Example 26

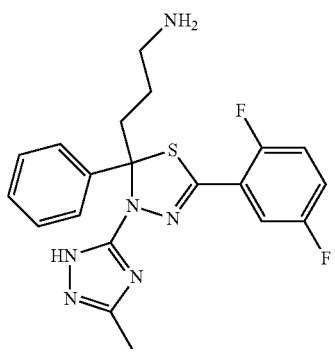 [SMILES: Cc1n[nH]c(N2N=C(c3cc(F)ccc3F)SC2(CCCN)c2ccccc2)n1]

3-(5-(2,5-difluorophenyl)-3-(3-methyl-1H-1,2,4-triazol-5-yl)-2-phenyl-2,3-dihydro-1,3,4-thiadiazol-2-yl)propan-1-amine Step A: Preparation of methyl 2-(3-azidopropyl)-5-(2,5-difluorophenyl)-2-phenyl-1,3,4-thiadiazole-3(2H)-carbimidothioate: To a solution of 2-(3-azidopropyl)-5-(2,5-difluorophenyl)-2-phenyl-1,3,4-thiadiazole-3(2H)-carbothioamide (0.120 g, 0.29 mmol) in 2 mL of a 4:1 mixture of DCM:MeOH was added methyl iodide (0.022 mL, 0.34 mmol). After stirring for 16 hours at room temperature, methyl iodide (0.050 mL) was added and the mixture stirred for a further 4 hours then concentrated in vacuo. The residue was partitioned between saturated NaHCO$_3$ (10 mL) and EtOAc (10 mL) and the aqueous layer was extracted with EtOAc (2×10 mL). The combined organic phases were washed with brine (10 mL), dried over Na$_2$SO$_4$ and concentrated in vacuo. The residue was purified by flash column chromatography (10-20% ethyl acetate/hexanes) to afford the desired product, 0.124 g, 59%.

Step B: Preparation of 2-(3-azidopropyl)-5-(2,5-difluorophenyl)-3-(3-methyl-1H-1,2,4-triazol-5-yl)-2-phenyl-2,3-dihydro-1,3,4-thiadiazole: To a solution of methyl 2-(3-azidopropyl)-5-(2,5-difluorophenyl)-2-phenyl-1,3,4-thiadiazole-3(2H)-carbimidothioate (0.034 g, 0.079 mmol) in 1 mL pyridine was added acetohydrazide (0.017 g, 0.240 mmol). The mixture was warmed to 80° C. and stirred for 16 hours, then treated with acetohydrazide (0.050 g) and stirred at reflux for 40 hours. The cooled mixture was treated with water (10 mL) and extracted with EtOAc (3×10 mL). The combined organic phases were washed with water (10 mL) and brine (10 mL), then dried over Na$_2$SO$_4$ and concentrated in vacuo. The residue was purified by flash column chromatography (10-20% ethyl acetate/hexanes) to afford the desired product as a pale yellow solid, 0.010 g, 29%.

Step C: Preparation of 3-(5-(2,5-difluorophenyl)-3-(3-methyl-1H-1,2,4-triazol-5-yl)-2-phenyl-2,3-dihydro-1,3,4-thiadiazol-2-yl)propan-1-amine: 2-(3-Azidopropyl)-5-(2,5-difluorophenyl)-3-(3-methyl-1H-1,2,4-triazol-5-yl)-2-phenyl-2,3-dihydro-1,3,4-thiadiazole (0.010 g, 0.023 mmol) was reduced as in Example 21, Step F, to afford the desired product as a pale green solid, 0.007 g, 63%. MS ESI (+) m/z 414 (M+1) detected; $^1$H NMR (400 MHz, CDCl$_3$) δ 7.45 (m, 3H), 7.33 (m, 2H), 7.27 (m, 1H), 7.20 (m, 2H), 3.30 (m, 1H), 2.97 (m, 2H), 2.62 (m, 1H), 2.24 (s, 3H), 2.18 (m, 1H), 1.74 (m, 1H) ppm.

Example 27

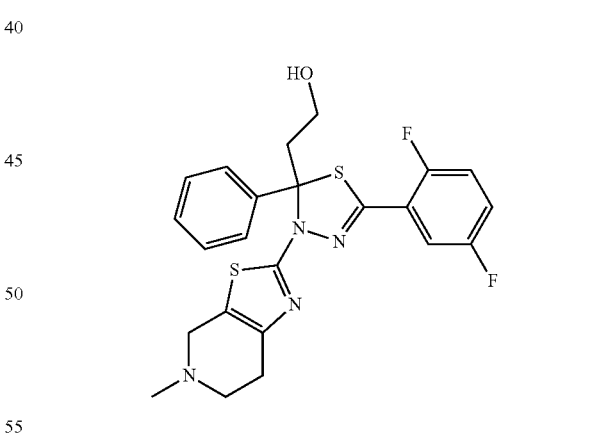

2-(5-(2,5-difluorophenyl)-3-(5-methyl-4,5,6,7-tetrahydrothiazolo[5,4-c]pyridin-2-yl)-2-phenyl-2,3-dihydro-1,3,4-thiadiazol-2-yl)ethanol Step A: Preparation of 2-(2-(tert-butyldiphenylsilyloxy)ethyl)-5-(2,5-difluorophenyl)-2-phenyl-2,3-dihydro-1,3,4-thiadiazole: To a solution of 3-(tert-butyldiphenylsilyloxy)-1-phenylpropan-1-one (1.98 g, 5.10 mmol) in 20 mL of a 3:1 mixture of EtOH:DCM was added 2,5-difluorobenzothiohydrazide (0.800 g, 4.25 mmol). The mixture was allowed to stir capped, at room temperature for 60 hours, then uncapped for 48 hours and then concentrated in vacuo. The residue was purified by flash column chromatography (Hexanes) to afford the desired product as an orange oil, 2.19 g, 92% which was contaminated with 3-(tert-butyldiphenylsilyloxy)-1-phenyl-propan-1-one. The compound was carried forward to the next step without further purification.

Step B: Preparation of N-(2-(2-(tert-butyldiphenylsilyloxy)ethyl)-5-(2,5-difluorophenyl)-2-phenyl-2,3-dihydro-1,3,4-thiadiazole-3-carbonothioyl)benzamide: To a solution of 2-(2-(tert-butyldiphenylsilyloxy)ethyl)-5-(2,5-difluorophenyl)-2-phenyl-2,3-dihydro-1,3,4-thiadiazole (1.00 g, 1.79 mmol) in 20 mL of anhydrous THF was added benzoyl isothiocyanate (0.29 mL, 2.15 mmol). The reaction was allowed to stir overnight at reflux then cooled and concentrated in vacuo. The residue was purified by flash column chromatography (5-10% ethyl acetate/hexanes) to afford the desired product as a yellow foam, 0.677 g, 52%.

Step C: Preparation of 2-(2-(tert-butyldiphenylsilyloxy)ethyl)-5-(2,5-difluorophenyl)-2-phenyl-1,3,4-thiadiazole-3(2H)-carbothioamide: To a solution of N-(2-(2-(tert-butyldiphenylsilyloxy)ethyl)-5-(2,5-difluorophenyl)-2-phenyl-2,3-dihydro-1,3,4-thiadiazole-3-carbonothioyl)benzamide (0.677 g, 0.938 mmol) in 20 mL of anhydrous THF was added hydrazine (0.060 mL, 1.87 mmol). The reaction was stirred at room temperature for 3 hours then concentrated in vacuo. The residue was purified by flash column chromatography (5-10% ethyl acetate/hexanes) to afford the desired product as a pale yellow foam, 0.502 g, 87%.

Step D: Preparation of tert-butyl 2-(2-(2-(tert-butyldiphenylsilyloxy)ethyl)-5-(2,5-difluorophenyl)-2-phenyl-1,3,4-thiadiazol-3(2H)-yl)-6,7-dihydrothiazolo[5,4-c]pyridine-5(4H)-carboxylate: To a solution of 2-(2-(tert-butyldiphenylsilyloxy)ethyl)-5-(2,5-difluorophenyl)-2-phenyl-1,3,4-thiadiazole-3(2H)-carbothioamide (0.500 g, 0.809 mmol) in 20 mL of ethanol was added tert-butyl 3-bromo-4-oxopiperidine-1-carboxylate (0.338 g, 1.21 mmol) followed by DIEA (0.423 mL, 2.43 mmol). The mixture was allowed to stir overnight at reflux then treated with tert-butyl 3-bromo-4-oxopiperidine-1-carboxylate (200 mg) and stirred at reflux for a further 3 hours. The cooled mixture was partitioned between saturated NaHCO$_3$ solution (50 mL) and EtOAc (50 mL) and the aqueous layer was extracted with EtOAc (2×50 mL). The combined organic phases were washed with brine (50 mL) dried over Na$_2$SO$_4$ and concentrated in vacuo. The residue was purified by flash column chromatography (5-10% ethyl acetate/hexanes) to afford the desired product as a viscous yellow oil, 0.412 g, 64%.

Step E: Preparation of 2-(2-(2-(tert-butyldiphenylsilyloxy)ethyl)-5-(2,5-difluorophenyl)-2-phenyl-1,3,4-thiadiazol-3(2H)-yl)-4,5,6,7-tetrahydrothiazolo[5,4-c]pyridine: To a solution of tert-butyl 2-(2-(2-(tert-butyldiphenylsilyloxy)ethyl)-5-(2,5-difluorophenyl)-2-phenyl-1,3,4-thiadiazol-3(2H)-yl)-6,7-dihydrothiazolo[5,4-c]pyridine-5(4H)-carboxylate (0.180 g, 0.226 mmol) in 4 mL of DCM at 0° C. was added TFA (1 mL). The mixture was stirred for 1 hour at 0° C. for 3 hours then concentrated in vacuo. The residue was partitioned between EtOAc (20 mL) and saturated NaHCO$_3$ solution (20 mL) and the aqueous layer was extracted with EtOAc (2×10 mL). The combined organic phases were washed with brine (10 mL), dried over Na$_2$SO$_4$ and concentrated in vacuo to afford the desired product as a yellow gum, 0.157 g, 100%.

Step F: Preparation of 2-(2-(2-(tert-butyldiphenylsilyloxy)ethyl)-5-(2,5-difluorophenyl)-2-phenyl-1,3,4-thiadiazol-3(2H)-yl)-5-methyl-4,5,6,7-tetrahydrothiazolo[5,4-c]pyridine: To a solution of 2-(2-(2-(tert-butyldiphenylsilyloxy)ethyl)-5-(2,5-difluorophenyl)-2-phenyl-1,3,4-thiadiazol-3(2H)-yl)-4,5,6,7-tetrahydrothiazol[5,4-c]pyridine (0.157 g, 0.225 mmol) in 5 mL DCE was added formaldehyde (0.067 mL, 37 wt % in water, 0.901 mmol) followed by sodium triacetoxyborohydride (0.052 g, 0.248 mmol). The resulting suspension was stirred vigorously at room temperature overnight, then treated with saturated Na$_2$CO$_3$ solution (30 mL) and stirred for 10 minutes. The mixture was extracted with EtOAc (3×30 mL) and the combined organic phases were washed with brine (20 mL), dried over Na$_2$SO$_4$ and concentrated in vacuo. The residue was purified by flash column chromatography (0-1% MeOH/DCM) to afford the desired product as a bright yellow foam, 0.119 g, 74%.

Step G: Preparation of 2-(5-(2,5-difluorophenyl)-3-(5-methyl-4,5,6,7-tetrahydrothiazolo[5,4-c]pyridin-2-yl)-2-phenyl-2,3-dihydro-1,3,4-thiadiazol-2-yl)ethanol: To a solution of 2-(2-(2-(tert-butyldiphenylsilyloxy)ethyl)-5-(2,5-difluorophenyl)-2-phenyl-1,3,4-thiadiazol-3(2H)-yl)-5-methyl-4,5,6,7-tetrahydrothiazolo[5,4-c]pyridine (0.070 g, 0.098 mmol) in 2 mL of anhydrous acetonitrile was added HF-TEA (0.160 mL, 0.99 mmol). The solution was stirred at room temperature for 16 hours then slowly quenched with saturated NaHCO$_3$ (20 mL). The mixture was extracted with EtOAc (3×10 mL) and the combined organic phases were washed with brine (10 mL), dried over Na$_2$SO$_4$ and concentrated in vacuo. The residue was purified by flash column chromatography (0-1% MeOH/DCM) and the residue was dissolved in 2 mL of methanol and treated with 1N HCl/MeOH (2 mL). After stirring for 10 minutes, the solution was concentrated in vacuo. The residue was triturated with diethyl ether, filtered, washed with ether and dried in vacuo to afford the desired product as a yellow powder, 0.023 g, 42%. MS ESI (+) m/z 473 (M+1) detected; $^1$H NMR (400 MHz, CDCl$_3$) δ 7.59 (m, 1H), 7.44 (d, 2H, J=7.5 Hz), 7.32 (m, 2H), 7.26 (m, 1H), 7.07 (m, 2H), 4.10 (m, 1H), 3.96 (m, 1H), 3.65 (m, 1H), 3.54 (q, 2H, J=30.2, 14.3 Hz), 2.83 (m, 1H), 2.72 (m, 2H), 2.57 (m, 2H), 2.48 (s, 3H) ppm.

Example 28

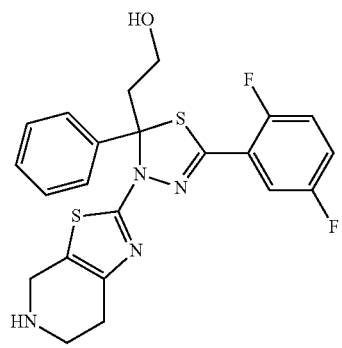 [SMILES: OCCC1(c2ccccc2)SC(c2cc(F)ccc2F)=NN1c1nc2c(s1)CNCC2]

2-(5-(2,5-difluorophenyl)-2-phenyl-3-(4,5,6,7-tetrahydrothiazolo[5,4-c]pyridin-2-yl)-2,3-dihydro-1,3,4-thiadiazol-2-yl)ethanol To a solution of tert-butyl 2-(2-(2-(tert-butyldiphenylsilyloxy)ethyl)-5-(2,5-difluorophenyl)-2-phenyl-1,3,4-thiadiazol-3(2H)-yl)-6,7-dihydrothiazolhydro[5,4-c]pyridine-5(4H)-carboxylate (prepared according to Example 26, Steps A-D; 0.090 g, 0.113 mmol) in 1 mL of 1,4-dioxane was added 4M HCl/dioxane (1 mL). The mixture was stirred at room temperature for 16 hours then treated with 4M HCl/dioxane (2 mL) and stirred for a further 3 hours. Water (1 mL) was added and the mixture was stirred for 16 hours then concentrated and dried in vacuo. The residue was triturated with diethyl ether, filtered, washed with ether and dried in vacuo to afford the desired product as an orange/yellow solid, 0.023 g, 38%. MS ESI (+) m/z 459 (M+1) detected; $^1$H NMR (400 MHz, CDCl$_3$) δ 7.59 (m, 1H), 7.46 (m, 2H), 7.33 (m, 3H), 7.07 (m, 2H), 4.12 (m, 1H), 3.95 (m, 1H), 3.87 (m, 2H), 3.65 (m, 2H), 3.05 (m, 2H), 2.84 (m, 1H), 2.43 (m, 2H) ppm.

The following compounds can also be prepared using the above described procedures, utilizing the appropriately substituted reagents.

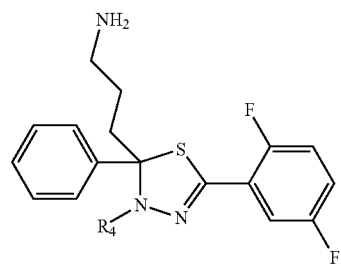

| | R$^4$ | Name |
|---|---|---|
| 29 | | 3-(5-(2,5-difluorophenyl)-2-phenyl-3-(pyridin-3-yl)-2,3-dihydro-1,3,4-thiadiazol-2-yl)propan-1-amine |
| 30 | | 3-(5-(2,5-difluorophenyl)-2-phenyl-3-(pyridin-2-yl)-2,3-dihydro-1,3,4-thiadiazol-2-yl)propan-1-amine |
| 31 | | 3-(5-(2,5-difluorophenyl)-2-phenyl-3-(pyridin-4-yl)-2,3-dihydro-1,3,4-thiadiazol-2-yl)propan-1-amine |
| 32 | | 3-(5-(2,5-difluorophenyl)-3-(3-methylpyridin-4-yl)-2-phenyl-2,3-dihydro-1,3,4-thiadiazol-2-yl)propan-1-amine |
| 33 | | 3-(5-(2,5-difluorophenyl)-3-(3-(fluoromethyl)pyridin-4-yl)-2-phenyl-2,3-dihydro-1,3,4-thiadiazol-2-yl)propan-1-amine |
| 34 | | 3-(3-(3-(difluoromethyl)pyridin-4-yl)-5-(2,5-difluorophenyl)-2-phenyl-2,3-dihydro-1,3,4-thiadiazol-2-yl)propan-1-amine |
| 35 | | 3-(5-(2,5-difluorophenyl)-2-phenyl-3-(3-(trifluoromethyl)pyridin-4-yl)-2,3-dihydro-1,3,4-thiadiazol-2-yl)propan-1-amine |

-continued

| | R⁴ | Name |
|---|---|---|
| 36 | 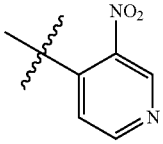 [SMILES: *c1ccncc1[N+](=O)[O-]] | 3-(5-(2,5-difluorophenyl)-3-(3-nitropyridin-4-yl)-2-phenyl-2,3-dihydro-1,3,4-thiadiazol-2-yl)propan-1-amine |
| 37 | 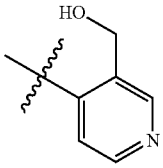 [SMILES: *c1ccncc1CO] | (4-(2-(3-aminopropyl)-5-(2,5-difluorophenyl)-2-phenyl-1,3,4-thiadiazol-3(2H)-yl)pyridin-3-yl)methanol |
| 38 | 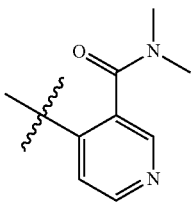 [SMILES: *c1ccncc1C(=O)N(C)C] | 4-(2-(3-aminopropyl)-5-(2,5-difluorophenyl)-2-phenyl-1,3,4-thiadiazol-3(2H)-yl)-N,N-dimethylnicotinamide |
| 39 | 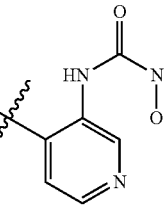 | 3-(4-(2-(3-aminopropyl)-5-(2,5-difluorophenyl)-2-phenyl-1,3,4-thiadiazol-3(2H)-yl)pyridin-3-yl)-1-methoxy-1-methylurea |
| 40 | 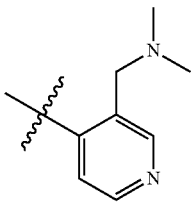 [SMILES: *c1ccncc1CN(C)C] | 3-(5-(2,5-difluorophenyl)-3-(3-((dimethylamino)methyl)pyridin-4-yl)-2-phenyl-2,3-dihydro-1,3,4-thiadiazol-2-yl)propan-1-amine |
| 41 | 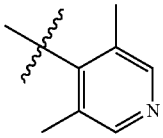 [SMILES: *c1c(C)cncc1C] | 3-(5-(2,5-difluorophenyl)-3-(3,5-dimethylpyridin-4-yl)-2-phenyl-2,3-dihydro-1,3,4-thiadiazol-2-yl)propan-1-amine |
| 42 | 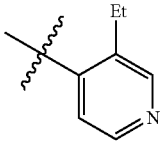 [SMILES: *c1ccncc1CC] | 3-(5-(2,5-difluorophenyl)-3-(3-ethylpyridin-4-yl)-2-phenyl-2,3-dihydro-1,3,4-thiadiazol-2-yl)propan-1-amine |
| 43 | 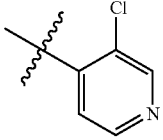 [SMILES: *c1ccncc1Cl] | 3-(3-(3-chloropyridin-4-yl)-5-(2,5-difluorophenyl)-2-phenyl-2,3-dihydro-1,3,4-thiadiazol-2-yl)propan-1-amine |

-continued

| | R⁴ | Name |
|---|---|---|
| 44 | (4-cyanopyridin-3-yl) | 4-(2-(3-aminopropyl)-5-(2,5-difluorophenyl)-2-phenyl-1,3,4-thiadiazol-3(2H)-yl)nicotinonitrile |
| 45 | (6-fluoropyridin-3-yl) | 3-(5-(2,5-difluorophenyl)-3-(2-fluoropyridin-4-yl)-2-phenyl-2,3-dihydro-1,3,4-thiadiazol-2-yl)propan-1-amine |
| 46 | (pyrimidin-2-yl) | 3-(5-(2,5-difluorophenyl)-2-phenyl-3-(pyrimidin-2-yl)-2,3-dihydro-1,3,4-thiadiazol-2-yl)propan-1-amine |
| 47 | (4-methylpyrimidin-2-yl) | 3-(5-(2,5-difluorophenyl)-3-(4-methylpyrimidin-2-yl)-2-phenyl-2,3-dihydro-1,3,4-thiadiazol-2-yl)propan-1-amine |
| 48 | (5-fluoro-4-methylpyrimidin-2-yl) | 3-(5-(2,5-difluorophenyl)-3-(5-fluoro-4-methylpyrimidin-2-yl)-2-phenyl-2,3-dihydro-1,3,4-thiadiazol-2-yl)propan-1-amine |
| 49 | (4-(hydroxymethyl)pyrimidin-2-yl) | (2-(2-(3-aminopropyl)-5-(2,5-difluorophenyl)-2-phenyl-1,3,4-thiadiazol-3(2H)-yl)pyrimidin-4-yl)methanol |
| 50 | (4-(N,N-dimethylcarboxamido)pyrimidin-2-yl) | 2-(2-(3-aminopropyl)-5-(2,5-difluorophenyl)-2-phenyl-1,3,4-thiadiazol-3(2H)-yl)-N,N-dimethylpyrimidine-4-carboxamide |
| 51 | (4-((dimethylamino)methyl)pyrimidin-2-yl) | 3-(5-(2,5-difluorophenyl)-3-(4-((dimethylamino)methyl)pyrimidin-2-yl)-2-phenyl-2,3-dihydro-1,3,4-thiadiazol-2-yl)propan-1-amine |
| 52 | (5-chloropyrimidin-2-yl) | 3-(3-(5-chloropyrimidin-2-yl)-5-(2,5-difluorophenyl)-2-phenyl-2,3-dihydro-1,3,4-thiadiazol-2-yl)propan-1-amine |
| 53 | (4-cyanopyrimidin-2-yl) | 2-(2-(3-aminopropyl)-5-(2,5-difluorophenyl)-2-phenyl-1,3,4-thiadiazol-3(2H)-yl)pyrimidine-4-carbonitrile |

-continued

| | R⁴ | Name |
|---|---|---|
| 54 | 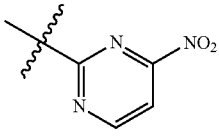 [SMILES: *c1nccc([N+](=O)[O-])n1] | 3-(5-(2,5-difluorophenyl)-3-(4-nitropyrimidin-2-yl)-2-phenyl-2,3-dihydro-1,3,4-thiadiazol-2-yl)propan-1-amine |
| 55 | 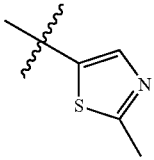 [SMILES: *c1cnc(C)s1] | 3-(5-(2,5-difluorophenyl)-3-(2-methylthiazol-5-yl)-2-phenyl-2,3-dihydro-1,3,4-thiadiazol-2-yl)propan-1-amine |
| 56 | 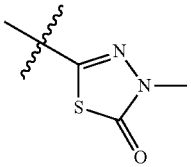 [SMILES: *c1nn(C)c(=O)s1] | 2'-(3-aminopropyl)-5'-(2,5-difluorophenyl)-4-methyl-2'-phenyl-2'H-2,3'-bi(1,3',4'-thiadiazol)-5(4H)-one |
| 57 | 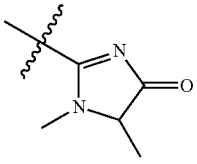 [SMILES: *C1=NC(=O)C(C)N1C] | 2-(2-(3-aminopropyl)-5-(2,5-difluorophenyl)-2-phenyl-1,3,4-thiadiazol-3(2H)-yl)-1,4-dimethyl-1H-imidazol-5(4H)-one |
| 58 | 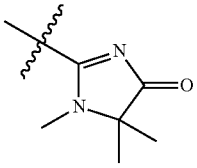 [SMILES: *C1=NC(=O)C(C)(C)N1C] | 2-(2-(3-aminopropyl)-5-(2,5-difluorophenyl)-2-phenyl-1,3,4-thiadiazol-3(2H)-yl)-1,5,5-trimethyl-1H-imidazol-4(5H)-one |
| 59 | 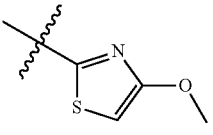 [SMILES: *c1nc(OC)cs1] | 3-(5-(2,5-difluorophenyl)-3-(4-methoxythiazol-2-yl)-2-phenyl-2,3-dihydro-1,3,4-thiadiazol-2-yl)propan-1-amine |
| 60 | 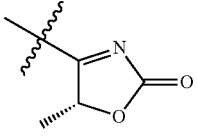 [SMILES: *C1=NC(=O)O[C@@H]1C] | (5R)-4-(2-(3-aminopropyl)-5-(2,5-difluorophenyl)-2-phenyl-1,3,4-thiadiazol-3(2H)-yl)-5-methyloxazol-2(5H)-one |
| 61 | 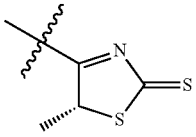 [SMILES: *C1=NC(=S)S[C@@H]1C] | (5R)-4-(2-(3-aminopropyl)-5-(2,5-difluorophenyl)-2-phenyl-1,3,4-thiadiazol-3(2H)-yl)-5-methylthiazole-2(5H)-thione |
| 62 | 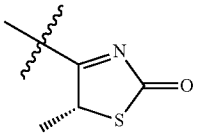 [SMILES: *C1=NC(=O)S[C@@H]1C] | (5R)-4-(2-(3-aminopropyl)-5-(2,5-difluorophenyl)-2-phenyl-1,3,4-thiadiazol-3(2H)-yl)-5-methylthiazol-2(5H)-one |

-continued

| | R⁴ | Name |
|---|---|---|
| 63 | | 4-(2-(3-aminopropyl)-5-(2,5-difluorophenyl)-2-phenyl-1,3,4-phenyl-3(2H)-yl)-1,5,5-trimethyl-1H-imidazol-2(5H)-one |
| 64 | | 4-(2-(3-aminopropyl)-5-(2,5-difluorophenyl)-2-phenyl-1,3,4-thiadiazol-3(2H)-yl)-5,5-dimethyloxazol-2(5H)-one |
| 65 | | 4-(2-(3-aminopropyl)-5-(2,5-difluorophenyl)-2-phenyl-1,3,4-thiadiazol-3(2H)-yl)-5,5-dimethylthiazol-2(5H)-one |
| 66 | | 2-(2-(3-aminopropyl)-5-(2,5-difluorophenyl)-2-phenyl-1,3,4-thiadiazol-3(2H)-yl)-5,5-dimethylthiazol-4(5H)-one |
| 67 | | 2-(2-(3-aminopropyl)-5-(2,5-difluorophenyl)-2-phenyl-1,3,4-thiadiazol-3(2H)-yl)-5,5-dimethyloxazol-4(5H)-one |
| 68 | | 5-(2-(3-aminopropyl)-5-(2,5-difluorophenyl)-2-phenyl-1,3,4-thiadiazol-3(2H)-yl)-6,6-dimethyl-2H-1,4-oxazin-3(6H)-one |
| 69 | | 5-(2-(3-aminopropyl)-5-(2,5-difluorophenyl)-2-phenyl-1,3,4-thiadiazol-3(2H)-yl)-6,6-dimethyl-2H-1,4-thiazin-3(6H)-one |
| 70 | | 3-(2-(3-aminopropyl)-5-(2,5-difluorophenyl)-2-phenyl-1,3,4-thiadiazol-3(2H)-yl)-4,4-dimethyl-6H-1,2,5-dithiazin-1,1-dioxide |
| 71 | | 3-(2-(3-aminopropyl)-5-(2,5-difluorophenyl)-2-phenyl-1,3,4-thiadiazol-3(2H)-yl)-4,4-dimethyl-6H-1,2,5-oxathiazin-1,1-dioxide |

-continued

| | R⁴ | Name |
|---|---|---|
| 72 | | 3-(2-(3-aminopropyl)-5-(2,5-difluorophenyl)-2-phenyl-1,3,4-thiadiazol-3(2H)-yl)-5-methyl-6H-1,2,4-dithiazin-1,1-dioxide |
| 73 | | 3-(2-(3-aminopropyl)-5-(2,5-difluorophenyl)-2-phenyl-1,3,4-thiadiazol-3(2H)-yl)-5-methyl-1,2,4-dithiazin-1,1-dioxide |
| 74 | | 3-(2-(3-aminopropyl)-5-(2,5-difluorophenyl)-2-phenyl-1,3,4-thiadiazol-3(2H)-yl)-5-methyl-1,2,4-oxathiazin-1,1-dioxide |
| 75 | | 2-(2-(3-aminopropyl)-5-(2,5-difluorophenyl)-2-phenyl-1,3,4-thiadiazol-3(2H)-yl)-6-methyl-4H-1,3-oxazin-4-one |
| 76 | | 2-(2-(3-aminopropyl)-5-(2,5-difluorophenyl)-2-phenyl-1,3,4-thiadiazol-3(2H)-yl)-6,6-dimethyl-5,6-dihydro-4H-1,3-thiazin-4-one |
| 77 | | 2-(2-(3-aminopropyl)-5-(2,5-difluorophenyl)-2-phenyl-1,3,4-thiadiazol-3(2H)-yl)-6,6-dimethyl-5,6-dihydro-4H-1,3-oxazin-4-one |
| 78 | | 2-(2,-3-aminopropyl)-5-(2,5-difluorophenyl)-2-phenyl-1,3,4-thiadiazol-3(2H)-yl)-5,5-dimethyl-5,6-dihydro-4H-1,3-oxazin-4-one |
| 79 | | 2-(2-(3-aminopropyl)-5-(2,5-difluorophenyl)-2-phenyl-1,3,4-thiadiazol-3(2H)-yl)-5,5-dimethyl-5,6-dihydro-4H-1,3-thiazin-4-one |

-continued

| | R⁴ | Name |
|---|---|---|
| 80 | | 3-(5-(2,5-difluorophenyl)-3-(1,4-dimethyl-1H-imidazol-2-yl)-2-phenyl-2,3-dihydro-1,3,4-thiadiazol-2-yl)propan-1-amine |
| 81 | | 3-(5-(2,5-difluorophenyl)-3-(1,5-dimethyl-1H-imidazol-2-yl)-2-phenyl-2,3-dihydro-1,3,4-thiadiazol-2-yl)propan-1-amine |
| 82 | | 3-(5-(2,5-difluorophenyl)-3-(1-methyl-1H-imidazol-2-yl)-2-phenyl-2,3-dihydro-1,3,4-thiadiazol-2-yl)propan-1-amine |
| 83 | | 3-(5-(2,5-difluorophenyl)-3-(1-methyl-1H-pyrazol-3-yl)-2-phenyl-2,3-dihydro-1,3,4-thiadiazol-2-yl)propan-1-amine |
| 84 | | 3-(5-(2,5-difluorophenyl)-3-(1,3-dimethyl-1H-pyrazol-5-yl)-2-phenyl-2,3-dihydro-1,3,4-thiadiazol-2-yl)propan-1-amine |
| 85 | | 3-(5-(2,5-difluorophenyl)-3-(1,4-dimethyl-1H-pyrazol-5-yl)-2-phenyl-2,3-dihydro-1,3,4-thiadiazol-2-yl)propan-1-amine |
| 86 | | 3-(5-(2,5-difluorophenyl)-3-(4-methyl-1H-pyrazol-5-yl)-2-phenyl-2,3-dihydro-1,3,4-thiadiazol-2-yl)propan-1-amine |
| 87 | | 3-(5-(2,5-difluorophenyl)-3-(4-methylthiazol-5-yl)-2-phenyl-2,3-dihydro-1,3,4-thiadiazol-2-yl)propan-1-amine |
| 88 | | 3-(5-(2,5-difluorophenyl)-3-(5-methylthiazol-4-yl)-2-phenyl-2,3-dihydro-1,3,4-thiadiazol-2-yl)propan-1-amine |
| 89 | | 3-(5-(2,5-difluorophenyl)-3-(2-methylthiazol-4-yl)-2-phenyl-2,3-dihydro-1,3,4-thiadiazol-2-yl)propan-1-amine |

-continued

| | R⁴ | Name |
|---|---|---|
| 90 | | 3-(5-(2,5-difluorophenyl)-3-(4-methyl-4H-1,2,4-triazol-3-yl)-2-phenyl-2,3-dihydro-1,3,4-thiadiazol-2-yl)propan-1-amine |
| 91 | | 3-(5-(2,5-difluorophenyl)-3-(4,5-dimethyl-4H-1,2,4-triazol-3-yl)-2-phenyl-2,3-dihydro-1,3,4-thiadiazol-2-yl)propan-1-amine |
| 92 | | 5-(2-(3-aminopropyl)-5-(2,5-difluorophenyl)-2-phenyl-1,3,4-thiadiazol-3(2H)-yl)-2-methyl-1,2,4-thiadiazol-3(2H)-one |
| 93 | | 3-(5-(2,5-difluorophenyl)-3-(1-methyl-1H-imidazol-4-yl)-2-phenyl-2,3-dihydro-1,3,4-thiadiazol-2-yl)propan-1-amine |
| 94 | | 3-(5-(2,5-difluorophenyl)-3-(1,5-dimethyl-1H-imidazol-4-yl)-2-phenyl-2,3-dihydro-1,3,4-thiadiazol-2-yl)propan-1-amine |
| 95 | | 3-(5-(2,5-difluorophenyl)-3-(1,2-dimethyl-1H-imidazol-4-yl)-2-phenyl-2,3-dihydro-1,3,4-thiadiazol-2-yl)propan-1-amine |
| 96 | | 3-(5-(2,5-difluorophenyl)-2-phenyl-3-(1,2,5-trimethyl-1H-imidazol-4-yl)-2,3-dihydro-1,3,4-thiadiazol-2-yl)propan-1-amine |
| 97 | | 3-(5-(2,5-difluorophenyl)-3-(1,2-dimethyl-1H-imidazol-5-yl)-2-phenyl-2,3-dihydro-1,3,4-thiadiazol-2-yl)propan-1-amine |
| 98 | | 3-(5-(2,5-difluorophenyl)-3-(1,4-dimethyl-1H-imidazol-5-yl)-2-phenyl-2,3-dihydro-1,3,4-thiadiazol-2-yl)propan-1-amine |

-continued

| | R⁴ | Name |
|---|---|---|
| 99 | 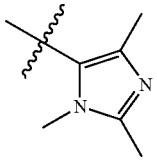 [SMILES: *c1c(C)nc(C)n1C] | 3-(5-(2,5-difluorophenyl)-2-phenyl-3-(1,2,4-trimethyl-1H-imidazol-5-yl)-2,3-dihydro-1,3,4-thiadiazol-2-yl)propan-1-amine |
| 100 | 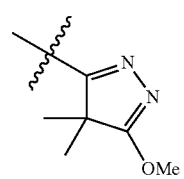 [SMILES: *C1=NN=C(OC)C1(C)C] | 3-(5-(2,5-difluorophenyl)-3-(5-methoxy-4,4-dimethyl-4H-pyrazol-3-yl)-2-phenyl-2,3-dihydro-1,3,4-thiadiazol-2-yl)propan-1-amine |
| 101 | 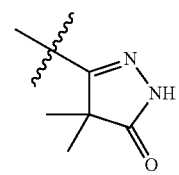 [SMILES: *C1=NNC(=O)C1(C)C] | 3-(2-(3-aminopropyl)-5-(2,5-difluorophenyl)-2-phenyl-1,3,4-thiadiazol-3(2H)-yl)-4,4-dimethyl-1H-pyrazol-5(4H)-one |
| 102 | 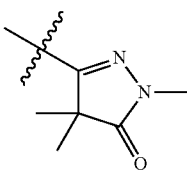 | 3-(2-(3-aminopropyl)-5-(2,5-difluorophenyl)-2-phenyl-1,3,4-thiadiazol-3(2H)-yl)-1,4,4-trimethyl-1H-pyrazol-5(4H)-one |
| 103 | 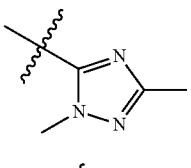 | 3-(5-(2,5-difluorophenyl)-3-(1,3-dimethyl-1H-1,2,4-triazol-5-yl)-2-phenyl-2,3-dihydro-1,3,4-thiadiazol-2-yl)propan-1-amine |
| 104 | 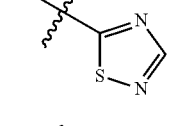 | 3-(5-(2,5-difluorophenyl)-2-phenyl-3-(1,2,4-thiadiazol-5-yl)-2,3-dihydro-1,3,4-thiadiazol-2-yl)propan-1-amine |
| 105 | 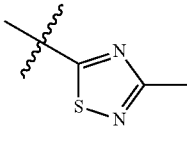 [SMILES: *c1nc(C)ns1] | 3-(5-(2,5-difluorophenyl)-3-(3-methyl-1,2,4-thiadiazol-5-yl)-2-phenyl-2,3-dihydro-1,3,4-thiadiazol-2-yl)propan-1-amine |
| 106 | 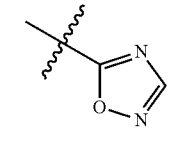 [SMILES: *c1ncno1] | 3-(5-(2,5-difluorophenyl)-3-(1,2,4-oxadiazol-5-yl)-2-phenyl-2,3-dihydro-1,3,4-thiadiazol-2-yl)propan-1-amine |
| 107 | 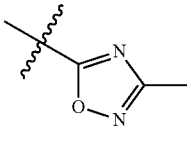 [SMILES: *c1nc(C)no1] | 3-(5-(2,5-difluorophenyl)-3-(3-methyl-1,2,4-oxadiazol-5-yl)-2-phenyl-2,3-dihydro-1,3,4-thiadiazol-2-yl)propan-1-amine |
| 108 | 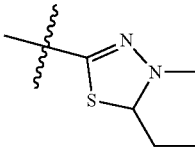 | 3-(5-(2,5-difluorophenyl)-2-phenyl-3-(6,7,8,8a-tetrahydro-5H-[1,3,4]thiadiazolo[3,2-a]pyridin-2-yl)-2,3-dihydro-1,3,4-thiadiazol-2-yl)propan-1-amine |

-continued

| | R⁴ | Name |
|---|---|---|
| 109 | | 3-(5-(2,5-difluorophenyl)-3-(8a-methyl-6,7,8,8a-tetrahydro-5H-[1,3,4]thiadiazolo[3,2-a]pyridin-2-yl)-2-phenyl-2,3-dihydro-1,3,4-thiadiazol-2-yl)propan-1-amine |
| 110 | | 2-(2-(3-aminopropyl)-5-(2,5-difluorophenyl)-2-phenyl-1,3,4-thiadiazol-3(2H)-yl)-8a-methyl-6,7,8,8a-tetrahydro-5H-[1,3,4]thiadiazolo[3,2-a]pyridin-5-one |
| 111 | | 2-(2-(3-aminopropyl)-5-(2,5-difluorophenyl)-2-phenyl-1,3,4-thiadiazol-3(2H)-yl)-8a-methyl-6,7,8,8a-tetrahydro-5H-[1,3,4]oxadiazolo[3,2-a]pyridin-5-one |
| 112 | | 2-(2-(3-aminopropyl)-5-(2,5-difluorophenyl)-2-phenyl-1,3,4-thiadiazol-3(2H)-yl)-5,7,8,8a-tetrahydro-[1,3,4]thiadiazolo[3,2-c][1,3]thiazin-6,6-dioxide |
| 113 | | 2-(2-(3-aminopropyl)-5-(2,5-difluorophenyl)-2-phenyl-1,3,4-thiadiazol-3(2H)-yl)-7-methyl-5,7,8,8a-tetrahydro-[1,3,4]thiadiazolo[2,3-d][1,2,5]thiadiazin-6,6-dioxide |
| 114 | | 3-(5-(2,5-difluorophenyl)-3-(7-methyl-6,7,8,8a-tetrahydro-5H-[1,3,4]thiadiazolo[3,2-a]pyrazin-2-yl)-2-phenyl-2,3-dihydro-1,3,4-thiadiazol-2-yl)propan-1-amine |
| 115 | | 3-(5-(2,5-difluorophenyl)-3-(4-fluoro-5-methyl-4,5,6,7-tetrahydrothiazolo[4,5-c]pyridin-2-yl)-2-phenyl-2,3-dihydro-1,3,4-thiadiazol-2-yl)propan-1-amine |
| 116 | | 3-(5-(2,5-difluorophenyl)-3-(7-fluoro-5-methyl-4,5,6,7-tetrahydrothiazolo[5,4-c]pyridin-2-yl)-2-phenyl-2,3-dehydro-1,3,4-thiadiazol-2-yl)propan-1-amine |

-continued

| | R⁴ | Name |
|---|---|---|
| 117 | (structure) | 2-(2-(2-(3-aminopropyl)-5-(2,5-difluorophenyl)-2-phenyl-1,3,4-thiadiazol-3(2H)-yl)-4-fluoro-6,7-dihydrothiazolo[4,5-c]pyridin-5(4H)-yl)ethanol |
| 118 | (structure) | 2-(2-(2-(3-aminopropyl)-5-(2,5-difluorophenyl)-2-phenyl-1,3,4-thiadiazol-3(2H)-yl)-4-fluoro-6,7-dihydrothiazolo[4,5-c]pyridin-5(4H)-yl)ethyl dihydrogen |
| 119 | (structure) | 3-(5-(2,5-difluorophenyl)-3-(5-(2-(dimethylamino)ethyl)-4-fluoro-4,5,6,7-tetrahydrothiazolo[4,5-c]pyridin-2-yl)-2-phenyl-2,3-dihydro-1,3,4-thiadiazol-2-yl)propan-1-amine |
| 120 | (structure) | 2-(2-(3-aminopropyl)-5-(2,5-difluorophenyl)-2-phenyl-1,3,4-thiadiazol-3(2H)-yl)-4-fluoro-N-methoxy-N-methyl-6,7-dihydrothiazolo[4,5-c]pyridine-5(4H)-carboxamide |
| 121 | (structure) | 2-(2-(3-aminopropyl)-5-(2,5-difluorophenyl)-2-phenyl-1,3,4-thiadiazol-3(2H)-yl)-N-cyano-4-fluoro-6,7-dihydrothiazolo[4,5-c]pyridine-5(4H)-carboximidamide |
| 122 | (structure) | 3-(5-(2,5-difluorophenyl)-3-(5-(4-morpholinobutyl)-4,5,6,7-tetrahydrothiazolo[4,5-c]pyridin-2-yl)-2-phenyl-2,3-dihydro-1,3,4-thiadiazol-2-yl)propan-1-amine |
| 123 | (structure) | 3-(5-(2,5-difluorophenyl)-3-(5-(3-morpholinopropyl)-4,5,6,7-tetrahydrothiazolo[4,5-c]pyridin-2-yl)-2-phenyl-2,3-dihydro-1,3,4-thiadiazol-2-yl)propan-1-amine |
| 124 | (structure) | 3-(5-(2,5-difluorophenyl)-3-(4-(fluoromethyl)-5-methyl-4,5,6,7-tetrahydrothiazolo[4,5-c]pyridin-2-yl)-2-phenyl-2,3-dihydro-1,3,4-thiadiazol-2-yl)propan-1-amine |

| | R⁴ | Name |
|---|---|---|
| 125 | | 3-(3-(4-(difluoromethyl)-5-methyl-4,5,6,7-tetrahydrothiazolo[4,5-c]pyridin-2-yl)-5-(2,5-difluorophenyl)-2-phenyl-2,3-dihydro-1,3,4-thiadiazol-2-yl)propan-1-amine |
| 126 | | 3-(5-(2,5-difluorophenyl)-3-(5-methyl-4-(trifluoromethyl)-4,5,6,7-tetrahydrothiazolo[4,5-c]pyridin-2-yl)-2-phenyl-2,3-dihydro-1,3,4-thiadiazol-2-yl)propan-1-amine |
| 127 | | 3-(5-(2,5-difluorophenyl)-3-(5,7-dimethyl-4,5,6,7-tetrahydrothiazolo[4,5-c]pyridin-2-yl)-2-phenyl-2,3-dihydro-1,3,4-thiadiazol-2-yl)propan-1-amine |
| 128 | | 3-(5-(2,5-difluorophenyl)-3-(4-methyl-4,5,6,7-tetrahydrothiazolo[5,4-b]pyridin-2-yl)-2-phenyl-2,3-dihydro-1,3,4-thiadiazol-2-yl)propan-1-amine |
| 129 | | 2-(2-(3-aminopropyl)-5-(2,5-difluorophenyl)-2-phenyl-1,3,4-thiadiazol-3(2H)-yl)-N,N,4-trimethyl-4,5,6,7-tetrahydrothiazolo[4,5-b]pyridine-6-carboxamide |
| 130 | | 3-(5-(2,5-difluorophenyl)-3-(5-methyl-5,6-dihydro-4H-pyrrolo[3,4-d]thiazol-2-yl)-2-phenyl-2,3-dihydro-1,3,4-thiadiazol-2-yl)propan-1-amine |
| 131 | | 3-(5-(2,5-difluorophenyl)-3-(5-(methylsulfonyl)-5,6-dihydro-4H-pyrrolo[3,4-d]thiazol-2-yl)-2-phenyl-2,3-dihydro-1,3,4-thiadiazol-2-yl)propan-1-amine |
| 132 | | 3-(5-(2,5-difluorophenyl)-3-(4,6-dihydrothieno-5,5-dioxo-[3,4-d]thiazol-2-yl)-2-phenyl-2,3-dihydro-1,3,4-thiadiazol-2-yl)propan-1-amine |

-continued

| | R⁴ | Name |
|---|---|---|
| 133 | | 3-(5-(2,5-difluorophenyl)-3-(4-methyl-5,6-dihydro-4H-pyrrolo[2,3-d]thiazol-2-yl)-2-phenyl-2,3-dihydro-1,3,4-thiadiazol-2-yl)propan-1-amine |
| 134 | | 3-(5-(2,5-difluorophenyl)-3-(1-methyl-1,3-dihydroisothiazolo-2,2-dioxo-[3,4-d]thiazol-5-yl)-2-phenyl-2,3-dihydro-1,3,4-thiadiazol-2-yl)propan-1-amine |
| 135 | | 3-(5-(2,5-difluorophenyl)-3-(4-methyl-5,6-dihydro-4H-pyrrolo[3,2-d]thiazol-2-yl)-2-phenyl-2,3-dihydro-1,3,4-thiadiazol-2-yl)propan-1-amine |
| 136 | | 3-(5-(2,5-difluorophenyl)-3-(1-methyl-1,3-dihydroisothiazolo-2,2-dioxo-[4,3-d]thiazol-5-yl)-2-phenyl-2,3-dihydro-1,3,4-thiadiazol-2-yl)propan-1-amine |
| 137 | | 3-(5-(2,5-difluorophenyl)-3-(4-methyl-4H-pyrrolo[3,2-d]thiazol-2-yl)-2-phenyl-2,3-dihydro-1,3,4-thiadiazol-2-yl)propan-1-amine |
| 138 | | 3-(5-(2,5-difluorophenyl)-3-(1-methyl-1H-pyrazolo[4,3-d]thiazol-5-yl)-2-phenyl-2,3-dihydro-1,3,4-thiadiazol-2-yl)propan-1-amine |
| 139 | | 3-(5-(2,5-difluorophenyl)-3-(2-methyl-2H-thieno[2,3-c]pyrazol-5-yl)-2-phenyl-2,3-dihydro-1,3,4-thiadiazol-2-yl)propan-1-amine |
| 140 | | 3-(5-(2,5-difluorophenyl)-3-(4-fluoro-5-methyl-5,6-dihydro-4H-pyrrolo[3,4-d]thiazol-2-yl)-2-phenyl-2,3-dihydro-1,3,4-thiadiazol-2-yl)propan-1-amine |

| | R⁴ | Name |
|---|---|---|
| 141 | benzo[d]thiazol-2-yl | 3-(3-(benzo[d]thiazol-2-yl)-5-(2,5-difluorophenyl)-2-phenyl-2,3-dihydro-1,3,4-thiadiazol-2-yl)propan-1-amine |
| 142 | 4-methylbenzo[d]thiazol-2-yl | 3-(5-(2,5-difluorophenyl)-3-(4-methylbenzo[d]thiazol-2-yl)-2-phenyl-2,3-dihydro-1,3,4-thiadiazol-2-yl)propan-1-amine |
| 143 | 7-methylbenzo[d]thiazol-2-yl | 3-(5-(2,5-difluorophenyl)-3-(7-methylbenzo[d]thiazol-2-yl)-2-phenyl-2,3-dihydro-1,3,4-thiadiazol-2-yl)propan-1-amine |
| 144 | 6-methylbenzo[d]thiazol-2-yl | 3-(5-(2,5-difluorophenyl)-3-(6-methylbenzo[d]thiazol-2-yl)-2-phenyl-2,3-dihydro-1,3,4-thiadiazol-2-yl)propan-1-amine |
| 145 | 5-methylbenzo[d]thiazol-2-yl | 3-(5-(2,5-difluorophenyl)-3-(5-methylbenzo[d]thiazol-2-yl)-2-phenyl-2,3-dihydro-1,3,4-thiadiazol-2-yl)propan-1-amine |
| 146 | 7-ethylbenzo[d]thiazol-2-yl | 3-(5-(2,5-difluorophenyl)-3-(7-ethylbenzo[d]thiazol-2-yl)-2-phenyl-2,3-dihydro-1,3,4-thiadiazol-2-yl)propan-1-amine |
| 147 | 7-fluorobenzo[d]thiazol-2-yl | 3-(5-(2,5-difluorophenyl)-3-(7-fluorobenzo[d]thiazol-2-yl)-2-phenyl-2,3-dihydro-1,3,4-thiadiazol-2-yl)propan-1-amine |
| 148 | 4-fluorobenzo[d]thiazol-2-yl | 3-(5-(2,5-difluorophenyl)-3-(4-fluorobenzo[d]thiazol-2-yl)-2-phenyl-2,3-dihydro-1,3,4-thiadiazol-2-yl)propan-1-amine |

-continued

| | R⁴ | Name |
|---|---|---|
| 149 | (5-chlorobenzo[d]thiazol-2-yl, attached at 2-position, Cl at 5) | 3-(3-(5-chlorobenzo[d]thiazol-2-yl)-5-(2,5-difluorophenyl)-2-phenyl-2,3-dihydro-1,3,4-thiadiazol-2-yl)propan-1-amine |
| 150 | (6-chlorobenzo[d]thiazol-2-yl) | 3-(3-(6-chlorobenzo[d]thiazol-2-yl)-5-(2,5-difluorophenyl)-2-phenyl-2,3-dihydro-1,3,4-thiadiazol-2-yl)propan-1-amine |
| 151 | (6-ethylbenzo[d]thiazol-2-yl) | 3-(5-(2,5-difluorophenyl)-3-(6-ethylbenzo[d]thiazol-2-yl)-2-phenyl-2,3-dihydro-1,3,4-thiadiazol-2-yl)propan-1-amine |
| 152 | (6-cyanobenzo[d]thiazol-2-yl) | 2-(2-(3-aminopropyl)-5-(2,5-difluorophenyl)-2-phenyl-1,3,4-thiadiazol-3(2H)-yl)benzo[d]thiazole-6-carbonitrile |
| 153 | (6-nitrobenzo[d]thiazol-2-yl) | 3-(5-(2,5-difluorophenyl)-3-(6-nitrobenzo[d]thiazol-2-yl)-2-phenyl-2,3-dihydro-1,3,4-thiadiazol-2-yl)propan-1-amine |
| 154 | (6-(3,3-dimethylureido)benzo[d]thiazol-2-yl) | 3-(2-(2-(3-aminopropyl)-5-(2,5-difluorophenyl)-2-phenyl-1,3,4-thiadiazol-3(2H)-yl)benzo[d]thiazol-6-yl)-1,1-dimethylurea |
| 155 | (6-(N,N-dimethylcarboxamido)benzo[d]thiazol-2-yl) | 2-(2-(3-aminopropyl)-5-(2,5-difluorophenyl)-2-phenyl-1,3,4-thiadiazol-3(2H)-yl)-N,N-dimethylbenzo[d]thiazole-6-carboxamide |

| | R⁴ | Name |
|---|---|---|
| 156 | benzo[d]thiazol-6-yl with CH₂OH at 6-position | (2-(2-(3-aminopropyl)-5-(2,5-difluorophenyl)-2-phenyl-1,3,4-thiadiazol-3(2H)-yl)benzo[d]thiazol-6-yl)methanol |
| 157 | benzo[d]thiazol-2-yl with CH₂N(CH₃)₂ at 6-position | 3-(5-(2,5-difluorophenyl)-3-(6-((dimethylamino)methyl)benzo[d]thiazol-2-yl)-2-phenyl-2,3-dihydro-1,3,4-thiadiazol-2-yl)propan-1-amine |
| 158 | benzo[d]thiazol-2-yl with CH₂NHC(O)N(OCH₃)(CH₃) at 6-position | 3-((2-(2-(3-aminopropyl)-5-(2,5-difluorophenyl)-2-phenyl-1,3,4-thiadiazol-3(2H)-yl)benzo[d]thiazol-6-yl)methyl)-1-methoxy-1-methylurea |
| 159 | benzo[d]thiazol-2-yl with 3-methyl-1,2,4-triazol-1-yl at 6-position | 3-(5-(2,5-difluorophenyl)-3-(6-(3-methyl-1H-1,2,4-triazol-1-yl)benzo[d]thiazol-2-yl)-2-phenyl-2,3-dihydro-1,3,4-thiadiazol-2-yl)propan-1-amine |
| 160 | benzo[d]oxazol-2-yl | 3-(3-(benzo[d]oxazol-2-yl)-5-(2,5-difluorophenyl)-2-phenyl-2,3-dihydro-1,3,4-thiadiazol-2-yl)propan-1-amine |
| 161 | 1-methyl-1H-benzo[d]imidazol-2-yl | 3-(5-(2,5-difluorophenyl)-3-(1-methyl-1H-benzo[d]imidazol-2-yl)-2-phenyl-2,3-dihydro-1,3,4-thiadiazol-2-yl)propan-1-amine |

-continued

| | R⁴ | Name |
|---|---|---|
| 162 | 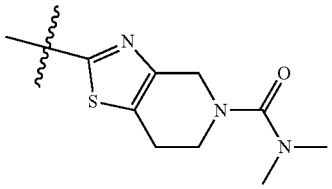 [SMILES: *c1nc2c(s1)CCN(C(=O)N(C)C)C2] | 2-(2-(3-aminopropyl)-5-(2,5-difluorophenyl)-2-phenyl-1,3,4-thiadiazol-3(2H)-yl)-N,N-dimethyl-6,7-dihydrothiazolo[4,5-c]pyridine-5(4H)-carboxamide |
| 163 | 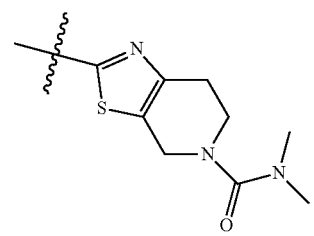 [SMILES: *c1nc2c(s1)CN(C(=O)N(C)C)CC2] | 2-(2-(3-aminopropyl)-5-(2,5-difluorophenyl)-2-phenyl-1,3,4-thiadiazol-3(2H)-yl)-N,N-dimethyl-6,7-dihydrothiazolo[5,4-c]pyridine-5(4H)-carboxamide |
| 164 | 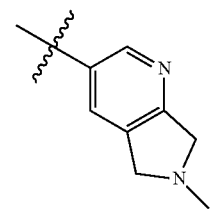 [SMILES: *c1cnc2c(c1)CN(C)C2] | 3-(5-(2,5-difluorophenyl)-3-(6-methyl-6,7-dihydro-5H-pyrrolo[3,4-b]pyridin-3-yl)-2-phenyl-2,3-dihydro-1,3,4-thiadiazol-2-yl)propan-1-amine |
| 165 | 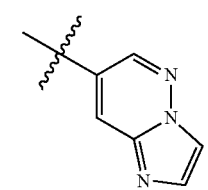 [SMILES: *c1cnn2ccnc2c1] | 3-(5-(2,5-difluorophenyl)-3-(imidazo[1,2-b]pyridazin-7-yl)-2-phenyl-2,3-dihydro-1,3,4-thiadiazol-2-yl)propan-1-amine |
| 166 | 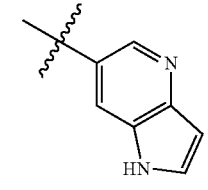 [SMILES: *c1cnc2cc[nH]c2c1] | 3-(5-(2,5-difluorophenyl)-2-phenyl-3-(1H-pyrrolo[3,2-b]pyridin-6-yl)-2,3-dihydro-1,3,4-thiadiazol-2-yl)propan-1-amine |
| 167 | 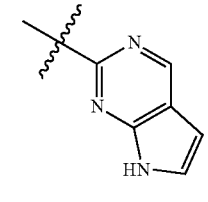 [SMILES: *c1ncc2cc[nH]c2n1] | 3-(5-(2,5-difluorophenyl)-2-phenyl-3-(7H-pyrrolo[2,3-d]pyrimidin-2-yl)-2,3-dihydro-1,3,4-thiadiazol-2-yl)propan-1-amine |
| 168 | 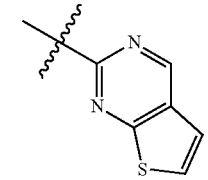 [SMILES: *c1ncc2ccsc2n1] | 3-(5-(2,5-difluorophenyl)-2-phenyl-3-(thieno[2,3-d]pyrimidin-2-yl)-2,3-dihydro-1,3,4-thiadiazol-2-yl)propan-1-amine |

-continued

| | R⁴ | Name |
|---|---|---|
| 169 | (thieno[2,3-d]pyrimidine with methyl) | 3-(5-(2,5-difluorophenyl)-3-(6-methylthieno[2,3-d]pyrimidin-2-yl)-2-phenyl-2,3-dihydro-1,3,4-thiadiazol-2-yl)propan-1-amine |
| 170 | (pyrrolo[2,3-b]pyridine with methyl) | 3-(5-(2,5-difluorophenyl)-3-(2-methyl-1H-pyrrolo[2,3-b]pyridin-6-yl)-2-phenyl-2,3-dihydro-1,3,4-thiadiazol-2-yl)propan-1-amine |
| 171 | (imidazo[1,2-a]pyrimidine with methyl) | 3-(5-(2,5-difluorophenyl)-3-(2-methylimidazo[1,2-a]pyrimidin-7-yl)-2-phenyl-2,3-dihydro-1,3,4-thiadiazol-2-yl)propan-1-amine |
| 172 | (4H-benzo[e][1,3]oxazine sulphone) | 2-(2-(3-aminopropyl)-5-(2,5-difluorophenyl)-2-phenyl-1,3,4-thiadiazol-3(2H)-yl)-4H-benzo[e][1,3]oxazin-4-sulphone |
| 173 | (4H-benzo[e][1,3]thiazine sulphone) | 2-(2-(3-aminopropyl)-5-(2,5-difluorophenyl)-2-phenyl-1,3,4-thiadiazol-3(2H)-yl)-4H-benzo[e][1,3]thiazin-4-sulphone |
| 174 | (4H-benzo[e][1,3]thiazin-4-one) | 2-(2-(3-aminopropyl)-5-(2,5-difluorophenyl)-2-phenyl-1,3,4-thiadiazol-3(2H)-yl)-4H-benzo[e][1,3]thiazin-4-one |
| 175 | (6-methyl-6,7-dihydropyrrolo[3,4-e][1,3]thiazin-4(5H)-one) | 2-(2-(3-aminopropyl)-5-(2,5-difluorophenyl)-2-phenyl-1,3,4-thiadiazol-3(2H)-yl)-6-methyl-6,7-dihydropyrrolo[3,4-e][1,3]thiazin-4(5H)-one |

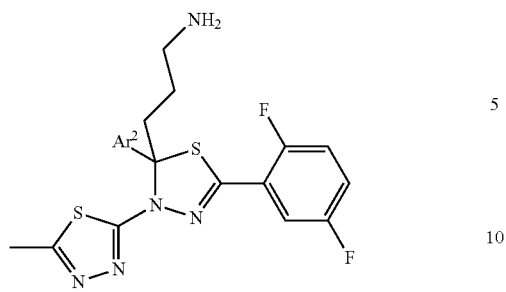

| | Ar² | Name |
|---|---|---|
| 176 | 2-methylphenyl | 3-(5-(2,5-difluorophenyl)-3-(5-methyl-1,3,4-thiadiazol-2-yl)-2-o-tolyl-2,3-dihydro-1,3,4-thiadiazol-2-yl)propan-1-amine |
| 177 | 3-methylphenyl | 3-(5-(2,5-difluorophenyl)-3-(5-methyl-1,3,4-thiadiazol-2-yl)-2-m-tolyl-2,3-dihydro-1,3,4-thiadiazol-2-yl)propan-1-amine |
| 178 | 4-methylphenyl | 3-(5-(2,5-difluorophenyl)-3-(5-methyl-1,3,4-thiadiazol-2-yl)-2-p-tolyl-2,3-dihydro-1,3,4-thiadiazol-2-yl)propan-1-amine |
| 179 | 3,4-dimethylphenyl | 3-(5-(2,5-difluorophenyl)-2-(3,4-dimethylphenyl)-3-(5-methyl-1,3,4-thiadiazol-2-yl)-2,3-dihydro-1,3,4-thiadiazol-2-yl)propan-1-amine |
| 180 | 3,5-dimethylphenyl | 3-(5-(2,5-difluorophenyl)-2-(3,5-dimethylphenyl)-3-(5-methyl-1,3,4-thiadiazol-2-yl)-2,3-dihydro-1,3,4-thiadiazol-2-yl)propan-1-amine |
| 181 | 2-ethylphenyl | 3-(5-(2,5-difluorophenyl)-2-(2-ethylphenyl)-3-(5-methyl-1,3,4-thiadiazol-2-yl)-2,3-dihydro-1,3,4-thiadiazol-2-yl)propan-1-amine |
| 182 | 3-ethylphenyl | 3-(5-(2,5-difluorophenyl)-2-(3-ethylphenyl)-3-(5-methyl-1,3,4-thiadiazol-2-yl)-2,3-dihydro-1,3,4-thiadiazol-2-yl)propan-1-amine |
| 183 | 4-t-butylphenyl | 3-(2-(4-tert-butylphenyl)-5-(2,5-difluorophenyl)-3-(5-methyl-1,3,4-thiadiazol-2-yl)-2,3-dihydro-1,3,4-thiadiazol-2-yl)propan-1-amine |
| 184 | 2-chlorophenyl | 3-(2-(2-chlorophenyl)-5-(2,5-difluorophenyl)-3-(5-methyl-1,3,4-thiadiazol-2-yl)-2,3-dihydro-1,3,4-thiadiazol-2-yl)propan-1-amine |
| 185 | 4-chlorophenyl | 3-(2-(4-chlorophenyl)-5-(2,5-difluorophenyl)-3-(5-methyl-1,3,4-thiadiazol-2-yl)-2,3-dihydro-1,3,4-thiadiazol-2-yl)propan-1-amine |
| 186 | 3-fluorophenyl | 3-(5-(2,5-difluorophenyl)-2-(3-fluorophenyl)-3-(5-methyl-1,3,4-thiadiazol-2-yl)-2,3-dihydro-1,3,4-thiadiazol-2-yl)propan-1-amine |
| 187 | 4-fluorophenyl | 3-(5-(2,5-difluorophenyl)-2-(4-fluorophenyl)-3-(5-methyl-1,3,4-thiadiazol-2-yl)-2,3-dihydro-1,3,4-thiadiazol-2-yl)propan-1-amine |
| 188 | 4-bromophenyl | 3-(2-(4-bromophenyl)-5-(2,5-difluorophenyl)-3-(5-methyl-1,3,4-thiadiazol-2-yl)-2,3-dihydro-1,3,4-thiadiazol-2-yl)propan-1-amine |
| 189 | 3,4-dichlorophenyl | 3-(2-(3,4-dichlorophenyl)-5-(2,5-difluorophenyl)-3-(5-methyl-1,3,4-thiadiazol-2-yl)-2,3-dihydro-1,3,4-thiadiazol-2-yl)propan-1-amine |
| 190 | 3-nitrophenyl | 3-(5-(2,5-difluorophenyl)-3-(5-methyl-1,3,4-thiadiazol-2-yl)-2-(3-nitrophenyl)-2,3-dihydro-1,3,4-thiadiazol-2-yl)propan-1-amine |
| 191 | 3-hydroxyphenyl | 3-(2-(3-aminopropyl)-5-(2,5-difluorophenyl)-3-(5-methyl-1,3,4-thiadiazol-2-yl)-2,3-dihydro-1,3,4-thiadiazol-2-yl)phenol |
| 192 | ![phosphate structure] | 3-(2-(3-aminopropyl)-5-(2,5-difluorophenyl)-3-(5-methyl-1,3,4-thiadiazol-2-yl)-2,3-dihydro-1,3,4-thiadiazol-2-yl)phenyl dihydrogen phosphate |
| 193 | 3-aminophenyl | 3-(2-(3-aminopropyl)-5-(2,5-difluorophenyl)-3-(5-methyl-1,3,4-thiadiazol-2-yl)-2,3-dihydro-1,3,4-thiadiazol-2-yl)aniline |

-continued

| | Ar² | Name |
|---|---|---|
| 194 | 3-carboxyphenyl | 3-(2-(3-aminopropyl)-5-(2,5-difluorophenyl)-3-(5-methyl-1,3,4-thiadiazol-2-yl)-2,3-dihydro-1,3,4-thiadiazol-2-yl)benzoic acid |
| 195 | 3-cyanophenyl | 3-(2-(3-aminopropyl)-5-(2,5-difluorophenyl)-3-(5-methyl-1,3,4-thiadiazol-2-yl)-2,3-dihydro-1,3,4-thiadiazol-2-yl)benzonitrile |
| 196 | 2-pyridyl | 3-(5-(2,5-difluorophenyl)-3-(5-methyl-1,3,4-thiadiazol-2-yl)-2-(pyridin-2-yl)-2,3-dihydro-1,3,4-thiadiazol-2-yl)propan-1-amine |
| 197 | 3-pyridyl | 3-(5-(2,5-difluorophenyl)-3-(5-methyl-1,3,4-thiadiazol-2-yl)-2-(pyridin-3-yl)-2,3-dihydro-1,3,4-thiadiazol-2-yl)propan-1-amine |
| 198 | 5-methylthiophen-2-yl | 3-(5-(2,5-difluorophenyl)-3-(5-methyl-1,3,4-thiadiazol-2-yl)-2-(5-methylthiophen-2-yl)-2,3-dihydro-1,3,4-thiadiazol-2-yl)propan-1-amine |
| 199 | 2-methylthiazol-4-yl | 3-(5-(2,5-difluorophenyl)-2-methylthiazol-4-yl-3-(5-methyl-1,3,4-thiadiazol-2-yl)-2,3-dihydro-1,3,4-thiadiazol-2-yl)propan-1-amine |
| 200 | 2-(1H-imidazol-2-yl) | 3-(5-(2,5-difluorophenyl)-2-(1H-imidazol-2-yl)-3-(5-methyl-1,3,4-thiadiazol-2-yl)-2,3-dihydro-1,3,4-thiadiazol-2-yl)propan-1-amine |
| 201 | 2-(1H-imidazol-4-yl) | 3-(5-(2,5-difluorophenyl)-2-(1H-imidazol-4-yl)-3-(5-methyl-1,3,4-thiadiazol-2-yl)-2,3-dihydro-1,3,4-thiadiazol-2-yl)propan-1-amine |
| 202 | 3-amino-1H-pyrazol-5-yl | 3-(5-(2,5-difluorophenyl)-3-amino-1H-pyrazol-5-yl-3-(5-methyl-1,3,4-thiadiazol-2-yl)-2,3-dihydro-1,3,4-thiadiazol-2-yl)propan-1-amine |

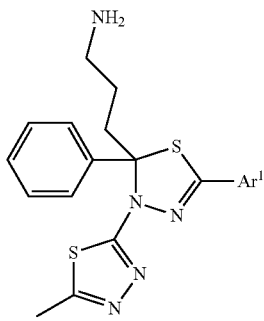

| | Ar¹ | Name |
|---|---|---|
| 203 | 2-fluorophenyl | 3-(5-(2-fluorophenyl)-3-(5-methyl-1,3,4-thiadiazol-2-yl)-2-phenyl-2,3-dihydro-1,3,4-thiadiazol-2-yl)propan-1-amine |
| 204 | 3-fluorophenyl | 3-(5-(3-fluorophenyl)-3-(5-methyl-1,3,4-thiadiazol-2-yl)-2-phenyl-2,3-dihydro-1,3,4-thiadiazol-2-yl)propan-1-amine |
| 205 | 2-chlorophenyl | 3-(5-(2-chlorophenyl)-3-(5-methyl-1,3,4-thiadiazol-2-yl)-2-phenyl-2,3-dihydro-1,3,4-thiadiazol-2-yl)propan-1-amine |
| 206 | 3-chlorophenyl | 3-(5-(3-chlorophenyl)-3-(5-methyl-1,3,4-thiadiazol-2-yl)-2-phenyl-2,3-dihydro-1,3,4-thiadiazol-2-yl)propan-1-amine |
| 207 | 2,5-dichlorophenyl | 3-(5-(2,5-dichlorophenyl)-3-(5-methyl-1,3,4-thiadiazol-2-yl)-2-phenyl-2,3-dihydro-1,3,4-thiadiazol-2-yl)propan-1-amine |
| 208 | 2,3-dichlorophenyl | 3-(5-(2,3-dichlorophenyl)-3-(5-methyl-1,3,4-thiadiazol-2-yl)-2-phenyl-2,3-dihydro-1,3,4-thiadiazol-2-yl)propan-1-amine |
| 209 | 3,4-dichlorophenyl | 3-(5-(3,4-dichlorophenyl)-3-(5-methyl-1,3,4-thiadiazol-2-yl)-2-phenyl-2,3-dihydro-1,3,4-thiadiazol-2-yl)propan-1-amine |
| 210 | 3,5-dichlorophenyl | 3-(5-(3,5-dichlorophenyl)-3-(5-methyl-1,3,4-thiadiazol-2-yl)-2-phenyl-2,3-dihydro-1,3,4-thiadiazol-2-yl)propan-1-amine |

-continued

| | Ar¹ | Name |
|---|---|---|
| 211 | 2-chloro-5-fluorophenyl | 3-(5-(2-chloro-5-fluorophenyl)-3-(5-methyl-1,3,4-thiadiazol-2-yl)-2-phenyl-2,3-dihydro-1,3,4-thiadiazol-2-yl)propan-1-amine |
| 212 | 2-fluoro-5-chlorophenyl | 3-(5-(5-chloro-2-fluorophenyl)-3-(5-methyl-1,3,4-thiadiazol-2-yl)-2-phenyl-2,3-dihydro-1,3,4-thiadiazol-2-yl)propan-1-amine |
| 213 | 2-chloro-5-methylphenyl | 3-(5-(2-chloro-5-methylphenyl)-3-(5-methyl-1,3,4-thiadiazol-2-yl)-2-phenyl-2,3-dihydro-1,3,4-thiadiazol-2-yl)propan-1-amine |
| 214 | 2-trifluoromethyl-5-fluorophenyl | 3-(5-(5-fluoro-2-(trifluoromethyl)phenyl)-3-(5-methyl-1,3,4-thiadiazol-2-yl)-2-phenyl-2,3-dihydro-1,3,4-thiadiazol-2-yl)propan-1-amine |
| 215 | 2-fluoro-5-methoxyphenyl | 3-(5-(2-fluoro-5-methoxyphenyl)-3-(5-methyl-1,3,4-thiadiazol-2-yl)-2-phenyl-2,3-dihydro-1,3,4-thiadiazol-2-yl)propan-1-amine |
| 216 | thiophen-2-yl | 3-(3-(5-methyl-1,3,4-thiadiazol-2-yl)-2-phenyl-5-(thiophen-2-yl)-2,3-dihydro-1,3,4-thiadiazol-2-yl)propan-1-amine |
| 217 | thiophen-3-yl | 3-(3-(5-methyl-1,3,4-thiadiazol-2-yl)-2-phenyl-5-(thiophen-3-yl)-2,3-dihydro-1,3,4-thiadiazol-2-yl)propan-1-amine |
| 218 | 5-chlorothiophen-2-yl | 3-(5-(5-chlorothiophen-2-yl)-3-(5-methyl-1,3,4-thiadiazol-2-yl)-2-phenyl-2,3-dihydro-1,3,4-thiadiazol-2-yl)propan-1-amine |
| 219 | 2-pyridyl | 3-(3-(5-methyl-3,4-thiadiazol-2-yl)-2-phenyl-5-(pyridin-2-yl)-2,3-dihydro-1,3,4-thiadiazol-2-yl)propan-1-amine |
| 220 | 3-pyridyl | 3-(3-(5-methyl-1,3,4-thiadiazol-2-yl)-2-pheny-5-(pyridin-3-yl)-2,3-dihydro-1,3,4-thiadiazol-2-yl)propan-1-amine |
| 221 | 4-chloropyridin-3-yl | 3-(5-(4-chloropyridin-3-yl)-3-(5-methyl-1,3,4-thiadiazol-2-yl)-2-phenyl-2,3-dihydro-1,3,4-thiadiazol-2-yl)propan-1-amine |
| 222 | 3-chloropyridin-2-yl | 3-(5-(3-chloropyridin-2-yl)-3-(5-methyl-1,3,4-thiadiazol-2-yl)-2-phenyl-2,3-dihydro-1,3,4-thiadiazol-2-yl)propan-1-amine |
| 223 | 4-fluoropyridin-3-yl | 3-(5-(4-fluoropyridin-3-yl)-3-(5-methyl-1,3,4-thiadiazol-2-yl)-2-phenyl-2,3-dihydro-1,3,4-thiadiazol-2-yl)propan-1-amine |

-continued

| | Ar¹ | Name | |
|---|---|---|---|
| 224 | 3,6-difluoro pyridin-2-yl | 3-(5-(3,6-difluoropyridin-2-yl)-3-(5-methyl-1,3,4-thiadiazol-2-yl)-2-phenyl-2,3-dihydro-1,3,4-thiadiazol-2-yl)propan-1-amine | |

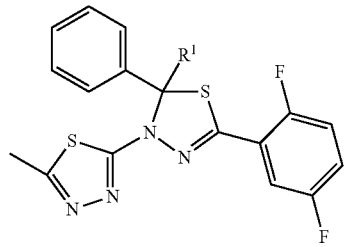

| | R¹ | Name |
|---|---|---|
| 225 | (CH₂)₃NH(CH₃) group | 3-(5-(2,5-difluorophenyl)-3-(5-methyl-1,3,4-thiadiazol-2-yl)-2-phenyl-2,3-dihydro-1,3,4-thiadiazol-2-yl)-N-methylpropan-1-amine |
| 226 | (CH₂)₂NH₂ group | 2-(5-(2,5-difluorophenyl)-3-(5-methyl-1,3,4-thiadiazol-2-yl)-2-phenyl-2,3-dihydro-1,3,4-thiadiazol-2-yl)ethanamine |
| 227 | CH₂NH₂ group | (5-(2,5-difluorophenyl)-3-(5-methyl-1,3,4-thiadiazol-2-yl)-2-phenyl-2,3-dihydro-1,3,4-thiadiazol-2-yl)methanamine |
| 228 | (CH₂)₃NH-iPr group | 3-(5-(2,5-difluorophenyl)-3-(5-methyl-1,3,4-thiadiazol-2-yl)-2-phenyl-2,3-dihydro-1,3,4-thiadiazol-2-yl)-N-isopropylpropan-1-amine |
| 229 | (CH₂)₂NHCH₃ group | 2-(5-(2,5-difluorophenyl)-3-(5-methyl-1,3,4-thiadiazol-2-yl)-2-phenyl-2,3-dihydro-1,3,4-thiadiazol-2-yl)-N-methylethanamine |
| 230 | (CH₂)₂N(CH₃)₂ group | 2-(5-(2,5-difluorophenyl)-3-(5-methyl-1,3,4-thiadiazol-2-yl)-2-phenyl-2,3-dihydro-1,3,4-thiadiazol-2-yl)-N,N-dimethylethanamine |
| 231 | (CH₂)₃-pyrrolidin-1-yl group | 2-(5-(2,5-difluorophenyl)-2-phenyl-2-(3-(pyrrolidin-1-yl)propyl)-1,3,4-thiadiazol-3(2H)-yl)-5-methyl-1,3,4-thiadiazole |
| 232 | (CH₂)₃-piperidin-1-yl group | 2-(5-(2,5-difluorophenyl)-2-phenyl-2-(3-(piperidin-1-yl)propyl)-1,3,4-thiadiazol-3(2H)-yl)-5-methyl-1,3,4-thiadiazole |
| 233 | (CH₂)₃-(4-methylpiperazin-1-yl) group | 2-(5-(2,5-difluorophenyl)-2-(3-(4-methylpiperazin-1-yl)propyl)-2-phenyl-1,3,4-thiadiazol-3(2H)-yl)-5-methyl-1,3,4-thiadiazole |

-continued

| | R¹ | Name |
|---|---|---|
| 234 | 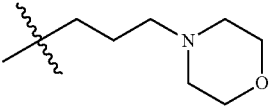 [SMILES: *CCCN1CCOCC1] | 4-(3-(5-(2,5-difluorophenyl)-3-(5-methyl-1,3,4-thiadiazol-2-yl)-2-phenyl-2,3-dihydro-1,3,4-thiadiazol-2-yl)propyl)morpholine |
| 235 | 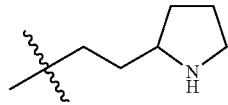 [SMILES: *CCC1CCCN1] | 2-(5-(2,5-difluorophenyl)-2-phenyl-2-(2-(pyrrolidin-2-yl)ethyl)-1,3,4-thiadiazol-3(2H)-yl)-5-methyl-1,3,4-thiadiazole |
| 236 | 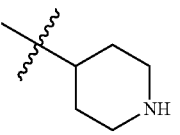 [SMILES: *C1CCNCC1] | 2-(5-(2,5-difluorophenyl)-2-phenyl-2-(piperidin-4-yl)-1,3,4-thiadiazol-3(2H)-yl)-5-methyl-1,3,4-thiadiazole |
| 237 | 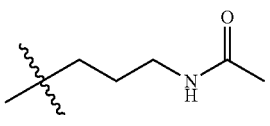 [SMILES: *CCCNC(C)=O] | N-(3-(5-(2,5-difluorophenyl)-3-(5-methyl-1,3,4-thiadiazol-2-yl)-2-phenyl-2,3-dihydro-1,3,4-thiadiazol-2-yl)propyl)acetamide |
| 238 | 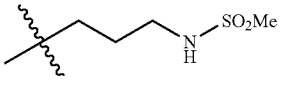 [SMILES: *CCCNS(C)(=O)=O] | N-(3-(5-(2,5-difluorophenyl)-3-(5-methyl-1,3,4-thiadiazol-2-yl)-2-phenyl-2,3-dihydro-1,3,4-thiadiazol-2-yl)propyl)methanesulfonamide |
| 239 | 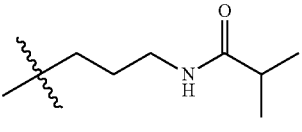 [SMILES: *CCCNC(=O)C(C)C] | N-(3-(5-(2,5-difluorophenyl)-3-(5-methyl-1,3,4-thiadiazol-2-yl)-2-phenyl-2,3-dihydro-1,3,4-thiadiazol-2-yl)propyl)isobutyramide |
| 240 | 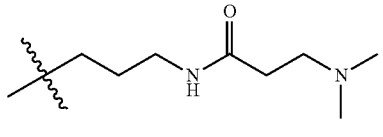 [SMILES: *CCCNC(=O)CCN(C)C] | N-(3-(5-(2,5-difluorophenyl)-3-(5-methyl-1,3,4-thiadiazol-2-yl)-2-phenyl-2,3-dihydro-1,3,4-thiadiazol-2-yl)propyl)-3-(dimethylamino)propanamide |
| 241 | 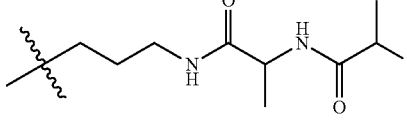 | 2-amino-N-(1-(3-(5-(2,5-difluorophenyl)-3-(5-methyl-134-thiadizol-2-yl)2phenyl-2,3-dihydro-1,3,4-thiadiazol-2-yl)propylamino)-1-oxopropan-2-yl)propanamide |
| 242 | 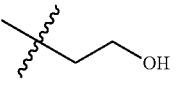 [SMILES: *CCO] | 2-(5-(2,5-difluorophenyl)-3-(5-methyl-1,3,4-thiadiazol-2-yl)-2-phenyl-2,3-dihydro-1,3,4-thiadiazol-2-yl)ethanol |
| 243 | 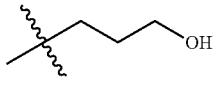 [SMILES: *CCCO] | 3-(5-(2,5-difluorophenyl)-3-(5-methyl-1,3,4-thiadiazol-2-yl)-2-phenyl-2,3-dihydro-1,3,4-thiadiazol-2-yl)propan-1-ol |
| 244 | 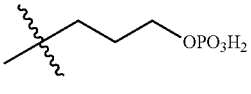 | 3-(5-(2,5-difluorophenyl)-3-(5-methyl-1,3,4-thiadiazol-2-yl)-2-phenyl-2,3-dihydro-1,3,4-thiadiazol-2-yl)propyl dihydrogen phosphate |

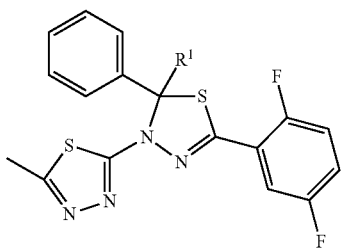

| | R[1] | Name |
|---|---|---|
| 245 | (CH2)2-NH-C(=NH)-CH3 | N-(2-(5-(2,5-difluorophenyl)-3-(5-methyl-1,3,4-thiadiazol-2-yl)-2-phenyl-2,3-dihydro-1,3,4-thiadiazol-2-yl)ethyl)acetimidamide |
| 246 | (CH2)3-NH-C(=NH)-CH3 | N-(3-(5-(2,5-difluorophenyl)-3-(5-methyl-1,3,4-thiadiazol-2-yl)-2-phenyl-2,3-dihydro-1,3,4-thiadiazol-2-yl)propyl)acetimidamide |
| 247 | CH2-NH-C(=NH)-CH3 | N-((5-(2,5-difluorophenyl)-3-(5-methyl-1,3,4-thiadiazol-2-yl)-2-phenyl-2,3-dihydro-1,3,4-thiadiazol-2-yl)methyl)acetimidamide |
| 248 | (CH2)3-NH-C(=NOMe)-CH3 | (E)-N-(3-(5-(2,5-difluorophenyl)-3-(5-methyl-1,3,4-thiadiazol-2-yl)-2-phenyl-2,3-dihydro-1,3,4-thiadiazol-2-yl)propyl)-N'-methoxyacetimidamide |
| 249 | (CH2)3-NH-C(=NCN)-CH3 | (E)-N'-cyano-N-(3-(5-(2,5-difluorophenyl)-3-(5-methyl-1,3,4-thiadiazol-2-yl)-2-phenyl-2,3-dihydro-1,3,4-thiadiazol-2-yl)propyl)acetimidamide |
| 250 | (CH2)3-NH-C(=NH)-CH2F | N-(3-(5-(2,5-difluorophenyl)-3-(5-methyl-1,3,4-thiadiazol-2-yl)-2-phenyl-2,3-dihydro-1,3,4-thiadiazol-2-yl)propyl)-2-fluoroacetimidamide |
| 251 | (CH2)3-NH-C(NH2)=CH-NO2 | (E)-N-(3-(5-(2,5-difluorophenyl)-3-(5-methyl-1,3,4-thiadiazol-2-yl)-2-phenyl-2,3-dihydro-1,3,4-thiadiazol-2-yl)propyl)-2-nitroethene-1,1-diamine |
| 252 | (CH2)3-NH-C(NH2)=N-CN | 1-(3-(5-(2,5-difluorophenyl)-3-(5-methyl-1,3,4-thiadiazol-2-yl)-2-phenyl-2,3-dihydro-1,3,4-thiadiazol-2-yl)propyl)guanidine |
| 253 | (CH2)2-NH-C(NH2)=N-CN | (Z)-2-cyano-1-(2-(5-(2,5-difluorophenyl)-3-(5-methyl-1,3,4-thiadiazol-2-yl)-2-phenyl-2,3-dihydro-1,3,4-thiadiazol-2-yl)ethyl)guanidine |

-continued

| | R¹ | Name |
|---|---|---|
| 254 | (structure) | (E)-2-cyano-1-((5-(2,5-difluorophenyl)-3-(5-methyl-1,3,4-thiadiazol-2-yl)-2-phenyl-2,3-dihydro-1,3,4-thiadiazol-2-yl)methyl)guanidine |
| 255 | (structure) | (E)-1-(amino(3-(5-(2,5-difluorophenyl)-3-(5-methyl-1,3,4-thiadiazol-2-yl)-2-phenyl-2,3-dihydro-1,3,4-thiadiazol-2-yl)propylamino)methylene)urea |
| 256 | (structure) | (Z)-1-(amino(2-(5-(2,5-difluorophenyl)-3-(5-methyl-1,3,4-thiadiazol-2-yl)-2-phenyl-2,3-dihydro-1,3,4-thiadiazol-2-yl)ethylamino)methylene)urea |
| 257 | (structure) | (E)-1-(amino((5-(2,5-difluorophenyl)-3-(5-methyl-1,3,4-thiadiazol-2-yl)-2-phenyl-2,3-dihydro-1,3,4-thiadiazol-2-yl)methylamino)methylene)urea |
| 257 | (structure) | (Z)-N-(amino(3-(5-(2,5-difluorophenyl)-3-(5-methyl-1,3,4-thiadiazol-2-yl)-2-phenyl-2,3-dihydro-1,3,4-thiadiazol-2-yl)propylamino)methylene)acetamide |
| 259 | (structure) | (E)-N-(N'-cyano-N-(3-(5-(2,5-difluorophenyl)-3-(5-methyl-1,3,4-thiadiazol-2-yl)-2-phenyl-2,3-dihydro-1,3,4-thiadiazol-2-yl)propyl)carbamimidoyl)acetamide |
| 260 | (structure) | (E)-N,N'-((3-(5-(2,5-difluorophenyl)-3-(5-methyl-1,3,4-thiadiazol-2-yl)-2-phenyl-2,3-dihydro-1,3,4-thiadiazol-2-yl)propylamino)methanediylidene)diacetamide |
| 261 | (structure) | (Z)-1-(3-(5-(2,5-difluorophenyl)-3-(5-methyl-1,3,4-thiadiazol-2-yl)-2-phenyl-2,3-dihydro-1,3,4-thiadiazol-2-yl)propyl)-2-methoxyguanidine |
| 262 | (structure) | (Z)-1-(3-(5-(2,5-difluorophenyl)-3-(5-methyl-1,3,4-thiadiazol-2-yl)-2-phenyl-2,3-dihydro-1,3,4-thiadiazol-2-yl)propyl)-2-methylguanidine |
| 263 | (structure) | 1-(3-(5-(2,5-difluorophenyl)-3-(5-methyl-1,3,4-thiadiazol-2-yl)-2-phenyl-2,3-dihydro-1,3,4-thiadiazol-2-yl)propyl)-1-methoxyguanidine |

| | R¹ | Name |
|---|---|---|
| 264 | *structure: chain-NH-C(=NH)-N(CH₃)₂* | 3-(3-(5-(2,5-difluorophenyl)-3-(5-methyl-1,3,4-thiadiazol-2-yl)-2-phenyl-2,3-dihydro-1,3,4-thiadiazol-2-yl)propyl)-1,1-dimethylguanidine |
| 265 | *structure: chain-NH-C(=N-CH₃)-NH-CH₃* | (Z)-1-(3-(5-(2,5-difluorophenyl)-3-(5-methyl-1,3,4-thiadiazol-2-yl)-2-phenyl-2,3-dihydro-1,3,4-thiadiazol-2-yl)propyl)-2,3-dimethylguanidine |
| 266 | *structure: chain-N(tetrahydropyrimidin-2-imine)* | 1-(3-(5-(2,5-difluorophenyl)-3-(5-methyl-1,3,4-thiadiazol-2-yl)-2-phenyl-2,3-dihydro-1,3,4-thiadiazol-2-yl)propyl)tetrahydropyrimidin-2(1H)-imine |
| 267 | *structure: chain-NH-(tetrahydropyrimidin-2-yl)* | N-(3-(5-(2,5-difluorophenyl)-3-(5-methyl-1,3,4-thiadiazol-2-yl)-2-phenyl-2,3-dihydro-1,3,4-thiadiazol-2-yl)propyl)-1,4,5,6-tetrahydropyrimidin-2-amine |
| 268 | *structure: chain-NH-C(=NH)-N(pyrrolidine)* | N-(3-(5-(2,5-difluorophenyl)-3-(5-methyl-1,3,4-thiadiazol-2-yl)-2-phenyl-2,3-dihydro-1,3,4-thiadiazol-2-yl)propyl)pyrrolidine-1-carboximidamide |
| 270 | *structure: chain-C(=NH)-NH₂* | 4-(5-(2,5-difluorophenyl)-3-(5-methyl-1,3,4-thiadiazol-2-yl)-2-phenyl-2,3-dihydro-1,3,4-thiadiazol-2-yl)butanimidamide |
| 271 | *structure: longer chain-C(=NH)-NH₂* | 5-(5-(2,5-difluorophenyl)-3-(5-methyl-1,3,4-thiadiazol-2-yl)-2-phenyl-2,3-dihydro-1,3,4-thiadiazol-2-yl)pentanimidamide |
| 272 | *structure: shorter chain-C(=NH)-NH₂* | 3-(5-(2,5-difluorophenyl)-3-(5-methyl-1,3,4-thiadiazol-2-yl)-2-phenyl-2,3-dihydro-1,3,4-thiadiazol-2-yl)propanimidamide |
| 273 | *structure: chain-C(=N-OCH₃)-NH₂* | (Z)-4-(5-(2,5-difluorophenyl)-3-(5-methyl-1,3,4-thiadiazol-2-yl)-2-phenyl-2,3-dihydro-1,3,4-thiadiazol-2-yl)-N'-methoxybutanimidamide |
| 274 | *structure: chain-C(=N-CN)-NH₂* | (Z)-N'-cyano-4-(5-(2,5-difluorophenyl)-3-(5-methyl-1,3,4-thiadiazol-2-yl)-2-phenyl-2,3-dihydro-1,3,4-thiadiazol-2-yl)butanimidamide |
| 275 | *structure: chain-CF₂-C(=NH)-NH₂* | 4-(5-(2,5-difluorophenyl)-3-(5-methyl-1,3,4-thiadiazol-2-yl)-2-phenyl-2,3-dihydro-1,3,4-thiadiazol-2-yl)-2,2-difluorobutanimidamide |

-continued

| | R¹ | Name |
|---|---|---|
| 276 | (structure: -CH₂-O-CH₂-C(=NH)NH₂) | 2-((5-(2,5-difluorophenyl)-3-(5-methyl-1,3,4-thiadiazol-2-yl)-2-phenyl-2,3-dihydro-1,3,4-thiadiazol-2-yl)methoxy)acetimidamide |
| 277 | (structure: -(CH₂)₃-C(=NH)NHCH₃) | 4-(5-(2,5-difluorophenyl)-3-(5-methyl-1,3,4-thiadiazol-2-yl)-2-phenyl-2,3-dihydro-1,3,4-thiadiazol-2-yl)-N-methylbutanimidamide |
| 278 | (structure: -(CH₂)₂-O-NH-C(=NH)NH₂) | 1-(2-(5-(2,5-difluorophenyl)-3-(5-methyl-1,3,4-thiadiazol-2-yl)-2-phenyl-2,3-dihydro-1,3,4-thiadiazol-2-yl)ethoxy)guanidine |
| 280 | (structure: -(CH₂)₂-O-NH-C(=NH)NHCH₃) | 1-(2-(5-(2,5-difluorophenyl)-3-(5-methyl-1,3,4-thiadiazol-2-yl)-2-phenyl-2,3-dihydro-1,3,4-thiadiazol-2-yl)ethoxy)-3-methylguanidine |
| 281 | (structure: -(CH₂)₂-O-NH-C(=NH)NHC(=O)CH₃) | N-(N-(2-(5-(2,5-difluorophenyl)-3-(5-methyl-1,3,4-thiadiazol-2-yl)-2-phenyl-2,3-dihydro-1,3,4-thiadiazol-2-yl)ethoxy)carbamimidoyl)acetamide |
| 282 | (structure: -(CH₂)₂-O-NH-tetrahydropyrimidin-2-yl) | O-(2-(5-(2,5-difluorophenyl)-3-(5-methyl-1,3,4-thiadiazol-2-yl)-2-phenyl-2,3-dihydro-1,3,4-thiadiazol-2-yl)ethyl)-N-(1,4,5,6-tetrahydropyrimidin-2-yl)hydroxylamine |
| 283 | (structure: -(CH₂)₂-O-N=C(CH₃)NH₂) | N-(2-(5-(2,5-difluorophenyl)-3-(5-methyl-1,3,4-thiadiazol-2-yl)-2-phenyl-2,3-dihydro-1,3,4-thiadiazol-2-yl)ethoxy)acetimidamide |
| 284 | (structure: -(CH₂)₂-O-NH-C(CH₃)=N-CH₃) | (E)-N-(2-(5-(2,5-difluorophenyl)-3-(5-methyl-1,3,4-thiadiazol-2-yl)-2-phenyl-2,3-dihydro-1,3,4-thiadiazol-2-yl)ethoxy)-N'-methylacetimidamide |
| 285 | (structure: -(CH₂)₂-O-NH-C(CH₃)=N-C(=O)CH₃) | (E)-N-(1-(2-(5-(2,5-difluorophenyl)-3-(5-methyl-1,3,4-thiadiazol-2-yl)-2-phenyl-2,3-dihydro-1,3,4-thiadiazol-2-yl)ethoxyamino)ethylidene)acetamide |
| 286 | (structure: -(CH₂)₂-NH-NH-C(CH₃)=NH) | N'-(2-(5-(2,5-difluorophenyl)-3-(5-methyl-1,3,4-thiadiazol-2-yl)-2-phenyl-2,3-dihydro-1,3,4-thiadiazol-2-yl)ethyl)acetimidohydrazide |

| | R¹ | Name |
|---|---|---|
| 287 | (structure) | (E)-N'-(2-(5-(2,5-difluorophenyl)-3-(5-methyl-1,3,4-thiadiazol-2-yl)-2-phenyl-2,3-dihydro-1,3,4-thiadiazol-2-yl)ethyl)-N'-methylacetimidohydrazide |
| 288 | (structure) | (E)-N-(1-(2-(2-(5-(2,5-difluorophenyl)-3-(5-methyl-1,3,4-thiadiazol-2-yl)-2-phenyl-2,3-dihydro-1,3,4-thiadiazol-2-yl)ethyl)hydrazinyl)ethylidene)acetamide |
| 289 | (structure) | N'-(2-(5-(2,5-difluorophenyl)-3-(5-methyl-1,3,4-thiadiazol-2-yl)-2-phenyl-2,3-dihydro-1,3,4-thiadiazol-2-yl)ethyl)-N'-methylacetimidohydrazide |
| 290 | (structure) | 2-(2-(5-(2,5-difluorophenyl)-3-(5-methyl-1,3,4-thiadiazol-2-yl)-2-phenyl-2,3-dihydro-1,3,4-thiadiazol-2-yl)ethyl)hydrazinecarboximidamide |
| 291 | (structure) | 2-(2-(5-(2,5-difluorophenyl)-3-(5-methyl-1,3,4-thiadiazol-2-yl)-2-phenyl-2,3-dihydro-1,3,4-thiadiazol-2-yl)ethyl)-N-methylhydrazinecarboximidamide |
| 292 | (structure) | N-((2-(2-(5-(2,5-difluorophenyl)-3-(5-methyl-1,3,4-thiadiazol-2-yl)-2-phenyl-2,3-dihydro-1,3,4-thiadiazol-2-yl)ethyl)hydrazinyl)(imino)methyl)acetamide |
| 293 | (structure) | 2-(5-(2,5-difluorophenyl)-2-phenyl-2-(2-(2-(1,4,5,6-tetrahydropyrimidin-2-yl)hydrazinyl)ethyl)-1,3,4-thiadiazol-3(2H)-yl)-5-methyl-1,3,4-thiadiazole |

The biological activities of the compounds of the invention can be demonstrated by the following assays.

BIOLOGICAL ASSAYS

Example A

Enzyme Assay

The activity of the compounds of the present invention may be determined by the following procedure. The assays were conducted at 30° C. in a Costar 3695 (96-well, polystyrene, ½-area, clear) plate in a final volume of 50 µL. Hydrolysis of ATP was monitored in a system that coupled the product ADP to the oxidation of NADH using pyruvate kinase and lactate dehydrogenase. Assay mixtures contained the following: 20 mM K⁺Pipes, pH 7.0, 0.01% Triton X-100, 2% DMSO, 25 mM KCl, 2 mM $MgCl_2$, 1 mM DTT, 25 M ATP, 1 mM phospho(enol)pyruvate, 200 µM NADH, 7.9 U/mL pyruvate kinase, 9 U/mL lactate dehydrogenase, 0.25 M bovine microtubules, 20 M paclitaxel and 20 nM Eg5. The concentration of inhibitor was typically varied over the range of 10-200,000 nM. The reaction was monitored kinetically in an absorbance-based plate reader for a period of 10 minutes. Velocities were estimated from linear fits to the progress curves and were expressed as POC (percent of uninhibited control wells). $IC_{50}$'s were estimated from the POC data using a standard 4-parameter logistical model and compared to a control inhibitor run in each plate. In this assay, compounds of the invention exhibited an $IC_{50}$ of less than 50 µM.

Example B

Cell Viability Assay

The ability of the compounds of the present invention to inhibit cellular viability may be determined by the following procedure. Cells from a variety of established tumor cell lines, e.g. HeLa, were plated in Costar 3904 96-well plates, in growth medium, at a density that allowed for logarithmic growth over the period of the assay, and incubated at 37° C., 5% $CO_2$ overnight. The following day, compounds were added to the cells, at a final DMSO concentration of 0.5%. The concentration of inhibitor was typically varied over the range of 0.1-50,000 nM. Plates were then incubated as above. After a 72 to 96 hour incubation, 20 µL resazurin solution (Cell Titer Blue, Promega G8081) was added to all wells and the plates incubated for a further period of time. Viable cells convert resazurin to resorufin, a fluorescent end-product. The fluorescent signal was determined in a fluorescent plate reader at 560 nm excitation/590 nm emission. The POC (percent of uninhibited control signal) was determined for each well, and the $EC_{50}$ for inhibition of viability was determined from the inflection point of a standard 4-parameter logistical curve fitted to the values obtained. In this assay, compounds of the invention exhibited an $EC_{50}$ of less than 50 µM.

Example C

Mitotic Arrest Assay

Phosphorylation of Histone H3 on Ser10, which peaks in metaphase, is a well-established indicator of mitosis. Phosphorylation in excess of control cells is indicative of mitotic arrest. The ability of the compounds of the present invention to induce mitotic arrest was determined by the following procedure. Cells from a variety of established tumor cell lines, e.g. HeLa, were plated in Greiner 655946, 96-well, poly-D-lysine coated plates, in growth medium and incubated at 37° C., 5% $CO_2$ overnight. The following day, compounds were added to the cells at a final DMSO concentration of 0.5%. The concentration of inhibitor was typically varied over the range of 0.1-50,000 nM. Once compound was added to the cells, plates were incubated as above. After approximately 16 hours, cells were fixed with cold methanol. Plates were blocked and labeled with primary antibody to phospho-Histone H3 (Santa Cruz Biotechnologies SC-8656-R, 1 µg/mL) and to GapDH (RDI TRK-5G4-6C5). The cells were then labeled with secondary antibodies which were conjugated to fluorescent dyes emitting in the near infrared range (Molecular Probes Alexa 680, Rockland IR800) and scanned on a Licor Odyssey or Aerius. The integrated intensity of signal for phosphoHistone H3 was normalized to the signal for GapDH for each well. The POC (percent of completely inhibited control signal) was determined for each well, and the $EC_{50}$ for induction of mitotic arrest was determined from the inflection point of a standard 4-parameter logistical curve fitted to the values obtained. In this assay, compounds of the invention exhibited an $EC_{50}$ of less than 50 µM.

Example D

Tumor Growth Inhibition

The ability of the compounds of this invention to inhibit tumor growth in vivo may be determined by the following procedure, using the HT-29 human colon tumor cell line obtained from the American Type Culture collection (ATCC). HT-29 tumor cells ($3-5 \times 10^6$, in a volume of 100 µL PBS) are implanted subcutaneously in the flank of female nude mice. Tumors are allowed to grow to 150-250 mm$^3$ in size. The length and width of the tumors are measured with calipers, and tumor volume is calculated using the formula: volume= (length×width$^2$)/2. The mice are then randomized into treatment groups, typically 5 to 8 per group, based on tumor volume. The mice then receive vehicle or compound on days 1, 5, 9 by IP injection. Dose is based on weight, measured the day of dosing. Tumor volume and weight are measured twice a week for the duration of the study. Mice are kept on study until tumors grow to about 1500 mm$^3$ in size, after which the mice are euthanized by $CO_2$ inhalation. Tumor volume data are typically reported as V/V(0), where V=tumor volume on the day of measurement, and V(0)=tumor volume at day 1.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A compound of the Formula I:

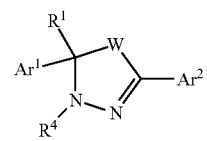

and tautomers, and salts thereof, wherein:

W is $S(O)_m$;

m is 0, 1 or 2;

$R^1$ is $(CH_2)_3NH_2$;

$Ar^1$ and $Ar^2$ are independently phenyl or a 5 or 6 membered heteroaryl ring having 1 to 3 heteroatoms independently selected from N, O and S, wherein said heteroaryl is a carbon radical and said phenyl and heteroaryl are optionally substituted with one or more groups independently selected from halogen, cyano, nitro, azido, —OR$^{10}$, —NR$^{10}$R$^{11}$, —NR$^{10}$SO$_2$R$^{13}$, —SO$_2$NR$^{10}$R$^{11}$, —C(=O)R$^{10}$, —C(=O)OR$^{10}$, —OC(=O)R$^{10}$, —NR$^{10}$C(=O)OR$^{13}$, —NR$^{10}$C(=O)R$^{11}$, —C(=O)NR$^{10}$R$^{11}$, —SR$^{10}$, —S(O)R$^{13}$, —SO$_2$R$^{13}$, —SO$_2$NHC(=O)R$^{10}$, —NR$^{10}$C(=O)NR$^{11}$R$^{12}$, NR$^{10}$C(NCN)NR$^{11}$R$^{12}$, —NR$^{10}$C(H)NR$^{11}$R$^{12}$, —NR$^{10}$C(R$^{13}$)NR$^{11}$R$^{12}$, —OP(=O)(OR$^{10}$)$_2$, alkyl, cycloalkyl, alkenyl, alkynyl, aryl, heteroaryl, arylalkyl, heteroarylalkyl, heterocyclyl and heterocyclylalkyl;

$R^4$ is selected from:

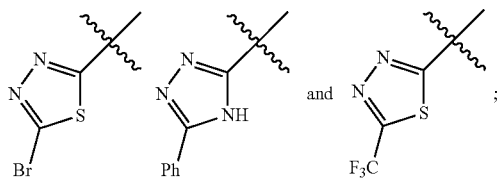 [SMILES: *c1nnc(Br)s1 ; *c1nnc(-c2ccccc2)[nH]1 ; *c1nnc(C(F)(F)F)s1]

and $R^{10}$, $R^{11}$ and $R^{12}$ independently are selected from hydrogen, alkyl, alkenyl, alkynyl, cycloalkyl, aryl, heteroaryl, heterocyclyl and arylalkyl, wherein said alkyl, alkenyl, alkynyl, cycloalkyl, aryl, heteroaryl, heterocyclyl and arylalkyl are optionally substituted with one or more groups independently selected from oxo (with the proviso that it is not on said aryl or heteroaryl portions), halogen, cyano, nitro, $OR^{14}$, $—NR^{14}R^{15}$, trifluoromethyl, difluoromethoxy, trifluoromethoxy, azido, alkyl, cycloalkyl, aryl, heteroaryl, arylalkyl, heteroarylalkyl, heterocyclyl, and heterocyclylalkyl;

$R^{13}$ is alkyl, alkenyl, cycloalkyl, aryl, heteroaryl, heterocyclyl or arylalkyl, wherein said alkyl, alkenyl, cycloalkyl, aryl, heteroaryl, heterocyclyl and arylalkyl are optionally substituted with one to three groups independently selected from oxo (with the proviso that it is not on said aryl or heteroaryl portions), halogen, cyano, nitro, $OR^{14}$, $—NR^{14}R^{15}$, trifluoromethyl, difluoromethoxy, trifluoromethoxy, azido, alkyl, cycloalkyl, aryl, heteroaryl, arylalkyl, heteroarylalkyl, heterocyclyl, and heterocyclylalkyl, or any two of $R^{10}$, $R^{11}$, $R^{12}$ and $R^{13}$ together with the atoms to which they are attached form a 4 to 10 membered heteroaryl or heterocyclic ring, wherein said heteroaryl and heterocyclic rings are optionally substituted with one to three groups independently selected from oxo (with the proviso that it is not on said heteroaryl ring), halogen, cyano, nitro, $OR^{14}$, $—NR^{14}R^{15}$, trifluoromethyl, difluoromethoxy, trifluoromethoxy, azido, alkyl, cycloalkyl, aryl, heteroaryl, arylalkyl, heteroarylalkyl, heterocyclyl, and heterocyclylalkyl;

$R^{14}$ and $R^{15}$ are independently selected from hydrogen, alkyl, alkenyl, lower alkynyl, cycloalkyl, aryl, heteroaryl, heterocyclyl and arylalkyl, or $R^{14}$ and $R^{15}$ together with the atoms to which they are attached form a saturated, partially unsaturated or fully unsaturated 5-6 membered heterocyclyl.

2. The compound of claim 1, wherein $Ar^1$ is phenyl optionally substituted with one or more groups independently selected from halogen, alkyl, $—OR^{10}$ or $—NR^{10}R^{11}$; or $Ar^1$ is a heteroaryl selected from thiophenyl or pyridyl, wherein said pyridyl is optionally substituted independently with one or more halogen.

3. The compound of claim 1, wherein $Ar^1$ is phenyl, 2,4-difluorophenyl, 2-fluorophenyl, 3-fluorophenyl, 2-chlorophenyl, 3-chlorophenyl, 2,5-dichlorophenyl, 2,3-dichlorophenyl, 3,4-dichlorophenyl, 3,5-dichlorophenyl, 2-chloro-5-fluorophenyl, 2-fluoro-5-chlorophenyl, 2-chloro-5-methylphenyl, 2-trifluoromethyl-5-fluorophenyl, 2-fluoro-5-methoxyphenyl, thiophen-2-yl, thiophen-3-yl, 5-chlorothiophen-2-yl, 2-pyridyl, 3-pyridyl, 4-chloropyridin-3-yl, 3-chloropyridin-2-yl, 4-fluoropyridin-3-yl, or 3,6-difluoropyridin-2-yl.

4. The compound of claim 1, wherein $Ar^1$ is phenyl.

5. The compound of claim 1, wherein $Ar^2$ is phenyl optionally substituted with one or more groups independently selected from halogen, $OR^{10}$, $NR^{10}R^{11}$, CN, $NO_2$, $—OP(=O)(OR^{10})_2$, $C(=O)OR^{10}$, or $Ar^2$ is a heteroaryl selected from pyridyl, thiophenyl optionally substituted with alkyl, imidazolyl, and pyrazolyl optionally substituted with $NR^{10}R^{11}$.

6. The compound of claim 1, wherein $Ar^2$ is phenyl, 2-methylphenyl, 3-methylphenyl, 4-methylphenyl, 3,4-dimethylphenyl, 3,5-dimethylphenyl, 2-ethylphenyl, 3-ethylphenyl, 4-t-butylphenyl, 2-chlorophenyl, 4-chlorophenyl, 3-fluorophenyl, 4-fluorophenyl, 4-bromophenyl, 3,4-dichlorophenyl, 3-nitrophenyl, 3-hydroxyphenyl, 3-$(OPO_3H_2)$-phenyl, 3-aminophenyl, 3-carboxyphenyl, 3-cyanophenyl, 2-pyridyl, 3-pyridyl, 5-methylthiophen-2-yl, 2-methylthiazol-4-yl, 2-(1H-imidazol-2-yl), 2-(1H-imidazol-4-yl) or 3-amino-1H-pyrazol-5-yl.

7. The compound of claim 1, wherein $Ar^2$ is 2,4-difluorophenyl.

8. The compound of claim 2, wherein $Ar^2$ is phenyl optionally substituted with one or more groups independently selected from halogen, $OR^{10}$, $NR^{10}R^{11}$, CN, $NO_2$, $—OP(=O)(OR^{10})_2$, $C(=O)OR^{10}$, or $Ar^2$ is a heteroaryl selected from pyridyl, thiophenyl optionally substituted with alkyl, imidazolyl, and pyrazolyl optionally substituted with $NR^{10}R^{11}$.

9. The compound of claim 2, wherein $Ar^2$ is phenyl, 2-methylphenyl, 3-methylphenyl, 4-methylphenyl, 3,4-dimethylphenyl, 3,5-dimethylphenyl, 2-ethylphenyl, 3-ethylphenyl, 4-t-butylphenyl, 2-chlorophenyl, 4-chlorophenyl, 3-fluorophenyl, 4-fluorophenyl, 4-bromophenyl, 3,4-dichlorophenyl, 3-nitrophenyl, 3-hydroxyphenyl, 3-$(OPO_3H_2)$-phenyl, 3-aminophenyl, 3-carboxyphenyl, 3-cyanophenyl, 2-pyridyl, 3-pyridyl, 5-methylthiophen-2-yl, 2-methylthiazol-4-yl, 2-(1H-imidazol-2-yl), 2-(1H-imidazol-4-yl) or 3-amino-1H-pyrazol-5-yl.

10. The compound of claim 2, wherein $Ar^2$ is 2,4-difluorophenyl.

11. The compound of claim 3, wherein $Ar^2$ is phenyl optionally substituted with one or more groups independently selected from halogen, $OR^{10}$, $NR^{10}R^{11}$, CN, $NO_2$, $—OP(=O)(OR^{10})_2$, $C(O)OR^{10}$, or $Ar^2$ is a heteroaryl selected from pyridyl, thiophenyl optionally substituted with alkyl, imidazolyl, and pyrazolyl optionally substituted with $NR^{10}R^{11}$.

12. The compound of claim 3, wherein $Ar^2$ is phenyl, 2-methylphenyl, 3-methylphenyl, 4-methylphenyl, 3,4-dimethylphenyl, 3,5-dimethylphenyl, 2-ethylphenyl, 3-ethylphenyl, 4-t-butylphenyl, 2-chlorophenyl, 4-chlorophenyl, 3-fluorophenyl, 4-fluorophenyl, 4-bromophenyl, 3,4-dichlorophenyl, 3-nitrophenyl, 3-hydroxyphenyl, 3-$(OPO_3H_2)$-phenyl, 3-aminophenyl, 3-carboxyphenyl, 3-cyanophenyl, 2-pyridyl, 3-pyridyl, 5-methylthiophen-2-yl, 2-methylthiazol-4-yl, 2-(1H-imidazol-2-yl), 2-(1H-imidazol-4-yl) or 3-amino-1H-pyrazol-5-yl.

13. The compound of claim 3, wherein $Ar^2$ is 2,4-difluorophenyl.

14. The compound of claim 4, wherein $Ar^2$ is phenyl optionally substituted with one or more groups independently selected from halogen, $OR^{10}$, $NR^{10}R^{11}$, CN, $NO_2$, $—OP(=O)(OR^{10})_2$, $C(=O)OR^{10}$, or $Ar^2$ is a heteroaryl selected from pyridyl, thiophenyl optionally substituted with alkyl, imidazolyl, and pyrazolyl optionally substituted with $NR^{10}R^{11}$.

15. The compound of claim 4, wherein $Ar^2$ is phenyl, 2-methylphenyl, 3-methylphenyl, 4-methylphenyl, 3,4-dimethylphenyl, 3,5-dimethylphenyl, 2-ethylphenyl, 3-ethylphenyl, 4-t-butylphenyl, 2-chlorophenyl, 4-chlorophenyl, 3-fluorophenyl, 4-fluorophenyl, 4-bromophenyl, 3,4-dichlorophenyl, 3-nitrophenyl, 3-hydroxyphenyl, 3-($OPO_3H_2$)-phenyl, 3-aminophenyl, 3-carboxyphenyl, 3-cyanophenyl, 2-pyridyl, 3-pyridyl, 5-methylthiophen-2-yl, 2-methylthiazol-4-yl, 2-(1H-imidazol-2-yl), 2-(1H-imidazol-4-yl) or 3-amino-1H-pyrazol-5-yl.

16. The compound of claim 4, wherein $Ar^2$ is 2,4-difluorophenyl.

17. The compound of claim 1, wherein W is S.

18. The compound of claim 1, selected from the group consisting of:
   3-(5-(2,5-difluorophenyl)-2-phenyl-3-(5-phenyl-4H-1,2,4-triazol-3-yl)-2,3-dihydro-1,3,4-thiadiazol-2-yl)propan-1-amine;
   3-(5-(2,5-difluorophenyl)-2-phenyl-3-(5-(trifluoromethyl)-1,3,4-thiadiazol-2-yl)-2,3-dihydro-1,3,4-thiadiazol-2-yl)propan-1-amine; and
   3-(3-(5-bromo-1,3,4-thiadiazol-2-yl)-5-(2,5-difluorophenyl)-2-phenyl-2,3-dihydro-1,3,4-thiadiazol-2-yl)propan-1-amine;
   and salts thereof.

19. A composition comprising a compound of claim 1, and a pharmaceutically acceptable carrier.

* * * * *